(12) United States Patent
Suh et al.

(10) Patent No.: US 9,084,594 B2
(45) Date of Patent: Jul. 21, 2015

(54) METHODS FOR THE PREVENTION OF SURGICAL SITE INFECTIONS

(71) Applicant: The Board of Trustees of the Leland Stanford Junior University, Palo Alto, CA (US)

(72) Inventors: Insoo Suh, San Francisco, CA (US); Jonathan Coe, Menlo Park, CA (US); Swaminadhan Gnanashanmugam, San Francisco, CA (US); Jeremy Koehler, East Palo Alto, CA (US); Mark Welton, Stanford, CA (US)

(73) Assignee: The Board of Trustees of the Lealand Stanford Junior University, Palo Alto, CA (US)

( * ) Notice: Subject to any disclaimer, the term of this patent is extended or adjusted under 35 U.S.C. 154(b) by 114 days.

(21) Appl. No.: 13/736,875

(22) Filed: Jan. 8, 2013

(65) Prior Publication Data

US 2013/0178709 A1     Jul. 11, 2013

Related U.S. Application Data

(60) Provisional application No. 61/585,052, filed on Jan. 10, 2012, provisional application No. 61/603,673, filed on Feb. 27, 2012, provisional application No. 61/620,813, filed on Apr. 5, 2012, provisional application No. 61/651,263, filed on May 24, 2012.

(51) Int. Cl.
*A61B 1/32*     (2006.01)
*A61B 17/02*    (2006.01)
*A61B 17/00*    (2006.01)

(52) U.S. Cl.
CPC ......... *A61B 17/0293* (2013.01); *A61B 17/0218* (2013.01); *A61B 2017/00539* (2013.01); *A61B 2017/00544* (2013.01); *A61B 2017/00557* (2013.01)

(58) Field of Classification Search
CPC ........... A61B 17/0218; A61B 17/0293; A61B 2017/0225; A61B 2217/005; A61B 2217/007
USPC ............... 600/201–246; 604/513, 73, 103.01, 604/102, 164.01, 174, 28, 19, 27, 35, 43–48
See application file for complete search history.

(56) References Cited

U.S. PATENT DOCUMENTS

| | | | |
|---|---|---|---|
| 1,157,202 | A | 10/1915 | Bates et al. |
| 1,255,182 | A | 2/1918 | Krupski |

(Continued)

FOREIGN PATENT DOCUMENTS

WO     WO 91/02466 A1     3/1991

OTHER PUBLICATIONS

Cheadle, W.G., Risk Factors for Surgical Site Infection, Surgical Infections 7(s1):s7-s11, 2006.

(Continued)

*Primary Examiner* — Eduardo C Robert
*Assistant Examiner* — Jacqueline Johanas
(74) *Attorney, Agent, or Firm* — Knobbe, Martens, Olson & Bear, LLP

(57) ABSTRACT

Several methods to reduce surgical site infections include inserting a surgical access device into an incision, retracting tissue, and introducing fluid into the surgical access device such that the fluid exits the surgical access device and irrigates a surgical site. Other methods do not include introducing fluid into a surgical access device but include suctioning a fluid into the surgical access device and removing the fluid from the body.

22 Claims, 55 Drawing Sheets

(56) References Cited

U.S. PATENT DOCUMENTS

| | | | |
|---|---|---|---|
| 1,810,466 A | 6/1931 | Deutsch | |
| 1,947,649 A | 2/1934 | Kadavy | |
| 2,305,289 A | 4/1940 | Coburg | |
| 2,313,164 A | 3/1943 | Nelson | |
| 2,812,758 A | 7/1955 | Blumenschein | |
| 3,111,943 A | 11/1963 | Orndorff | |
| 3,332,417 A | 7/1967 | Blanford et al. | |
| 3,347,226 A | 10/1967 | Harrower | |
| 3,347,227 A | 10/1967 | Harrower | |
| 3,347,277 A | 10/1967 | Gwinn, Jr. | |
| 3,397,692 A | 8/1968 | Creager, Jr. | |
| 3,402,710 A | 9/1968 | Paleschuk | |
| 3,416,520 A | 12/1968 | Crreager, Jr. | |
| 3,496,687 A | 2/1970 | Greenberg et al. | |
| 3,672,104 A | 6/1972 | Luckey | |
| 3,807,393 A | 4/1974 | McDonald | |
| 3,939,727 A | 2/1976 | Asquith | |
| 4,024,872 A | 5/1977 | Muldoon | |
| 4,188,945 A | 2/1980 | Wenander | |
| 4,239,036 A | 12/1980 | Krieger | |
| 4,553,537 A | 11/1985 | Rosenberg | |
| 4,777,943 A | 10/1988 | Chvapil | |
| 4,889,107 A | 12/1989 | Kaufman | |
| 4,942,700 A | 7/1990 | Hoberman | |
| 4,984,564 A | 1/1991 | Yuen | |
| 5,024,031 A | 6/1991 | Hoberman | |
| 5,038,532 A | 8/1991 | Shahinpoor | |
| 5,105,983 A | 4/1992 | Sancoff et al. | |
| 5,146,916 A | 9/1992 | Catalani | |
| 5,159,921 A | 11/1992 | Hoover | |
| 5,263,922 A | 11/1993 | Sova et al. | |
| 5,284,481 A | 2/1994 | Soika et al. | |
| 5,352,201 A | 10/1994 | Jemmott | |
| 5,358,494 A | 10/1994 | Svedman | |
| 5,364,356 A | 11/1994 | Höfling | |
| 5,366,478 A | 11/1994 | Brinkerhoff et al. | |
| 5,437,683 A | 8/1995 | Neumann et al. | |
| 5,520,610 A | 5/1996 | Giglio et al. | |
| 5,522,791 A | 6/1996 | Leyva | |
| 5,524,644 A | 6/1996 | Crook | |
| 5,562,690 A | 10/1996 | Green et al. | |
| 5,616,121 A | 4/1997 | McKay | |
| 5,632,284 A | 5/1997 | Graether | |
| 5,643,178 A * | 7/1997 | Moll et al. | 600/204 |
| 5,649,550 A | 7/1997 | Crook | |
| 5,738,629 A * | 4/1998 | Moll et al. | 600/116 |
| 5,741,298 A | 4/1998 | MacLeod | |
| 5,761,871 A | 6/1998 | Atake | |
| 5,810,721 A | 9/1998 | Mueller et al. | |
| 5,832,925 A | 11/1998 | Rothrum | |
| 5,853,395 A | 12/1998 | Crook et al. | |
| 5,865,728 A * | 2/1999 | Moll et al. | 600/204 |
| 5,871,474 A | 2/1999 | Hermann et al. | |
| 5,899,208 A | 5/1999 | Bonadio | |
| 5,902,266 A | 5/1999 | Leone et al. | |
| 5,906,577 A | 5/1999 | Beane et al. | |
| 5,947,922 A | 9/1999 | MacLeod | |
| 5,951,588 A | 9/1999 | Moenning | |
| 5,964,781 A | 10/1999 | Mollenauer et al. | |
| 5,984,943 A * | 11/1999 | Young | 606/190 |
| 6,010,494 A | 1/2000 | Schäfer et al. | |
| 6,033,426 A | 3/2000 | Kaji | |
| 6,033,428 A * | 3/2000 | Sardella | 606/213 |
| 6,045,535 A | 4/2000 | Ben Nun | |
| 6,048,309 A | 4/2000 | Flom et al. | |
| 6,077,288 A | 6/2000 | Shimomura et al. | |
| 6,090,043 A | 7/2000 | Austin et al. | |
| 6,142,935 A | 11/2000 | Flom et al. | |
| 6,142,936 A | 11/2000 | Beane et al. | |
| 6,149,642 A | 11/2000 | Gerhart et al. | |
| 6,150,608 A | 11/2000 | Wambeke et al. | |
| 6,162,172 A | 12/2000 | Cosgrove et al. | |
| 6,219,974 B1 | 4/2001 | Hoberman | |
| 6,254,533 B1 | 7/2001 | Fadem et al. | |
| 6,254,534 B1 | 7/2001 | Butler et al. | |
| 6,331,850 B1 | 12/2001 | Olodort et al. | |
| 6,382,211 B1 | 5/2002 | Crook | |
| 6,383,162 B1 | 5/2002 | Sugarbaker | |
| 6,440,063 B1 | 8/2002 | Beane et al. | |
| 6,450,983 B1 | 9/2002 | Rambo | |
| 6,578,577 B2 | 6/2003 | Bonadio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,695,824 B2 | 2/2004 | Howard et al. | |
| 6,723,044 B2 | 4/2004 | Pulford et al. | |
| 6,739,098 B2 | 5/2004 | Hoberman | |
| 6,814,078 B2 | 11/2004 | Crook | |
| 6,814,700 B1 | 11/2004 | Mueller et al. | |
| 6,846,287 B2 | 1/2005 | Bonadio et al. | |
| 6,908,430 B2 | 6/2005 | Caldwell et al. | |
| 6,918,312 B2 | 7/2005 | Elwood et al. | |
| 6,939,296 B2 | 9/2005 | Ewers et al. | |
| 6,945,932 B1 | 9/2005 | Caldwell et al. | |
| 6,958,037 B2 | 10/2005 | Ewers et al. | |
| 6,972,026 B1 | 12/2005 | Caldwell et al. | |
| 7,008,377 B2 | 3/2006 | Beane et al. | |
| 7,033,319 B2 | 4/2006 | Pulford et al. | |
| 7,052,454 B2 | 5/2006 | Taylor | |
| 7,081,089 B2 | 7/2006 | Bonadio et al. | |
| 7,100,333 B2 | 9/2006 | Hoberman | |
| 7,163,510 B2 | 1/2007 | Kahle et al. | |
| 7,195,590 B2 | 3/2007 | Butler et al. | |
| 7,214,185 B1 | 5/2007 | Rosney et al. | |
| 7,235,062 B2 | 6/2007 | Brustad | |
| 7,238,154 B2 | 7/2007 | Ewers et al. | |
| 7,297,106 B2 | 11/2007 | Yamada et al. | |
| 7,300,399 B2 | 11/2007 | Bonadio et al. | |
| 7,377,898 B2 | 5/2008 | Ewers et al. | |
| 7,393,322 B2 | 7/2008 | Wenchell | |
| 7,445,597 B2 | 11/2008 | Butler et al. | |
| 7,473,221 B2 | 1/2009 | Ewers et al. | |
| 7,481,765 B2 | 1/2009 | Ewers et al. | |
| 7,537,564 B2 | 5/2009 | Bonadio et al. | |
| 7,540,215 B2 | 6/2009 | Hoberman et al. | |
| 7,540,839 B2 | 6/2009 | Butler et al. | |
| 7,559,893 B2 | 7/2009 | Bonadio et al. | |
| 7,644,721 B2 | 1/2010 | Hoberman et al. | |
| 7,650,887 B2 | 1/2010 | Nguyen et al. | |
| 7,666,718 B2 | 2/2010 | Suzawa et al. | |
| 7,704,207 B2 | 4/2010 | Albrecht et al. | |
| 7,717,847 B2 | 5/2010 | Smith | |
| 7,727,146 B2 | 6/2010 | Albrecht et al. | |
| 7,736,306 B2 | 6/2010 | Brustad et al. | |
| 7,758,500 B2 | 7/2010 | Boyd et al. | |
| 7,815,567 B2 | 10/2010 | Albrecht et al. | |
| 7,867,164 B2 | 1/2011 | Butler et al. | |
| 7,878,974 B2 | 2/2011 | Brustad et al. | |
| 7,883,461 B2 | 2/2011 | Albrecht et al. | |
| 7,892,172 B2 | 2/2011 | Albrecht et al. | |
| 7,909,760 B2 | 3/2011 | Albrecht et al. | |
| 7,909,761 B2 | 3/2011 | Banchieri et al. | |
| 7,913,697 B2 | 3/2011 | Nguyen et al. | |
| 7,928,281 B2 | 4/2011 | Augustine | |
| 7,951,076 B2 | 5/2011 | Hart et al. | |
| 7,967,748 B2 | 6/2011 | Kistler et al. | |
| 7,998,068 B2 | 8/2011 | Bonadio et al. | |
| 8,012,088 B2 | 9/2011 | Butler et al. | |
| 8,016,755 B2 | 9/2011 | Ewers et al. | |
| 8,021,296 B2 | 9/2011 | Bonadio et al. | |
| 8,033,995 B2 * | 10/2011 | Cropper et al. | 600/207 |
| 8,070,676 B2 | 12/2011 | Ewers et al. | |
| 8,075,482 B2 | 12/2011 | Beckman et al. | |
| 8,105,234 B2 | 1/2012 | Ewers et al. | |
| 8,109,873 B2 | 2/2012 | Albrecht et al. | |
| 8,142,354 B1 | 3/2012 | Larson et al. | |
| 8,226,552 B2 | 7/2012 | Albrecht et al. | |
| 8,241,260 B2 | 8/2012 | Livne et al. | |
| 8,282,545 B1 * | 10/2012 | Bodenstein | 600/206 |
| 8,291,781 B2 | 10/2012 | Guerrero et al. | |
| 8,357,188 B2 | 1/2013 | Boynton et al. | |
| 8,733,453 B2 | 5/2014 | Guerrero et al. | |
| 8,814,788 B2 * | 8/2014 | Gan | 600/206 |

(56) References Cited

U.S. PATENT DOCUMENTS

| | | | |
|---|---|---|---|
| 2002/0002324 A1 | 1/2002 | McManus | |
| 2003/0187376 A1 | 10/2003 | Rambo | |
| 2003/0192553 A1 | 10/2003 | Rambo | |
| 2004/0154624 A1 | 8/2004 | Bonadio et al. | |
| 2004/0267096 A1 | 12/2004 | Caldwell et al. | |
| 2005/0020884 A1 | 1/2005 | Hart et al. | |
| 2005/0148823 A1 | 7/2005 | Vaugh | |
| 2005/0155611 A1 | 7/2005 | Vaugh et al. | |
| 2005/0222582 A1 | 10/2005 | Wenchell | |
| 2005/0261720 A1 | 11/2005 | Caldwell et al. | |
| 2005/0273131 A1 | 12/2005 | Shluzas et al. | |
| 2005/0283050 A1 | 12/2005 | Gundlapalli et al. | |
| 2006/0004261 A1 | 1/2006 | Douglas | |
| 2006/0074278 A1 | 4/2006 | Petit et al. | |
| 2006/0095020 A1 | 5/2006 | Casas et al. | |
| 2006/0149137 A1 | 7/2006 | Pingleton et al. | |
| 2006/0149306 A1 | 7/2006 | Hart et al. | |
| 2006/0161050 A1 | 7/2006 | Butler et al. | |
| 2006/0270911 A1* | 11/2006 | Voegele et al. | 600/235 |
| 2007/0062948 A1 | 3/2007 | Albrecht et al. | |
| 2007/0073110 A1 | 3/2007 | Larson et al. | |
| 2008/0081951 A1* | 4/2008 | Frasier et al. | 600/207 |
| 2008/0208222 A1 | 8/2008 | Beckman et al. | |
| 2008/0275408 A1 | 11/2008 | Boynton et al. | |
| 2008/0281162 A1 | 11/2008 | Albrecht et al. | |
| 2008/0281297 A1 | 11/2008 | Pesach et al. | |
| 2009/0118587 A1* | 5/2009 | Voegele et al. | 600/206 |
| 2009/0192360 A1* | 7/2009 | Riess et al. | 600/210 |
| 2009/0287060 A1* | 11/2009 | Pell et al. | 600/201 |
| 2010/0063375 A1 | 3/2010 | Kassab et al. | |
| 2010/0100043 A1 | 4/2010 | Racenet | |
| 2010/0145152 A1 | 6/2010 | Smith et al. | |
| 2010/0198329 A1 | 8/2010 | Kassab et al. | |
| 2010/0261974 A1 | 10/2010 | Shelton, IV et al. | |
| 2010/0312064 A1* | 12/2010 | Weisenburgh et al. | 600/206 |
| 2010/0312066 A1* | 12/2010 | Cropper et al. | 600/207 |
| 2010/0324375 A1* | 12/2010 | Piskun | 600/207 |
| 2011/0054260 A1 | 3/2011 | Albrecht et al. | |
| 2011/0118551 A1* | 5/2011 | Ciporen et al. | 600/201 |
| 2011/0124973 A1 | 5/2011 | Ross | |
| 2011/0137267 A1 | 6/2011 | Phillips et al. | |
| 2011/0282160 A1* | 11/2011 | Bhadri et al. | 600/236 |
| 2011/0319719 A1 | 12/2011 | O'Prey et al. | |
| 2012/0022334 A1* | 1/2012 | Piskun | 600/208 |
| 2012/0203069 A1* | 8/2012 | Hannaford et al. | 600/201 |
| 2012/0245423 A1* | 9/2012 | Rodrigues | 600/205 |
| 2012/0245425 A1* | 9/2012 | Okoniewski | 600/207 |
| 2013/0030252 A1* | 1/2013 | Kaul | 600/204 |
| 2013/0178709 A1* | 7/2013 | Suh et al. | 600/205 |
| 2013/0178710 A1* | 7/2013 | Suh et al. | 600/205 |
| 2013/0184535 A1* | 7/2013 | Suh et al. | 600/210 |

OTHER PUBLICATIONS

Lord, J., et al., Intraoperative Antibiotic Wound Lavage: An Attempt to Eliminate Postoperative Infection in Arterial and Clean General Surgical Procedures, Ann. Surg. 185(6):634, 1977.

Bennett-Guerrero, E., et al., Gentamicin-Collagen Sponge for Infection Prophylaxis in Colorectal Surgery, N. Engl. J. Med. 363(11):1038-1049, 2010.

Office action dated Nov. 20, 2014 for U.S. Appl. No. 13/736,904.

* cited by examiner

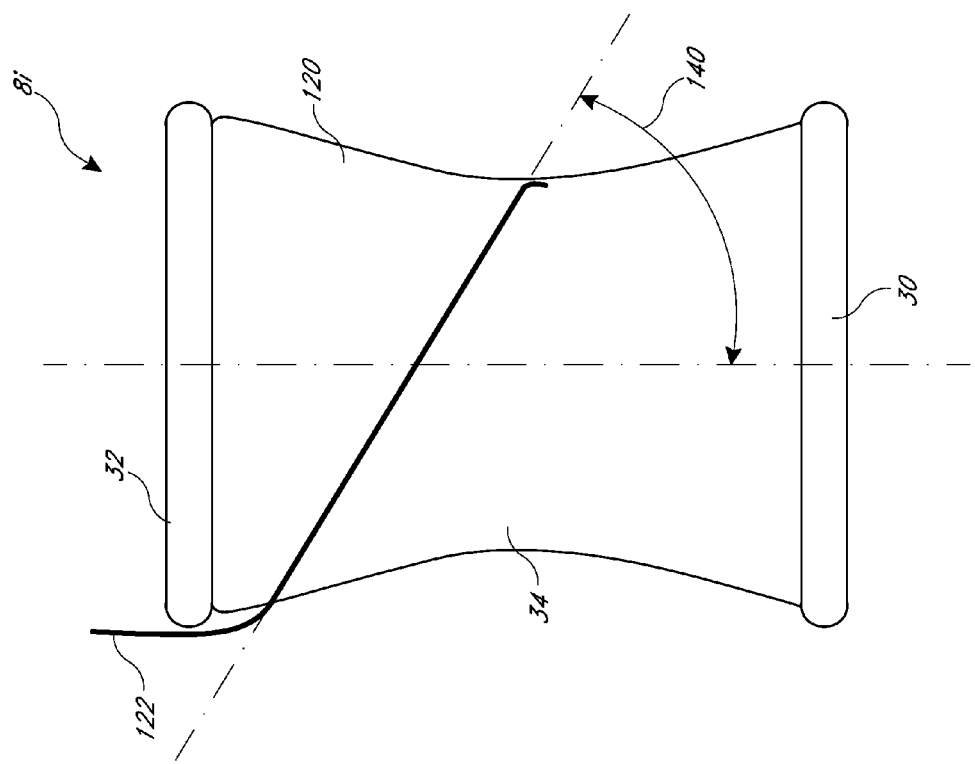

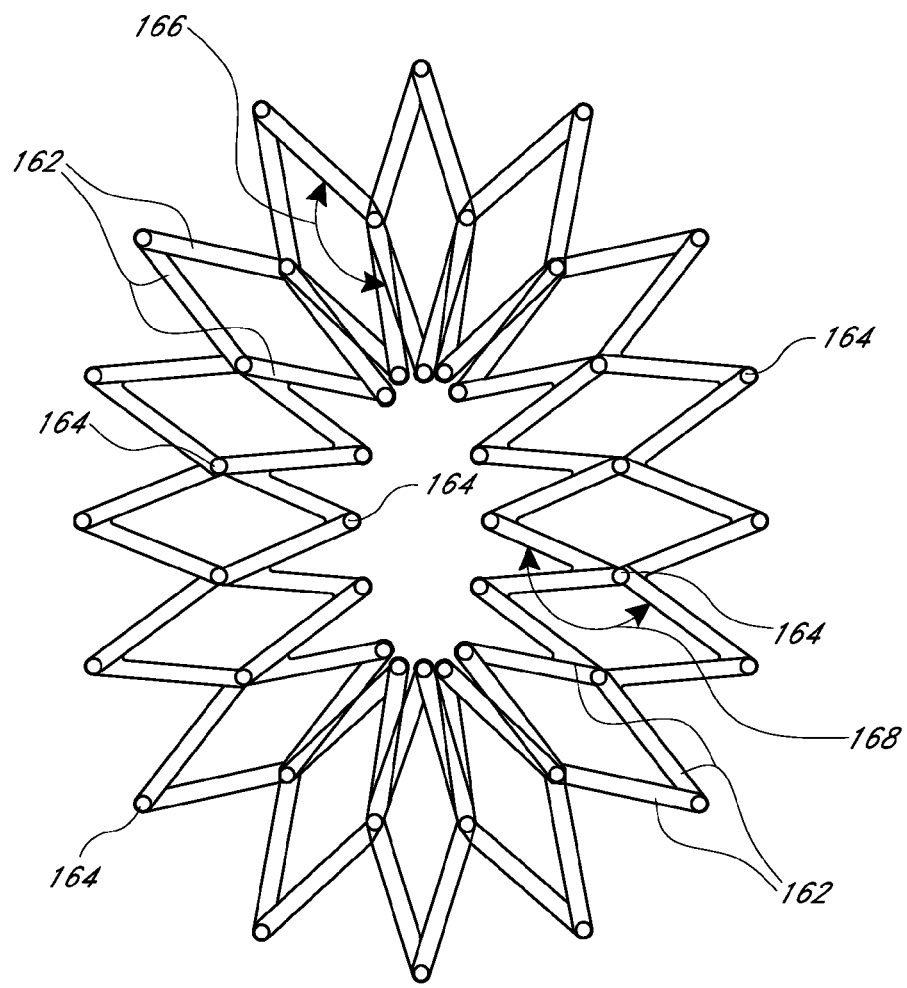
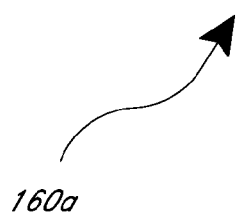
FIG. 31B

METHODS FOR THE PREVENTION OF SURGICAL SITE INFECTIONS

CROSS-REFERENCE TO RELATED APPLICATIONS

This application claims the benefit of U.S. Provisional Patent Application No. 61/585,052, entitled METHOD AND DEVICE FOR THE PREVENTION OF INCISIONAL SURGICAL SITE INFECTIONS, and filed Jan. 10, 2012; U.S. Provisional Patent Application No. 61/603,673, entitled METHODS AND DEVICES FOR THE PREVENTION OF INCISIONAL SURGICAL SITE INFECTIONS, and filed Feb. 27, 2012; U.S. Provisional Patent Application No. 61/620,813, entitled METHOD AND DEVICE FOR THE PREVENTION OF INCISIONAL SURGICAL SITE INFECTIONS, and filed Apr. 5, 2012; and U.S. Provisional Patent Application No. 61/651,263, entitled METHODS AND DEVICES FOR THE PREVENTION OF INCISIONAL SURGICAL SITE INFECTIONS, and filed May 24, 2012, the entire contents of which are incorporated herein by reference.

BACKGROUND OF THE INVENTION

1. Field of the Invention

The field of the present application pertains to medical devices, and more particularly, to methods, systems, and devices to facilitate access to a surgical site within a body.

2. Background

Formerly known as "wound infection," surgical site infection (SSI) is generally defined by the Centers for Disease Control and Prevention (CDC) as an infection in the area of the surgical incision that occurs within 30 days of an operation. The CDC further subdivides SSI into two groups. The first group includes superficial and deep "incisional" SSI (ISSI). The second group includes "organ/space" SSI. These two groups appear to be somewhat different phenomena with respect to etiology, physiology, pathogenesis, clinical presentation, and treatment. Of note, the term "wound infection," as currently used in the medical colloquium, refers to and is more compatible with ISSI, as opposed to organ/space SSI.

ISSI affects approximately 3-4% of the more than 30 million operations performed in the U.S. each year. Although the state of current medical care has minimized the mortality associated with ISSI, the morbidity and associated costs to the healthcare system remain significant. On average, ISSI extends the length of an inpatient hospital stay by 9 days, as well as introduces the added necessity and costs of outpatient wound management, which can reach upwards of 10,000-45,000 U.S. dollars per patient. Estimates of the aggregate annual burden to the U.S. healthcare system exceed five billion U.S. dollars.

The diagnosis of SSI is usually made by a physician and is usually based on the clinical finding of various signs and symptoms of infection at the incisional site, such as pain, tenderness, swelling, redness, warmth, and purulent drainage. Various ancillary tests, such as microbial cultures or radiographic exams (e.g., computed tomography scans), can aid in the diagnosis. The length of treatment can extend for weeks or even months.

Obese patients are particularly vulnerable to developing wound infections, with a two to three fold increased risk relative to the overall population. This is at least partially due to the poor vascularization of subcutaneous fat, reducing the delivery of prophylactic intravenous (IV) antibiotics to the incision site. Furthermore, subcutaneous fat is an excellent media for the incubation of bacterial infection. With increasing rates of obesity worldwide, this will only further compound the problem of ISSI.

Another risk factor for the development of ISSI is the type of surgical procedure performed. For example, colorectal surgeries are associated with a baseline infection rate of 15-20%. This is a result of the contaminated nature of the procedure, as fecal contents are often released into the operative field when colon, small bowel, or rectum is cut. Furthermore, colorectal surgery involves the manipulation and removal of large organs (e.g. the colon), and consequently, large incisions are often required to perform the procedures. ISSI risk is directly correlated with the size of surgical incision used to perform the case. These risks are further compounded when combined with other risk factors such as obesity. For example, the rates of wound infections in obese patients undergoing colorectal surgery increase to upwards of 33%, representing a major burden to the healthcare system in terms of the quality and cost of services.

Prior surgical instruments and methods have been developed with the aim of reducing wound infections, yet the scope of the problem has not been reduced. Some solutions have addressed the issue by implanting degradable sponges in the incision to combat the development of wound infections postoperatively. However, this approach led to increases in wound infection rates, as the immune system reacts poorly to the implant because the implant is a "foreign body."

Surgeons have previously irrigated the incision or wound margins with fluids such as saline and/or antibiotics, but the practice has proved to be disruptive to surgical progress, difficult to implement and standardize in surgical practices, and consumes valuable time, increasing patient risk and increasing operative costs.

Barrier wound protectors have also been employed to prevent the egress of bacteria into the incision, but this is merely a passive approach, and considering the barrier protection must be removed to complete the operation, the incision is inevitably exposed to the infectious contents contained within the surgical field. Additionally, wound protectors may be difficult to manipulate, especially when positioned in the surgical field. A further drawback is that the barrier can also trap bacteria onto the wound surface, allowing bacteria to proliferate in the wound space.

Considering the significant morbidity and cost associated with SSI, it is desirable to provide a way to reduce the occurrence of SSI that is superior to the limitations of currently available commercial devices.

In select situations, a key aspect of surgery involves obtaining adequate surgical "exposure," or alternatively, adequate visualization and access to target anatomical landmarks and structures to be operated upon. To achieve proper exposure, surgeons can use a variety of surgical retractors generally configured to maximize the opening of the incision and create space within the operative region (e.g. chest, abdomen, orbit, neck, and groin) to facilitate the completion of the surgical procedure.

One surgical retractor used in abdominal surgery involves a top ring, bottom ring, and flexible tubular sheath disposed between the top and bottom rings. In numerous embodiments, manipulation of the top ring in a variety of ways (e.g., by rolling the sheath around the top ring) is sometimes effective to shorten the sheath length and retract the edges of the incision. In many cases, such surgical retractors incorporate barrier wound protection, the disadvantages of which have already been described.

The drawbacks of surgical retractors described in currently available commercial devices are numerous. They can be difficult to use, requiring additional time and the manual application of forces that may be difficult for surgeons to apply in an operative setting. They may require more than 1 person to operate, decreasing focus on the operative field, increasing operative time and personnel costs. In addition, due to the unpredictable nature of a surgical operation, the initial incision size may not be ideal, thus requiring lengthening during the course of the procedure. Many commercially available surgical retractors do not allow for an increase in incision size with the device in site. Moreover, currently available commercial surgical retractors may employ a design requiring a variety of sizes to accommodate the wide range of incision sizes encountered during surgery. As a result, hospitals may have to stock a range of device sizes, and often multiple devices are used in a single procedure as the size of the incision may be increased. Using multiple devices may result in increased healthcare costs, surgery duration, and infections.

BRIEF SUMMARY

It would therefore be desirable to provide improved surgical retractors which address at least some of the possible shortcomings of existing devices. Moreover, it would also be desirable if improved surgical retractors helped to reduce the incidence of SSI. At least some of these objectives are met by the exemplary embodiments described below. Not necessarily all such aspects or advantages are achieved by any particular embodiment. Thus, various embodiments may be carried out in a manner that achieves or optimizes one advantage or group of advantages as taught herein without necessarily achieving other aspects or advantages as may also be taught or suggested herein. For example, some embodiments reduce SSI but do not necessarily provide access to structures upon which a physician needs to operate. Several of the embodiments improve upon prior art retractors by transforming the retractors into systems that reduce SSI. Several embodiments provide access to structures upon which a physician needs to operate but do not necessarily reduce SSI.

Various embodiments described below are directed to surgical access devices that are adapted to facilitate access to a surgical site within a body of a patient through an incision in the body. The surgical access device embodiments can comprise a first retention ring; a second retention ring configured to expand from a collapsed configuration to an expanded configuration; and a pliable membrane extending between the first retention ring and the second retention ring. The pliable membrane can be configured to expand the incision to facilitate access to the surgical site. The surgical access device can also include a fluid delivery member coupled with at least one of the first retention ring, the second retention ring or the pliable membrane for delivering fluid to the surgical site.

The first retention ring can be deformable. The first retention ring can also be an expandable retention ring. In various embodiments, the second retention ring is configured to selectively maintain the expanded configuration. In some embodiments, the second retention ring comprises at least four linkages pivotably coupled to one another such that expanding the second retention ring causes the linkages to pivot relative to each other.

The second retention ring can also comprise ratchet teeth configured to selectively maintain the expanded configuration. The second retention ring can also comprise at least one ratchet pawl configured to selectively maintain the expanded configuration by engaging at least a portion of the ratchet teeth. The surgical access device can also include a release member configured to disengage the ratchet pawl from the ratchet teeth to enable the second retention ring to return to the collapsed configuration. In some embodiments, the surgical access device comprises a user interface button coupled to at least one of the ratchet teeth or to the ratchet pawl. The user interface button can be configured to disengage the ratchet pawl from the ratchet teeth to enable the second retention ring to return to the collapsed configuration.

The surgical access device can also include a locking mechanism configured to selectively lock the second retention ring in the expanded configuration. The locking mechanism can comprise an indentation and a protrusion. The protrusion can be configured to engage the indentation to selectively lock the second retention ring in the expanded configuration.

In certain embodiments, the pliable membrane comprises a tubular membrane, wherein the tubular membrane comprises a first end and a second end. The first end is coupled to the first retention ring and the second end is coupled to the second retention ring. The fluid delivery member can comprise a lumen with holes where the holes are configured to deliver fluid to the surgical site. The fluid delivery member can also comprise a porous medium and/or a perforated membrane.

In various embodiments, the surgical access device comprises a fluid removal member coupled with at least one of the first retention ring, the second retention ring or the pliable membrane for removing fluid from the surgical site. The fluid removal member can comprise a suction member.

The first retention ring can be configured for advancement through the incision into the body. The second retention ring can be configured for placement outside the body.

In at least one embodiment, a surgical access system is adapted to facilitate access to a surgical site within a body of a patient through an incision in the body. The surgical access system can comprise a first retention ring configured for placement within the body at or near the surgical site; a second retention ring configured for placement outside the body; and a pliable membrane extending between the first retention ring and the second retention ring. The system can also include a fluid delivery inlet coupled with the pliable membrane for introducing fluid into the surgical access system and at least one opening in the pliable membrane, wherein the at least one opening is in fluid communication with the fluid delivery inlet to allow the fluid introduced into the fluid delivery inlet to exit the surgical access system. The system can also include a fluid removal member coupled with at least one of the first retention ring or the pliable membrane for removing fluid from the surgical site.

In some embodiments, the pliable membrane comprises a circumferential fluid dispersion ring. In other embodiments, the pliable membrane comprises a fluid-permeable tube. The fluid-permeable tube can comprise openings configured to deliver the fluid to the surgical site.

In select embodiments, the pliable membrane comprises a tubular membrane and a tube with at least one lumen disposed in a spiral direction around the tubular membrane. A wire can be disposed inside at least a portion of the tube. In various embodiments, the surgical access system comprises a flow regulator in fluid communication with the fluid delivery inlet.

In some surgical access systems, the pliable membrane comprises a fluid-permeable material and the surgical access system is configured to deliver the fluid from the fluid delivery inlet to the fluid-permeable material. The fluid-permeable material can be configured to deliver the fluid to the surgical site. The fluid-permeable material can be a porous medium. The surgical access system can also include a first fluid conduit member in fluid communication with the fluid delivery inlet. The fluid removal member can comprise a second fluid conduit member coupled to the first retention ring. The first retention ring sometimes comprises a hollow ring. The second fluid conduit member can be in fluid communication with the hollow ring.

In several embodiments, the surgical access system comprises a suction tube and the second fluid conduit member is in fluid communication with the suction tube. The pliable membrane can comprise a tubular membrane. The tubular membrane can comprise an upper portion and a lower portion. The lower portion is closer than the upper portion to the first retention ring. A first fluid conduit member can be in fluid communication with the upper portion, and a second fluid conduit member can be in fluid communication with the lower portion.

In certain embodiments, the first retention ring and the second retention ring are circular. The surgical access system comprises a third retention ring in several embodiments. The surgical access system can also comprise a fourth retention ring.

In various embodiments, a method for retracting tissue and providing fluid to a surgical site in a body during a surgical procedure comprises advancing a first retention ring into the body through an incision in a collapsed configuration and placing a second retention ring outside the body, wherein the second retention ring is coupled to the first retention ring by a pliable membrane. The method can also include retracting the tissue using the pliable membrane and introducing the fluid into a fluid delivery inlet coupled to the pliable membrane such that the fluid exits the pliable membrane through at least one opening in the pliable membrane. The method can also include suctioning the fluid into the pliable membrane and removing the fluid from the body.

In several embodiments, a fluid conduit member is coupled to the first retention ring and the method comprises suctioning the fluid into the fluid conduit member and removing the fluid from the body. The fluid can comprise an antibiotic fluid. The fluid can also comprise a saline solution.

In some embodiments, the method comprises expanding the second retention ring whereby expanding the second retention ring causes the pliable membrane to retract the tissue around the incision. The second retention ring can comprise at least four linkages pivotably coupled to one another. Expanding the second retention ring can comprise pivoting the at least four linkages relative to each other. In various embodiments, a wire is spirally wound around the pliable membrane and the retracting the tissue comprises pulling the wire. In some embodiments, retracting the tissue comprises inflating at least a portion of the pliable membrane.

In multiple embodiments, a surgical access device that is adapted to facilitate access to a surgical site through an incision in a patient's body comprises a first a first retention member, an expandable second retention member, and a pliable membrane. The expandable second retention member can have a collapsed configuration and an expanded configuration. The pliable membrane can have a first end, a second end, an inner layer and an outer layer. The first end can be coupled to the first retention member, and the second end can be coupled to the second retention member. The inner layer and the outer layer form a space there between that carries a fluid. In these embodiments, when the pliable membrane expands radially outward, it engages and expands the incision when the second retention member is actuated into the expanded configuration.

Some embodiments include a pliable membrane that has a hydrophilic coating disposed thereon, and the hydrophilic coating helps disperse the fluid along the membrane. One or more channels may be disposed on a surface of the pliable membrane such as the membrane's outer surface. The channels may direct the fluid along the pliable membrane. The fluid may be delivered from the channels to tissue in the surgical site that is adjacent the pliable membrane.

In several embodiments, the inner layer and outer layer of the pliable membrane may be coupled together with a plurality of joined locations there between and this may prevent separation of the layers from one another. The joined locations may form a plurality of chambers in the space, and the fluid may flow into and out of a chamber without passing into another chamber. The pliable membrane may comprise a plurality of perforations, and the fluid may exit the space via the plurality of perforations. The plurality of perforations may comprise a first and a second perforation. The first perforation may be fluidly disposed along a first fluid path through the pliable membrane, and a second perforation may be fluidly disposed along a second fluid path in the pliable membrane. The first fluid path may be fluidly independent of the second fluid path.

The access device may further comprise a fluid delivery member such as one or more tubes, that is fluidly coupled with the space. A porous material may be disposed in the space between the layers. The device may also comprise a plurality of fluid flow channels that are disposed along the pliable membrane. The fluid flow along the fluid flow channels may be selectively controllable. The fluid flow channels may be coupled to a vacuum source, and the fluid may be removed from the surgical site via the plurality of fluid flow channels when suction or a vacuum is applied.

Certain embodiments include a surgical access device adapted to facilitate access to a surgical site within a body of a patient through an incision in the body. The surgical access device can include a first retention member and a second retention member. The second retention member can be configured to expand from a collapsed configuration to an expanded configuration. The second retention member can include at least four linkages pivotably coupled to one another such that actuation of the linkages causes the linkages to pivot relative to one another thereby radially expanding or collapsing the second retention member. The surgical access device can also include a pliable membrane extending between the first retention member and the second retention member. The pliable membrane can be configured to engage and expand the incision to facilitate access to the surgical site when the second retention member is in the expanded configuration.

In several embodiments, the second retention member is an expandable retention ring and the linkages are pivotably coupled together in a closed shape. The first retention member can be a closed and deformable retention ring. The first retention member can also be a closed and expandable retention ring. The second retention member can include a locking mechanism configured to selectively maintain the second retention member in the expanded configuration. The locking mechanism can comprise ratchet teeth on the second retention member configured to selectively maintain the expanded configuration. The locking mechanism can comprise a ratchet pawl on the second retention member configured to selectively maintain the second retention member in the expanded configuration by engaging at least a portion of the ratchet teeth with the ratchet pawl. Several surgical access device embodiments comprise a release mechanism configured to disengage the ratchet pawl from the ratchet teeth to enable the second retention member to return to the collapsed configuration from the expanded configuration. Some embodiments include a user interface button operatively coupled to at least one of the ratchet teeth or to the ratchet pawl, wherein actuation of the user interface button disengages the ratchet pawl from the ratchet teeth to enable the second retention member to return to the collapsed configuration from the expanded configuration.

In select embodiments, the locking mechanism comprises an indentation and a protrusion. The protrusion can be received in the indentation to selectively lock the second retention member in the expanded configuration.

The pliable membrane can include a tubular membrane that comprises a first end and a second end. The first end can be coupled to the first retention member and the second end can be coupled to the second retention member.

In several embodiments, the first retention member is sized for advancement through the incision into the body. The second retention member can be configured for placement outside the body.

In at least one embodiment, a surgical access device comprises a first retention member and a second retention member having a collapsed configuration and an expanded configuration. The second retention member can comprise at least three linkages pivotably coupled to one another such that expanding the second retention member causes the linkages to pivot relative to each other. The surgical access device can also include a pliable membrane extending between the first retention member and the second retention member. The pliable membrane can be configured to engage and expand the incision to facilitate access to the surgical site when the second retention member is in the expanded configuration.

In some embodiments, the second retention member is biased (e.g., spring loaded) towards the expanded configuration. In other embodiments, the second retention member is biased (e.g., spring loaded) towards the collapsed configuration. In some embodiments, each retention member is a retention ring that is noncircular.

Multiple embodiments include a first retention member and an expandable retention member having an expanded configuration and a collapsed configuration. The expandable retention member can comprise at least four linkages pivotably coupled to one another to form a closed shape, wherein actuation of the linkages causes the linkages to pivot relative to each other thereby expanding the expandable retention member. The embodiments can also include a pliable membrane extending between the first retention member and the expandable retention member, wherein the pliable membrane is adapted to engage tissue and the pliable membrane is configured to expand the incision to facilitate access to the surgical site when the expandable retention member is in the expanded configuration. Several embodiments comprise a radially expandable channel extending axially along the pliable membrane to provide access to the surgical site. Some embodiments include an expandable retention member that comprises at least ten linkages pivotably coupled to one another. Expandable retention members can include a living hinge that pivotably couples at least two of the linkages to one another.

Select embodiments include a first retention member and a second retention member coupled to the first retention member by a connector. The connector can be a pliable membrane, a rigid connector, or any other suitable connector. The first retention member and the second retention member can be configured to expand the incision to provide access to the surgical site. The surgical access embodiment can also include a fluid delivery member coupled to the first retention member and a fluid delivery inlet in fluid communication with the fluid delivery member for introducing fluid into the surgical access system. The system can also include at least one opening in the fluid delivery member, wherein the at least one opening is in fluid communication with the fluid delivery inlet to allow the fluid introduced into the fluid delivery inlet to exit the surgical access system. Several embodiments also include a fluid removal member coupled with at least one of the first retention member, the second retention member, and the connector.

Multiple surgical access embodiments include a first retention member configured for placement within the body at or near the surgical site, a second retention member configured for placement outside the body, and a pliable membrane extending between the first retention member and the second retention member. The embodiments can also include a fluid delivery inlet coupled with the pliable membrane for introducing fluid into the surgical access system and at least one opening in the pliable membrane, wherein the at least one opening is in fluid communication with the fluid delivery inlet to allow the fluid introduced into the fluid delivery inlet to exit the surgical access system. The system can further include a fluid removal member coupled with at least one of the first retention member and the pliable membrane. The fluid removal member can comprise an outlet conduit coupled to a medical suction device.

In several embodiments, the pliable membrane comprises a fluid-permeable material. The surgical access system can be configured to deliver the fluid from the fluid delivery inlet to the fluid-permeable material. The fluid-permeable material can be configured to deliver the fluid to the surgical site. The fluid-permeable material can be a porous medium. The pliable membrane can comprise a circumferential fluid dispersion member.

The pliable membrane can include a fluid-permeable tube. The fluid-permeable tube can be disposed in a spiral direction around the pliable membrane and a wire can be disposed inside at least a portion of the fluid-permeable tube.

Some embodiments include at least one flow regulator in fluid communication with the fluid delivery inlet. A fluid conduit member can be in fluid communication with the fluid delivery inlet. The fluid conduit member can be configured to be placed in fluid communication with a fluid source such as a saline bag. The first retention member and the second retention member are circular in several embodiments.

Several embodiments include a first retention ring, a second retention ring, and a pliable membrane extending between the first retention ring and the second retention ring. The pliable membrane can comprise an inner wall and an outer wall, wherein the pliable membrane comprises a space between at least a portion of the inner wall and the outer wall. The space can be configured to enable fluid to pass through at least a portion of the pliable membrane. A fluid delivery inlet can be coupled with the pliable membrane for introducing the fluid into the surgical access system. The fluid delivery inlet can be in fluid communication with the space. There can be at least one opening in the pliable membrane, wherein the at least one opening is in fluid communication with the space to allow the fluid introduced into the fluid delivery inlet to pass through the space and then exit the surgical access system through the opening. A fluid removal member can be in fluid communication with the pliable membrane. The fluid removal member can comprise an outlet conduit coupled to a medical suction device.

Several embodiments include a method for retracting tissue of a surgical site of a body. The method can include inserting at least a portion of a surgical access device into an incision, wherein the surgical access device comprises a first retention member, a second retention member, a pliable membrane coupled between the first retention member and the second retention member, and a fluid delivery inlet configured to be placed in fluid communication with the pliable membrane. The method can also include advancing the first retention member into the body through the incision and placing the second retention member outside the body. Several embodiments include retracting the tissue using the pliable membrane and introducing fluid into the fluid delivery inlet such that the fluid exits the pliable membrane.

Methods can also include suctioning at least a portion of the fluid into the surgical access device and removing the portion from the body. In select methods, a fluid conduit member is coupled to the first retention member, and the methods further comprise suctioning the fluid into the fluid conduit member and removing the fluid from the body. In some methods, the fluid is an antibiotic fluid, a saline solution, a diagnostic agent, or a therapeutic agent.

Several method embodiments comprise expanding the second retention member, whereby expanding the second retention member causes the pliable membrane to retract the tissue around the incision. The second retention member can comprise at least four linkages pivotably coupled to one another, and expanding the second retention member can comprise pivoting the at least four linkages relative to each other. Expanding can comprise increasing the inner diameter of the second retention member. Some methods include a wire that is spirally wound around the pliable membrane and retracting the tissue comprises pulling the wire. In select methods, retracting the tissue comprises inflating at least a portion of the pliable membrane.

Several method embodiments for retracting tissue of a surgical site of a body comprise inserting at least a portion of a surgical access device into an incision, wherein the surgical access device comprises a first retention member, a second retention member, a pliable membrane coupled between the first retention member and the second retention member, and a fluid removal conduit coupled to the first retention member. The method can further comprise advancing the first retention member into the body through the incision and placing the second retention member outside the body. The method can also comprise retracting the tissue using the pliable membrane, suctioning a fluid into the surgical access device, and removing the fluid from the body. Some methods include introducing fluid into the surgical access device such that the fluid exits the pliable membrane. A suction device can be coupled to the fluid removal conduit.

Multiple methods for retracting tissue of a surgical include inserting a retraction device into an incision, retracting tissue, introducing fluid into the retraction device, and forcing the fluid out of the retraction device into the surgical site. Forcing the fluid out of the retraction device can comprise creating sufficient pressure by positioning the fluid source sufficiently higher than the retraction device or surgical site such that gravity forces the fluid out of the retraction device. Forcing the fluid out of the retraction device can comprise forcing the fluid through a channel system that substantially circumscribes the retraction device. Forcing the fluid out of the retraction device can also include forcing the fluid through a porous material. Various methods also include suctioning the fluid from the surgical site into the retraction device and removing the fluid from the body. The retraction device can include an upper portion and a lower portion that are not in direct fluid communication, wherein forcing the fluid out of the retraction device comprises forcing the fluid out of the upper portion and suctioning the fluid from the surgical site comprises suctioning the fluid into the lower portion.

These and other embodiments are described in further detail in the following description related to the appended drawing figures.

BRIEF DESCRIPTION OF THE DRAWINGS

FIG. 16 is a side view that illustrates an example routing tube orientation angle, according to one embodiment;

FIG. 31b is a top view of a completely collapsed ring that is elliptical, according to one embodiment;

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
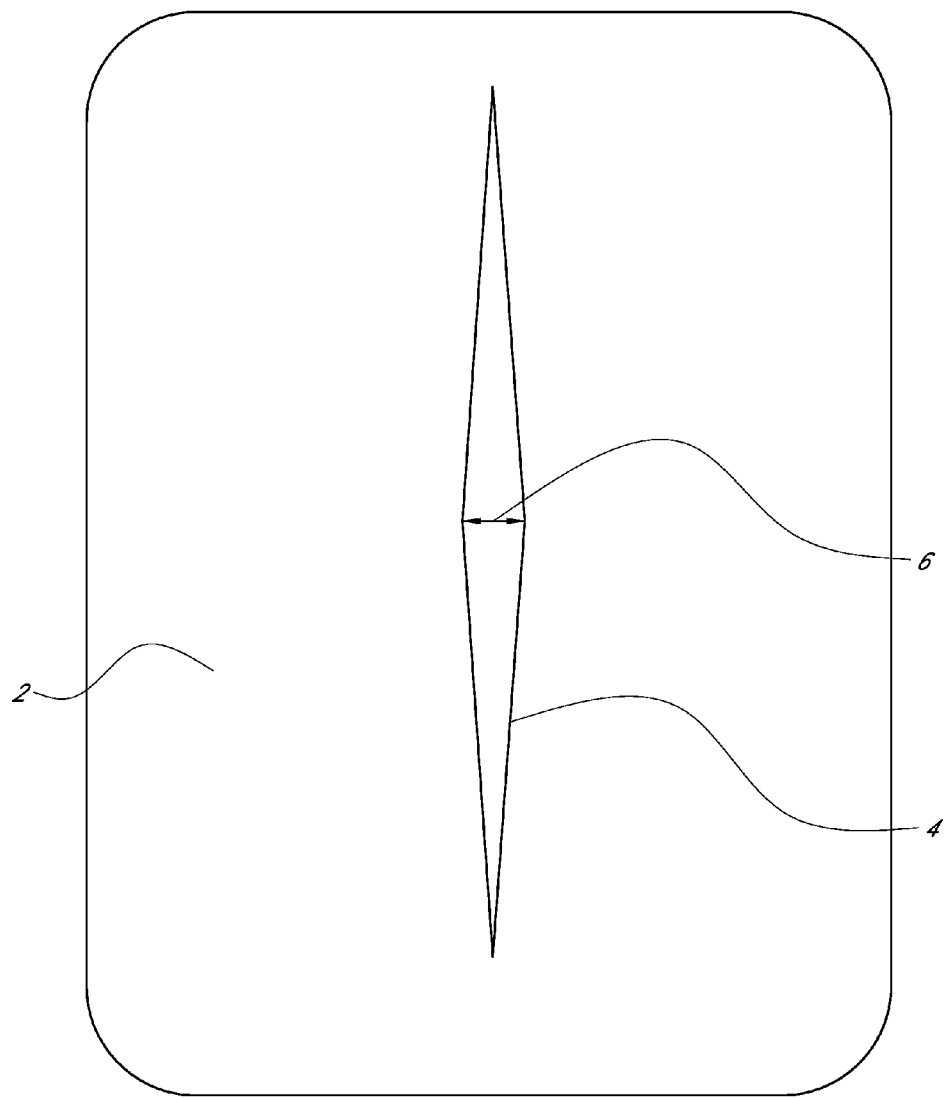
FIG. 1 is a diagrammatic illustration of an incision in a patient's body.
Figure 2:
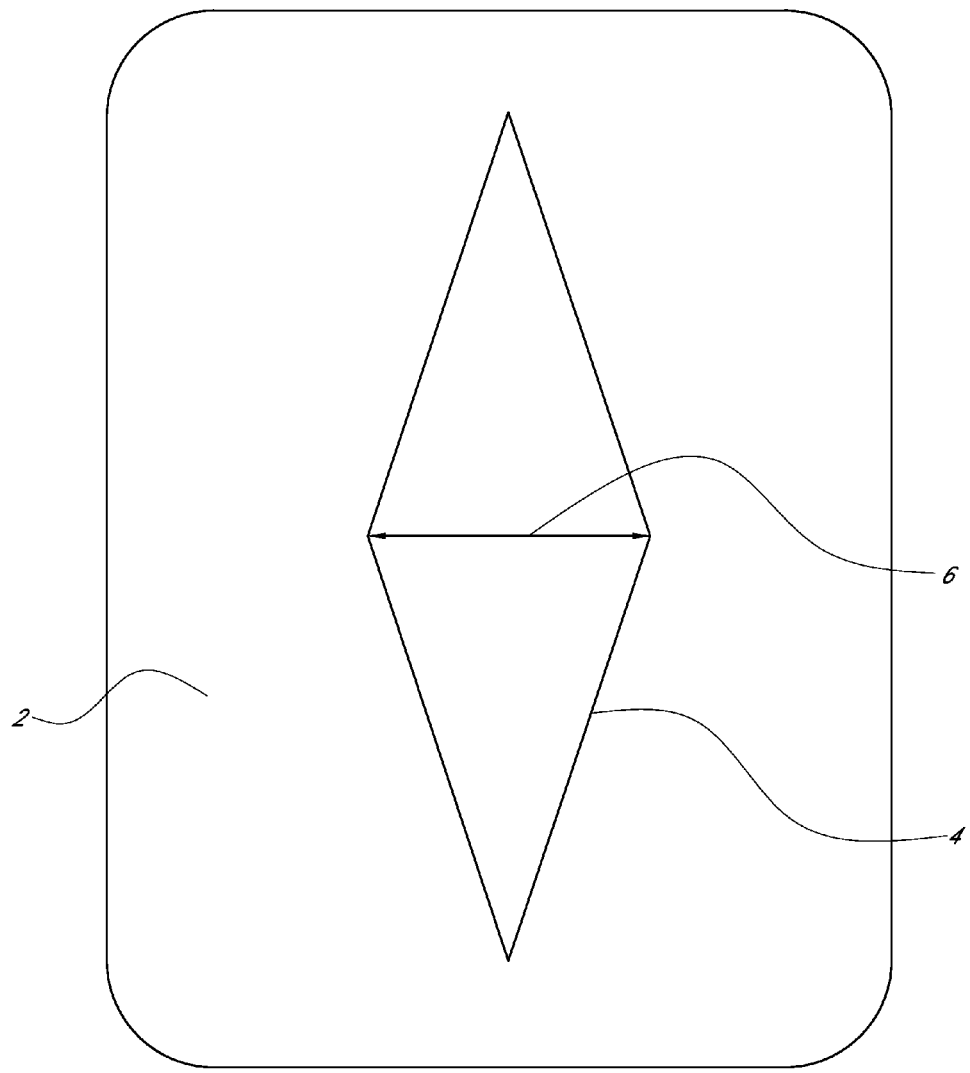
FIG. 2 is a diagrammatic illustration of the incision illustrated in FIG. 1 after the incision has been at least partially expanded.
Figure 3:
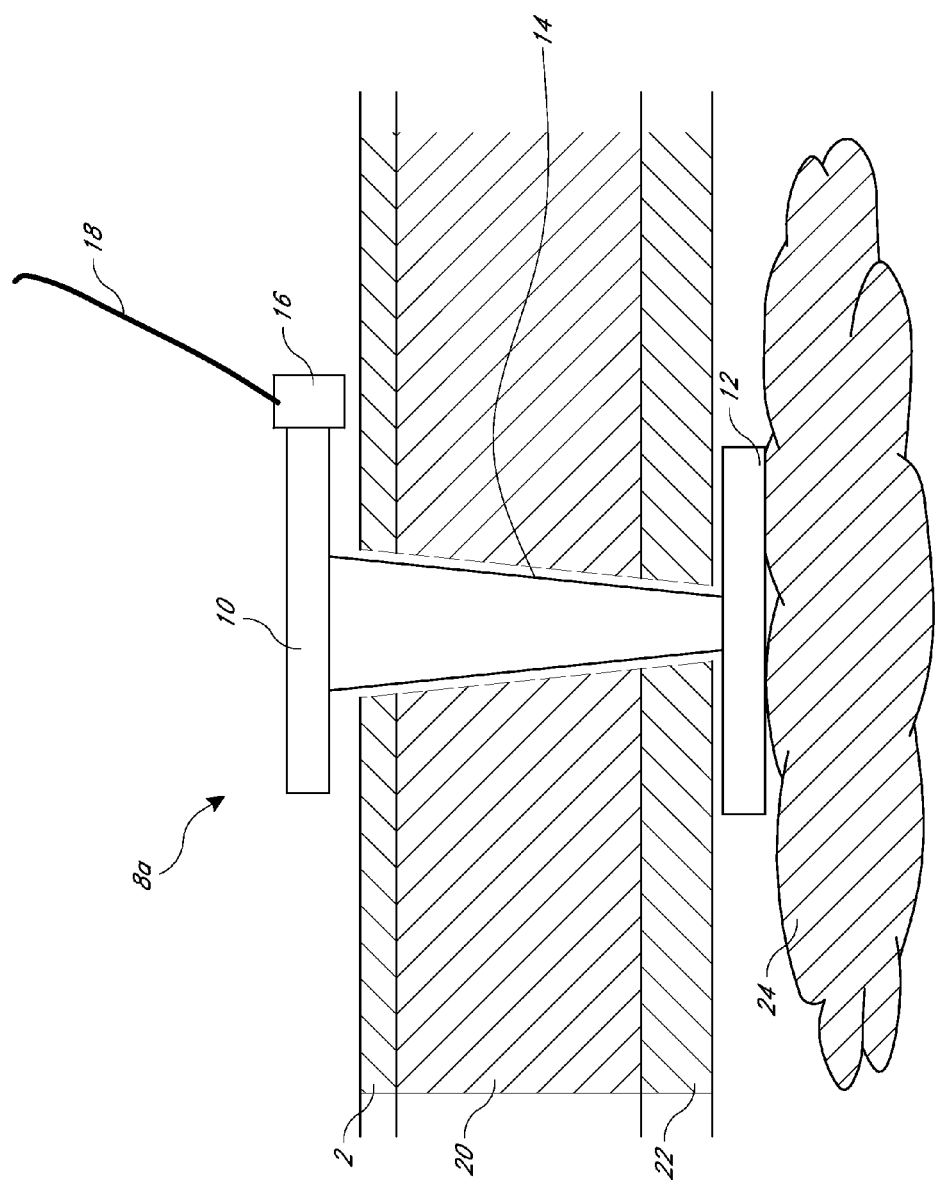
FIG. 3 is a partial cross-sectional view of one embodiment of a surgical access device that is disposed in an incision and provides access to a surgical site.

Referring now to FIGS. 1-3, physicians incise a portion of a patient's body to facilitate access to a surgical site. For example, the surgical site may be deep within the patient's body such that the physician must incise and dissect through the patient's skin 2, subcutaneous tissue, and deep soft tissue (such as fascia and muscle) in order to reach an organ on which the physician needs to operate. Referring now to FIG. 1, incisions 4 are typically too narrow to facilitate access to a surgical site. Surgical access devices 8a often expand the incision 4 to facilitate access to the surgical site. For example, surgical access devices 8a may be wound retractors that retract the tissue around the incision 4 such that the incision width 6 is larger after the surgical access device 8a retracts the tissue than before the surgical access device 8a retracts the tissue. FIG. 2 shows an example of an expanded incision, although expanded incisions may have a wide variety of shapes and sizes. In other embodiments, the surgical access device 8a does not retract the tissue around the incision 4, but generally conforms to the shape of the incision 4 and generally takes the shape of the incised tissue from the skin to the surgical site.

FIG. 3 illustrates one embodiment of a surgical access device 8a that is disposed in an incision and provides access to a surgical site. Exemplary surgical access devices may include surgical retractors that retract the tissue around the incision 4 to form a wider incision width than the initial incision. Other exemplary surgical access devices do not retract tissue or make the incision wider, but deliver fluid to the surgical site and/or remove fluid from the surgical site. In FIG. 3, the patient's body is shown as a cross section while the surgical access device 8a is not shown as a cross sectional view. The surgical access device 8a comprises an upper member 10 and a lower member 12. A sheath 14 extends between the upper member 10 and the lower member 12. In an embodiment, the sheath 14 comprises a tubular membrane that is coupled to the upper member 10 and to the lower member 12. In select embodiments, the upper member 10 and the lower member 12 are retention rings. In other embodiments, the upper member 10 and the lower member 12 are other retention devices such as adhesive straps. A fluid delivery member 16 is coupled to the upper member 10 and a fluid conduit member 18 is placeable in fluid communication with the fluid delivery member 16. The fluid conduit member 18 can be a tube or catheter with one lumen or with multiple lumens. The fluid delivery member 16 can be a tube, a tube with holes, a sponge, a porous medium, and/or another suitable item that can delivery fluid. The sheath 14 can be a pliable membrane, a rigid membrane, or a tube of sufficient diameter to enable access to the surgical site. In one embodiment, the sheath 14 is a plastic, conical tube that is sufficiently rigid to expand the incision. In some embodiments, the fluid conduit member 18 is an inlet conduit member.

FIG. 3 illustrates how the surgical access device 8a provides a path through the skin 2, subcutaneous fat 20, and muscle 22 to facilitate access to an organ 24 on which the physician needs to operate. Fluid can flow through the fluid conduit member 18 to the fluid delivery member 16, which delivers the fluid to one or more parts of the surgical site including, but not limited to, the skin 2, subcutaneous fat 20, muscle 22, and organs 24. The fluid may be comprised of, but is not limited to, saline solution, water, antibiotic solution, solution containing a dye, solution containing radioactive particles, solution containing fluorescent particles, solution containing nanoparticles, solution containing narcotic agents, solution containing analgesic agents, diagnostic agents, therapeutic agents, and/or solution containing immunotherapeutic agents. Some embodiments irrigate with gels and/or pastes. Some embodiments deliver heated fluids that are above room temperature. For example, fluids may be heated using a Level 1® H-1200 Fast Flow Fluid Warmer manufactured by Smiths Medical (Dublin, Ohio). Other embodiments deliver cold fluids that are below room temperature.

As is explained in greater detail below, surgical access devices can comprise a tissue barrier such as a sheath, a flexible conduit, or a pliable membrane. Tissue barriers can come in diverse shapes, sizes, and materials. In some embodiments, a purpose of a tissue barrier is to help irrigate the surgical site by increasing the probability of the irrigating fluid, paste, gel, or substance of being in contact with the desired portions of the surgical site. In some embodiments, a purpose of the tissue barrier is to help retract the tissue.

Figure 4:
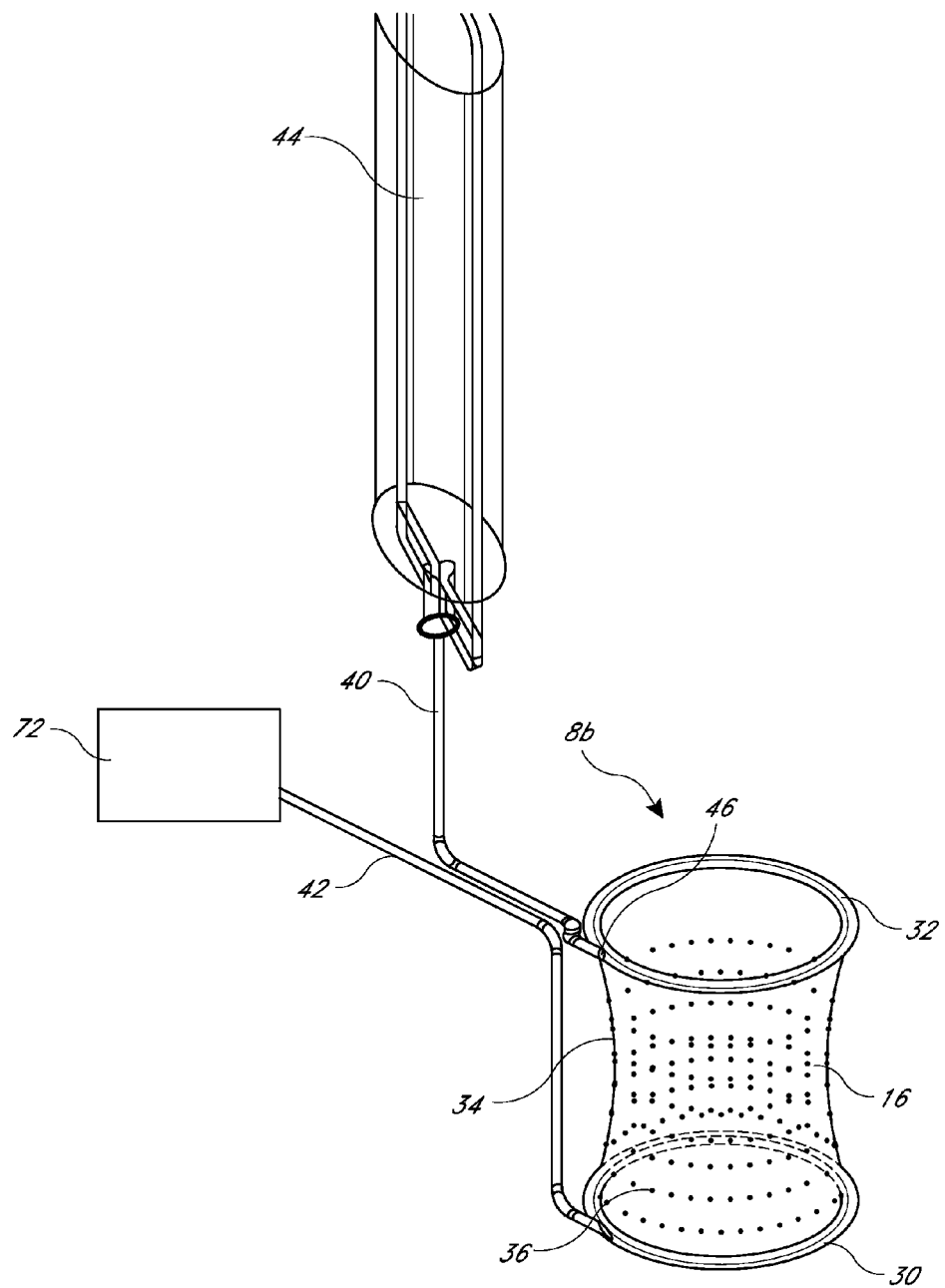
FIG. 4 is a perspective view of an embodiment of a fluid irrigation system in the form of two rings connected by a flexible conduit comprising a plurality of walls.

FIG. 4 illustrates an embodiment of a fluid irrigation system in the form of two rings connected by a flexible conduit comprising a plurality of walls. The fluid delivery member 16 comprises a pliable membrane 34 with perforations 36. The perforations 36 can be arranged in any suitable manner. In one embodiment, the perforations 36 are evenly spaced apart to irrigate the entire surgical site. In another embodiment, the perforations 36 are generally clustered towards the second retention ring 32 such that the fluid drips down the walls of the surgical site. The perforations 36 make the pliable membrane 34 a fluid-permeable material. Not all of the perforations 36 in FIG. 4 are labeled in order to make the illustration less cluttered and easier to see. The perforations 36 are illustrated as small, black dots in FIG. 4. The plurality of walls can be heat sealed together in select portions.

The pliable membrane 34 can be any tissue barrier that is at least partially flexible or is at least partially conformable under normal tissue retracting conditions. Pliable membranes 34 can come in many shapes and thicknesses. In one embodiment, the pliable membrane 34 is one inch thick. In other embodiments, the pliable membrane 34 is less than 0.01 inch thick. In some embodiments, the pliable membrane 34 forms a tube. In other embodiments, the pliable membrane 34 is not tubular, but is shaped like a flat sheet.

In some embodiments, the pliable membrane 34 includes seals to prevent billowing of the structure. Preventing billowing helps provide reliable access to the surgical site.

In this embodiment, the surgical access device 8b comprises a first retention ring 30 that is coupled to a second retention ring 32 by a flexible conduit or pliable membrane 34. In the illustrated embodiment, the pliable membrane 34 is a tubular membrane, the first retention ring 30 is circular, and the second retention ring 32 is circular. Tubular membranes can have many cross sectional shapes including, but not limited to, cross sections that are square, diamond, parallelogram, rectangular, triangular, pentagonal, hexagonal, and elliptical.

The second retention ring can be attached to a frame such as a Bookwalter retractor made by Codman & Shurtleff, Inc. (a Johnson & Johnson company). Attaching the second retention ring to a frame can provide the mechanical rigidity necessary in some embodiments to expand the incision.

In some embodiments, the pliable membrane 34 includes at least two perforations 36 or holes. The perforations may have many shapes including, but not limited to, round, triangular, and rectangular. In some embodiments, the perforations are different sizes. For example, the perforations 36 located within one inch of the second retention ring 32 may be 25 to 200% larger in cross-sectional area than the perforations 36 located 1.5 to 10 inches from the second retention ring 32 to provide a more even flow or to provide a biased flow. In one embodiment, the pliable membrane has at least ten perforations 36 but less than 125 perforations 36. In another embodiment, the pliable membrane 34 has at least 125 perforations 36 but less than 500 perforations 36. The perforations may be located in a sinusoidal pattern, a zigzag pattern, or in a straight line.

The interior surface of the pliable membrane 34 permits access to the surgical field with the hand or other instruments (e.g., robots, laparoscopic instruments, retractors, tissue sealing devices). The illustrated embodiment comprises a fluid source 44, which may be a bag or container that holds a fluid. An inlet conduit 40 places at least a portion of the surgical access device 8b in fluid communication with the fluid source 44. The inlet conduit 40 may be an inlet tube. An outlet conduit 42 is in fluid communication with at least a portion of the surgical access device 8b. The outlet conduit 42 may be an outlet tube.

In one embodiment, the second retention ring 32 comprises an inlet conduit such as a fluid delivery inlet 46. Gravity can typically drive the fluid through the system, although some embodiments utilize a pump or other pressure source. In one embodiment, an outlet conduit of the first retention ring 30 is in fluid communication with the inlet conduit 40 via space formed between two generally concentric flexible walls.

Figure 5:
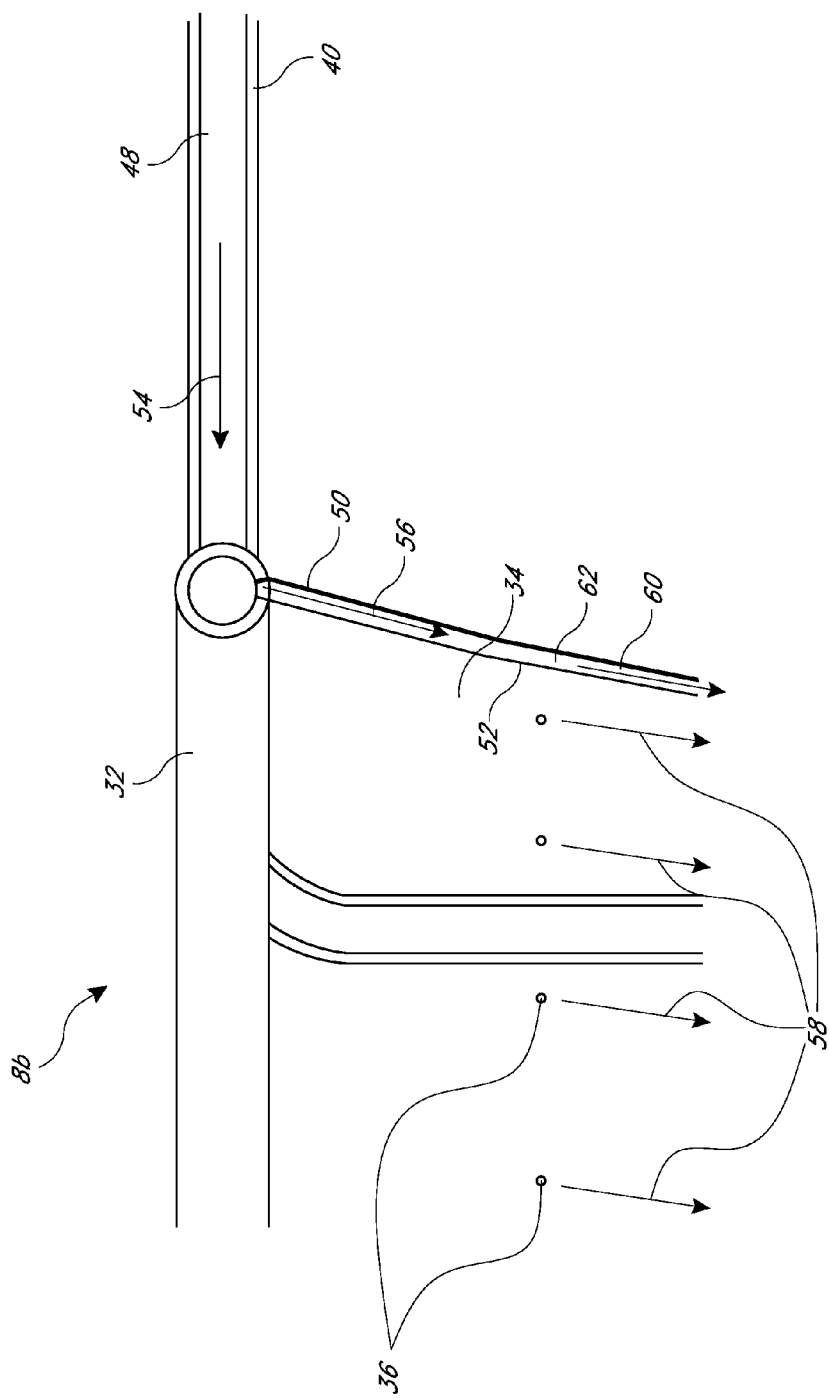
FIG. 5 is a cross-sectional view of an inlet conduit, pliable membrane, and second retention ring, according to one embodiment.

FIG. 5 provides a cross-sectional view through the inlet conduit 40, pliable membrane 34, and second retention ring 32. Fluid 48 entering the second retention ring 32 by means of the inlet conduit 40 is directed between an inner wall 50 and an outer wall 52 of the pliable membrane 34. The outer wall 52, which is configured to be in contact with tissue in the wound, comprises a plurality of perforations 36 configured to deliver at least a portion of the fluid 48 to the tissue in or near the surgical site. In this manner, fluid, such as antibiotic fluid, saline solution, or other fluid, is delivered to wound tissues. In various embodiments, the perforations are less than 0.25 mm, between 0.15 mm and 0.35 mm, between 0.25 mm and 0.50 mm, or between 0.5 mm and 1.5 mm. The space 62 between the inner wall 50 and the outer wall 52 enables fluid to pass between at least a portion of the inner wall 50 and the outer wall 52. Thus, the fluid can travel in the space 62 through at least a portion of the pliable membrane 34 before the fluid exits the surgical access system. In one embodiment, the space 62 is filled with a porous material and the inner wall 50 and the outer wall 52 are nonporous materials.

Select embodiments include a pliable membrane 34 with a coating. In order to enhance the ability of the surgical access device 8c to deliver fluid to the surgical access site including, but not limited to skin 2, subcutaneous fat 20, muscle 22, and organs 24, the pliable membrane 34 can be provided with a hydrophilic coating, such as the Hydak® hydrophilic coating provided by Biocoat, Inc., to encourage fluid dispersion along its surface. The coating can be applied to one or both sides of outer wall 52. The coating can also be applied to the inner wall 50. A coating on a surface that defines the boundary of the space 62 can enhance fluid dispersion throughout the space 62. Enhanced fluid dispersion can increase the number of the perforations 36 through which fluid flows to irrigate the surgical site. The coating on an outer surface of the outer wall 52 can enhance the fluid dispersion along the exterior of the surgical access device 8c and, therefore, enhance the fluid delivery to the surgical access site.

In one embodiment, the fluid 48 has at least three flow stages. In a first flow stage 54, the fluid 48 flows through the inlet conduit 48. In a second flow stage 56, a least a portion of the fluid 48 flows between the inner wall 50 and the outer wall 52. In a third flow stage 58, at least a portion of the fluid 48 flows through the perforations 36 in route to surgical site tissue. Another embodiment includes a fourth flow stage 60, in which at least a portion of the fluid 48 flows past the perforations 36 in route to more distally located perforations and/or to other features that are located closer than the perforations 36 to the first retention ring 30.

In another embodiment, the inlet conduit 40 is not in fluid communication with the second retention ring 32, but the inlet conduit 40 is in fluid communication with the pliable membrane 34.

Figure 6:
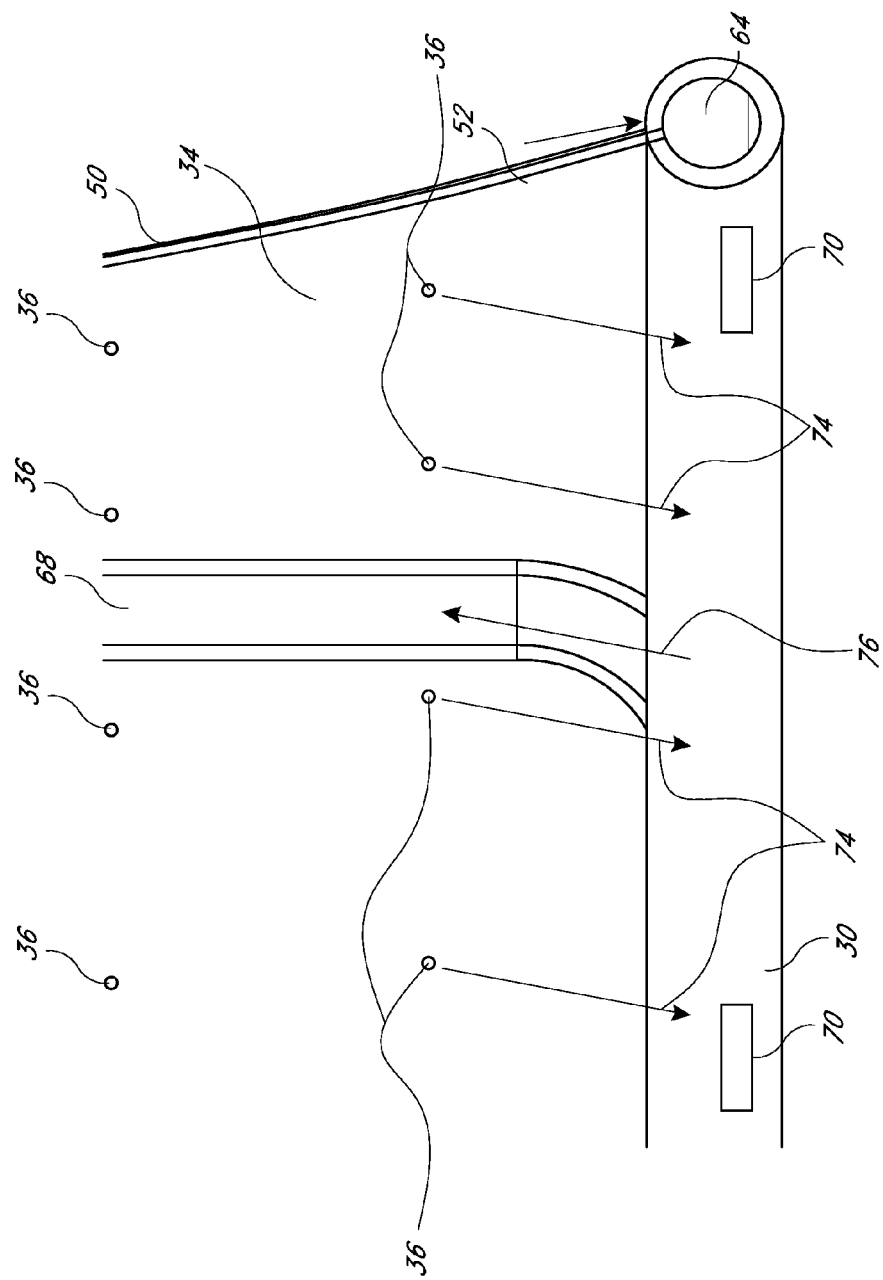
FIG. 6 is a cross-sectional view of a pliable membrane and first retention ring, according to one embodiment.

FIG. 6 provides a cross-sectional view through the pliable membrane 34 and first retention ring 30. In an embodiment, the first retention ring 30 comprises a hollow ring 64 and a fluid removal conduit 68 is in fluid communication with the hollow ring 64. The fluid removal conduit 68 may be placed in fluid communication with the outlet conduit 42, which may be connected to a medical suction device 72 (see FIG. 4), pump, or vacuum such that the outlet conduit 42 is a suction tube. The medical suction device 72 creates a pressure that is lower than atmospheric pressure to remove fluid from the surgical site. The fluid removal conduit 68 may be a tube, a channel, or any other suitable conduit.

The first retention ring 30 may include a ring opening 70 into which the medical suction device 72 may suck fluid 48 (not shown in FIG. 6) or bodily fluids from the surgical site. The first retention ring 30 may be configured to collect fluid from the wound for drainage purposes. In another embodiment, the pliable membrane 34 is configured to collect fluid from the wound for drainage purposes. For example, the pliable membrane 34 may have pores or perforations that are in fluid communication with the medical suction device 72. Thus, the system can remove fluid by pulling the fluid into the pliable membrane and out the outlet conduit 42.

In one embodiment, at least a portion of the inner wall 50 and at least a portion of the outer wall 52 are fused together near the distal end of the pliable membrane 34. This embodiment may prevent direct fluid flow from the inlet conduit 40 to the outlet conduit 42 by forcing the fluid 48 to flow out of the surgical access device 8b before going back into the surgical access device 8b for removal from the patient's body.

In another embodiment, the fluid flow comprises two stages. In the flow exit stage 74, the fluid 48 exits the surgical access device 8b and irrigates at least a portion of the surgical site. In the flow removal stage 76, the fluid 48 and bodily fluid are drawn into the surgical access device 8b, travel generally proximally in the fluid removal conduit 68, and are removed from the patient's body.

Figure 7:
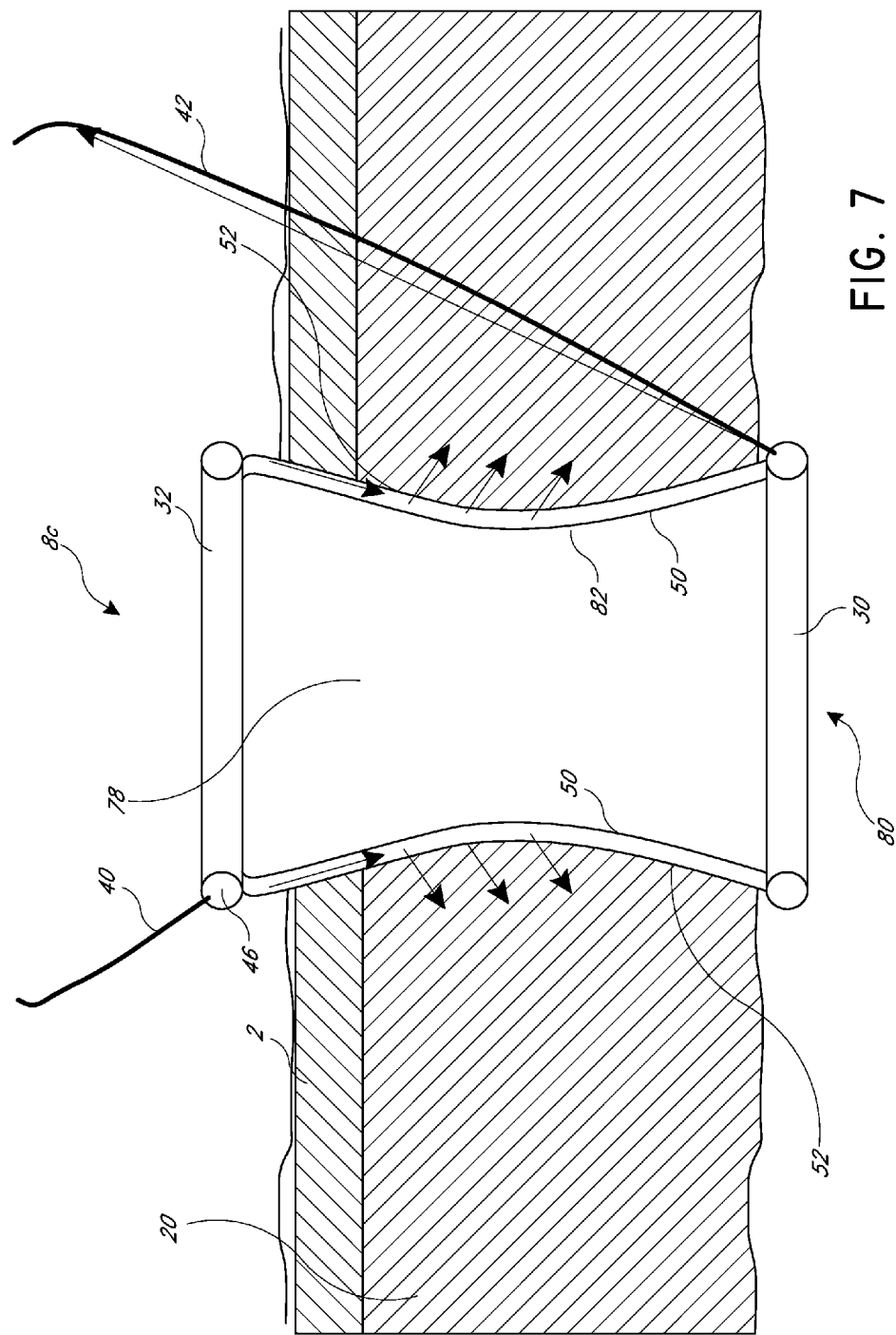
FIG. 7 is a cross-sectional view that illustrates how a surgical access device provides access through skin and subcutaneous fat in route to a target site, according to one embodiment.

FIG. 7 illustrates how a surgical access device 8c provides access through skin 2 and subcutaneous fat 20 in route to a target site 80. The target site 80 can be any site on which the physician desires to operate. In this embodiment, the outlet conduit 42 is coupled to a distal portion of the surgical access device 8c. The distal portion to which the outlet conduit 42 is coupled may be the first retention ring 30 or may be a distal portion of a sheath 82.

In an embodiment, the sheath 82 is a pliable membrane. In another embodiment, the sheath is not a pliable membrane. The fluid 48 (not shown) may enter the fluid delivery inlet 46, exit the sheath 82, and irrigate the wound. The surgical access device 8c may irrigate any tissue, including but not limited to skin, subcutaneous tissue, subcutaneous fat, fascia, muscle, organs, or any other part of the patient's body. After irrigating the wound, fluid collected in the surgical site may be removed through the outlet conduit 42.

In another embodiment, the sheath 82 includes an inner wall 50 and an outer wall 52. In another embodiment, the sheath is made of a single material such as a sponge. In various embodiments, the sponge material is Rayon®, polyester, or cotton.

Figure 8:
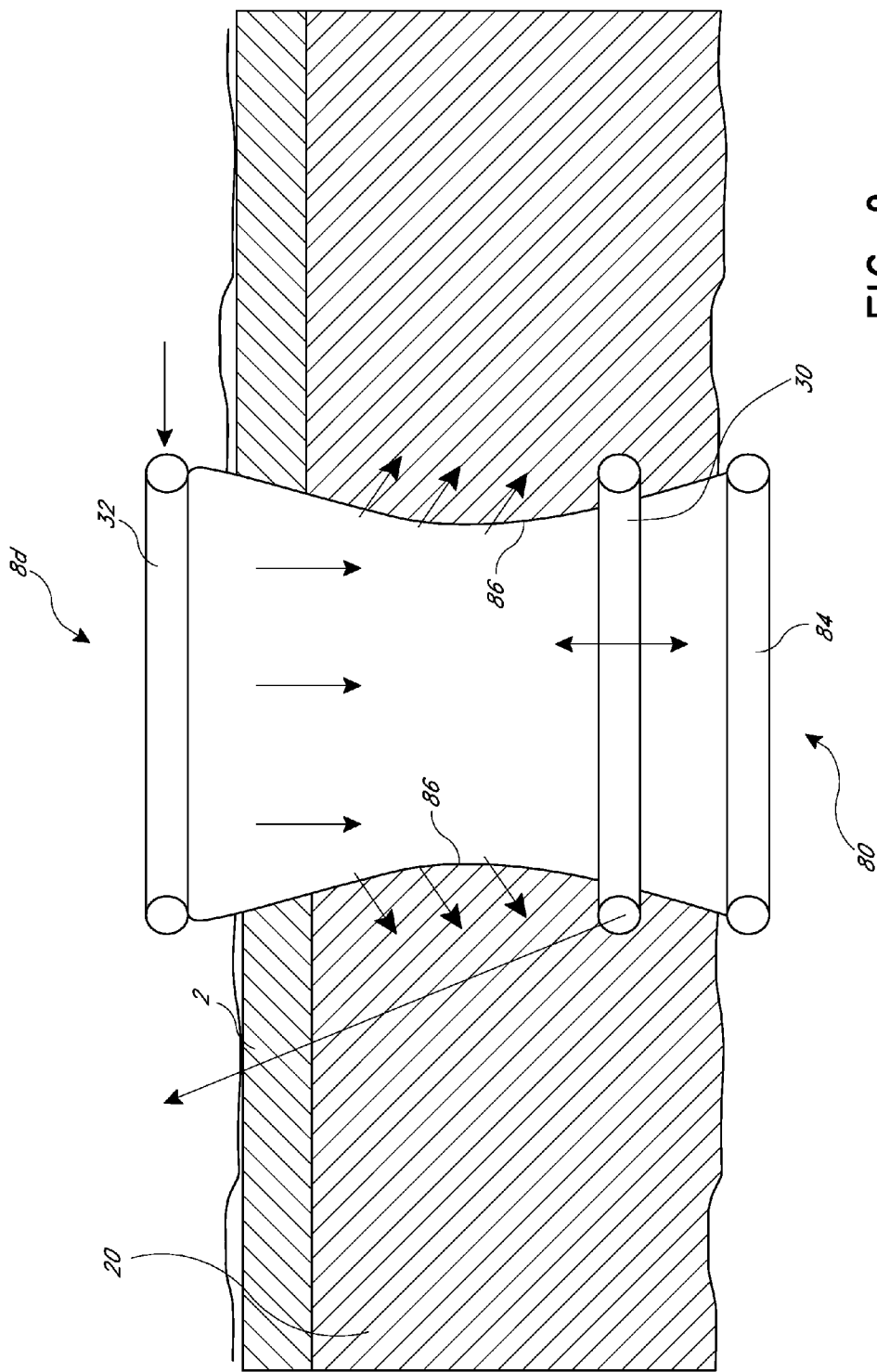
FIG. 8 is a cross-sectional view that illustrates an embodiment that comprises a third retention ring.

FIG. 8 illustrates an embodiment which comprises a third retention ring 84. In one embodiment, the third retention ring 84 is coupled to the sheath 82 and is part of a surgical access device 8d. In this embodiment, the first retention ring 30 is used to remove fluid. In another embodiment, the third retention ring 84 is used to remove fluid. A tissue barrier 86 generally holds the incision 4 open to provide surgical access. The tissue barrier 86 may be plastic, rubber, metal, or any other suitable material. In one embodiment, the tissue barrier is titanium. In various embodiments, the tissue barrier is polytetrafluoroethylene (PTFE), expanded polytetrafluoroethylene (ePTFE), polyurethane, or medical-grade silicone.

Figure 9C:
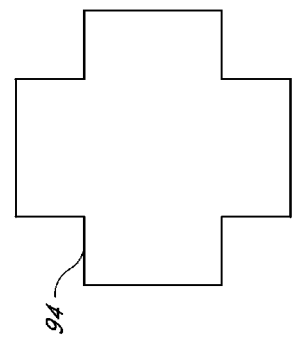
FIGS. 9a-9d illustrate top views of various retention ring embodiments with different shapes.
Figure 9D:
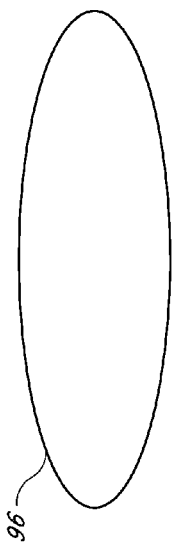
Figure 9A:
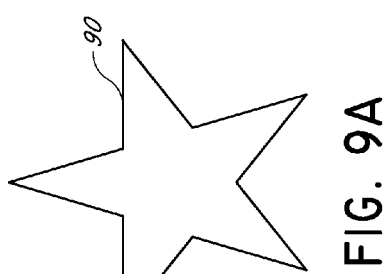
Figure 9B:
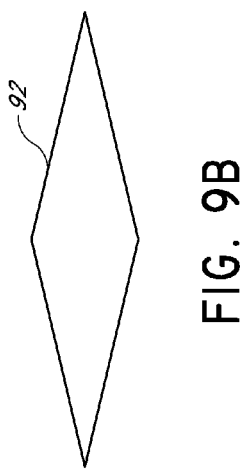

Although FIG. 4 illustrates circular retention rings, retention rings can be many diverse shapes. For example, FIGS. 9a-9d illustrate various retention ring embodiments that can be coupled to pliable membranes, sheaths, and tissue barriers. The retention ring embodiments illustrated in FIGS. 9a-9d are examples of closed shapes. FIG. 9a illustrates a star-shaped retention ring 90. FIG. 9b illustrates a diamond-shaped retention ring 92. FIG. 9c illustrates a cross-shaped retention ring 94. FIG. 9d illustrates an elliptical retention ring 96. A surgical access system can have retention rings with different shapes. For example, a surgical access system can have a circular retention ring and a square retention ring. Any of the embodiments described herein may employ any of the shapes in FIGS. 9a-9d.

Figure 10:
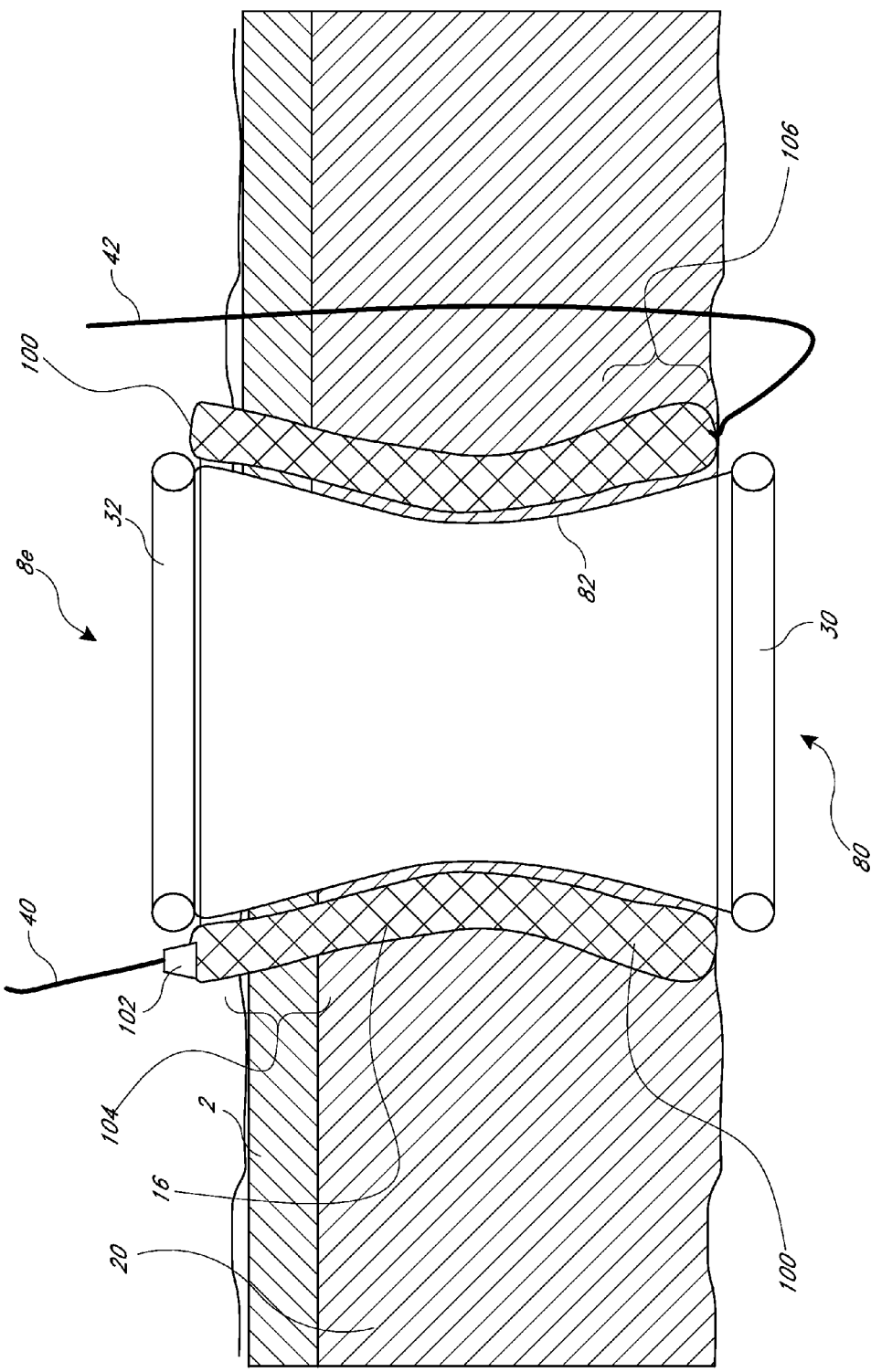
FIG. 10 is a cross-sectional view that illustrates a surgical access device wherein the fluid delivery member comprises a porous medium, according to one embodiment.

FIG. 10 illustrates a surgical access device 8e wherein the fluid delivery member 16 comprises a porous medium 100. The porous medium 100 is an example of a fluid-permeable material. The porous medium 100 can be any material with pores large enough that liquid water can pass through the material with an input pressure equal to a one meter column of water in normal atmospheric conditions at room temperature. The porous medium 100 can also be any material through which liquid water can be pumped. In various embodiments, the porous medium is a sponge. In the embodiment illustrated in FIG. 10, the pliable membrane comprises a sheath 82 and a porous medium 100. The porous medium 100 is located on the exterior of the surgical access device 8e to enable the porous medium 100 to touch tissue in the surgical site. The sheath 82 lines the interior of a surgical access channel. In another embodiment, a substantial portion of the pliable membrane consists of a porous medium and the pliable membrane does not necessarily comprise a sheath or additional tissue barrier.

Several embodiments of surgical access devices reduce SSI by irrigating the surgical site with a fluid that reduces infection. Irrigation can be directed to the surgical site such that fluid contacts the tissue in a way that makes an infection less likely.

Fluid 48 may flow to the surgical access device 8e via the inlet conduit 40, which may be in fluid communication with a fluid reservoir such as a bag or syringe that contains fluid. The inlet conduit 40 may be a tube that is coupled to a fluid delivery inlet port 102. The inlet port fluidly couples the inlet conduit 40 to the surgical access device 8e. In the embodiment illustrated in FIG. 10, the inlet conduit 40 is in fluid communication with a pliable membrane. The inlet port 102 fluidly couples the inlet conduit 40 to the porous medium 100.

The outlet conduit 42 is in fluid communication with the porous membrane 100 such that fluids flow from the surgical site into the porous medium 100 and out of the patient through the outlet conduit 42, which may be a rubber tube or a flexible plastic tube. In various embodiments, the inlet conduit 40 and the outlet conduit 42 are detachable from the surgical access device 8e.

As illustrated in FIG. 10, the pliable membrane comprises a tubular membrane. The tubular membrane comprises an upper portion 104 and a lower portion 106. The lower portion 106 is closer than the upper portion 104 to the first retention ring 30. A first fluid conduit member, illustrated as inlet conduit 40, is in fluid communication with the upper portion 104. A second fluid conduit member, illustrated as outlet conduit 42, is in fluid communication with the lower portion 106. In one embodiment, the upper portion 104 is not in direct fluid communication with the lower portion 106 such that fluid from the first fluid conduit cannot flow to the second fluid conduit without exiting the surgical access device and then reentering the surgical access device. The user forces the fluid out of the upper portion 104 into the surgical site by applying sufficient pressure to the fluid such that the fluid flows out of the upper portion 104 and into the surgical site. In many embodiments, gravity provides sufficient pressure to cause the fluid to flow into the surgical site.

In another embodiment, the upper portion 104 is not in substantially direct fluid communication with the lower portion 106 such that the majority of fluid from the first fluid conduit cannot flow to the second fluid conduit without exiting the surgical access device and then reentering the surgical access device.

Figure 11:
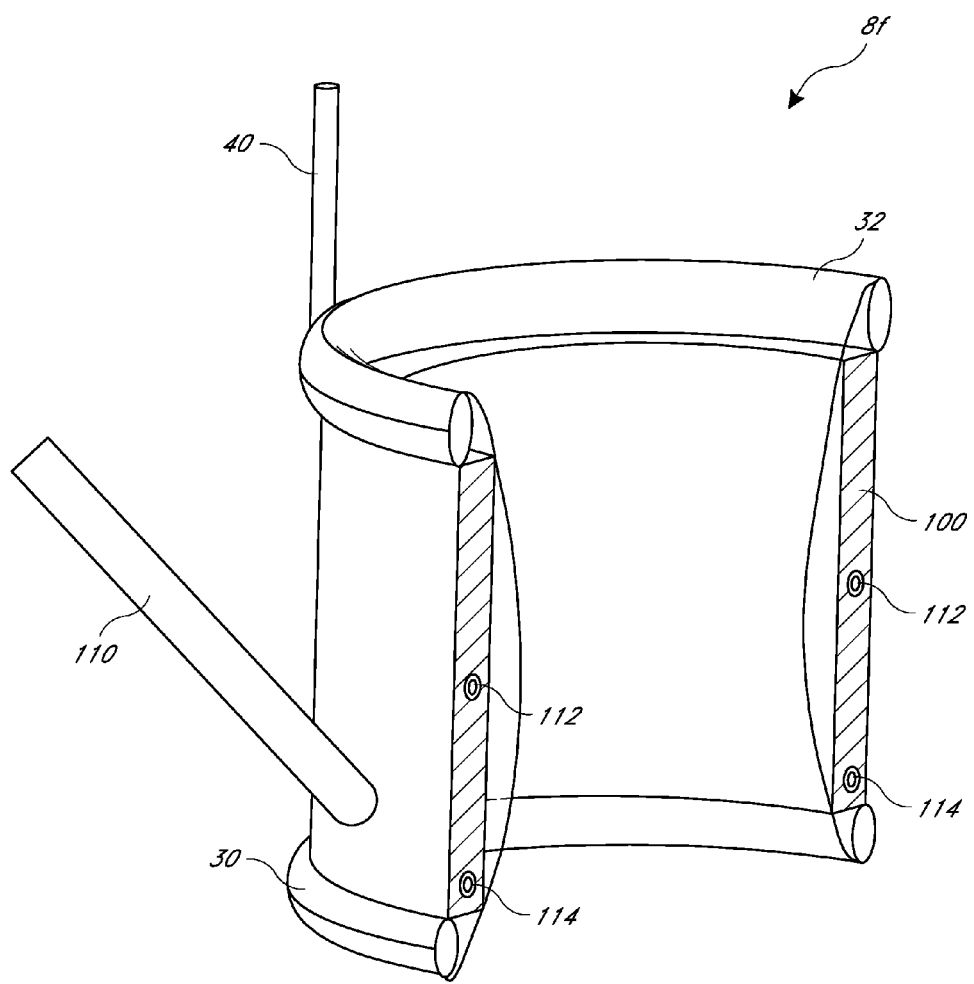
FIG. 11 is a cross-sectional view that illustrates a surgical access device wherein the fluid delivery member comprises a porous medium, according to one embodiment.

FIG. 11 illustrates an embodiment of a surgical access device 8f. A porous medium 100, such as a diffusion sponge or foam, prophylactically doses the subcutaneous tissue in antibiotic solution to defend against microbial invasion both during surgery and after surgery. The porous medium 100 can be open cell foam. Fluid may be fed into the surgical access device 8f via gravity. A circumferential infusion channel system 112 is embedded within the porous medium to enable uniform perfusion rates. The channel system 112 may include multiple channels that together provide the necessary fluid pathways. For example, one channel may wrap 180 degrees around the perimeter and another channel may wrap another 180 degrees around the perimeter such that together the channels form a system that wraps all the way around the perimeter. A circumferential vacuum channel 114 is placed in fluid communication with a suction tube 110. The suction tube 110 is connected to medical suction to remove fluid from the surgical site. In another embodiment, the suction tube 110 is fluidly coupled to a surgical access device that does not have a circumferential suction channel 114.

The circumferential suction channel 114 may be located proximally to the first retention ring 30 and distally to the circumferential infusion channel system 112. This configuration allows gravity to generally pull fluid from the inlet conduit 40 to the suction tube 110. In various embodiments, the fluid removal means is located near the distal end of a surgical access device to reduce instances of unwanted fluid pooling in the surgical site.

In several embodiments, the fluid removal system is positioned in a manner that is highly effective at removing unwanted fluid, which can increase surgical site visibility. Increasing surgical site visibility can improve patient outcomes by enabling more precise surgery and can reduce procedure times, which can lower the probability of SSI.

In another embodiment, a surgical access device comprises a first retention ring, a second retention ring, and a porous medium that extends between the first retention ring and the second retention ring. The porous medium is impregnated or soaked with chemical or biological means to prevent infection before the porous medium is inserted into the surgical site.

Figure 12:
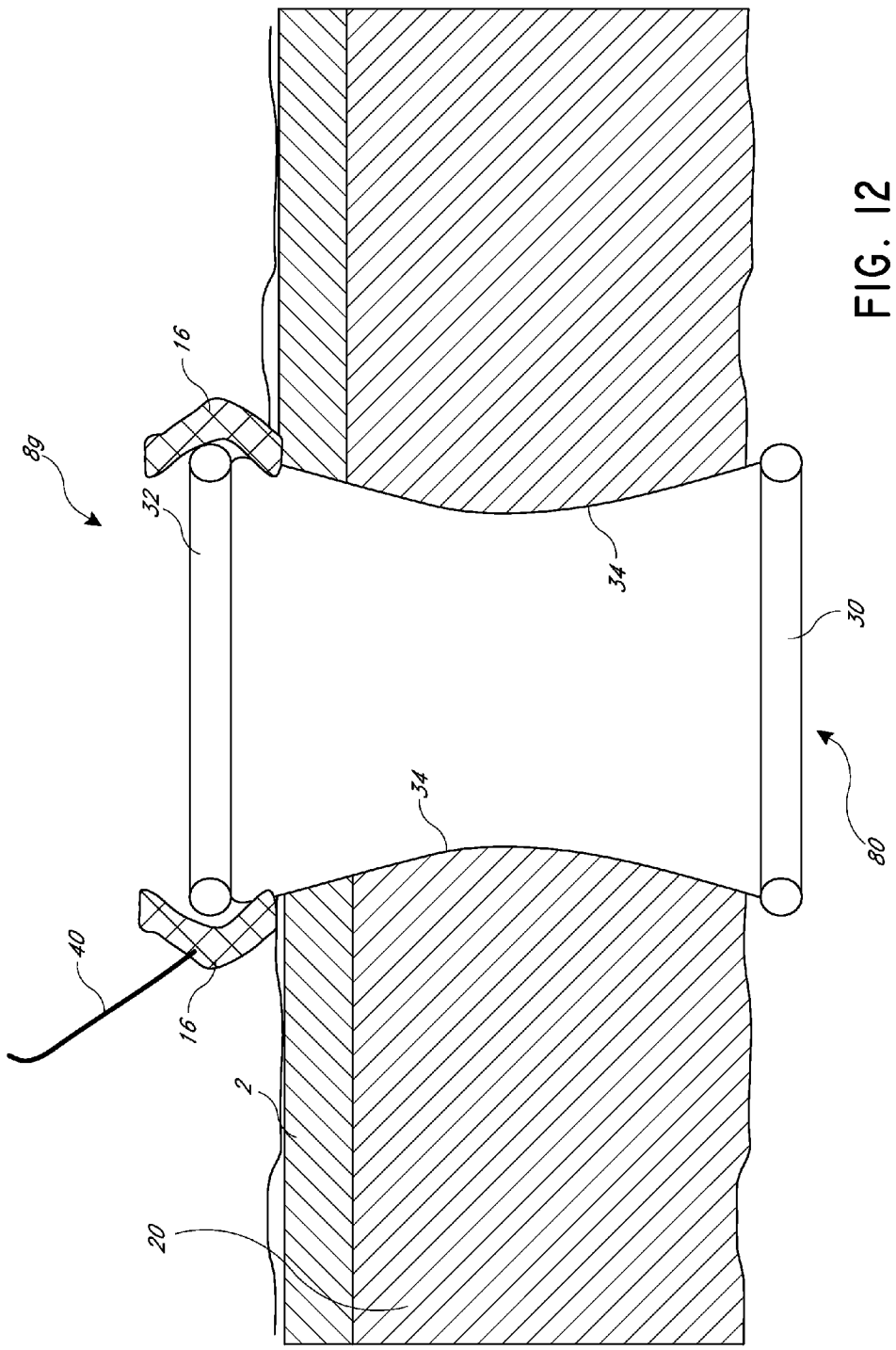
FIG. 12 is a cross-sectional view of an embodiment in which the fluid delivery member is located near the proximal end of a surgical access device.

FIG. 12 illustrates an embodiment in which the fluid delivery member 16 is located near the proximal end of a surgical access device 8g. This configuration uses gravity to distribute fluid down through the surgical site. For example, fluid that exits the fluid delivery member 16 in the subcutaneous fat layer could drip down to a target site, such as an abdominal cavity. In one embodiment, the fluid delivery member 16 is connected to the second retention ring 32. In another embodiment, the fluid delivery member 16 is integrated into the second retention ring 32.

The fluid delivery member 16 in FIG. 12 is a circumferential fluid dispersion ring. A circumferential fluid dispersion ring may wrap around a portion of the surgical access device 8g and may be located on the surgical access device 8g such that is does not rely on gravity to distribute fluid to the surgical site.

Figure 13:
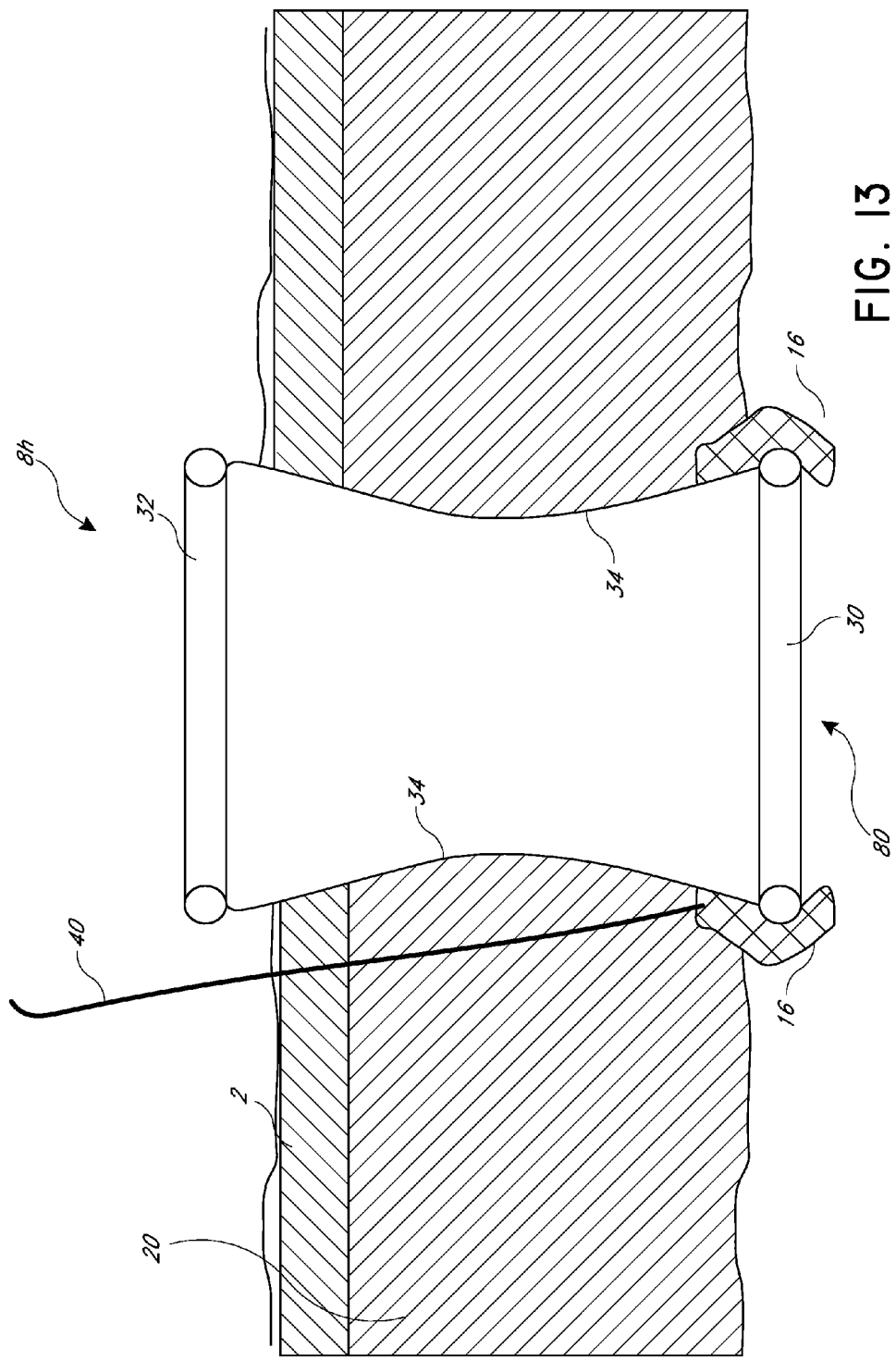
FIG. 13 is a cross-sectional view of an embodiment in which the fluid delivery member is located near the distal end of a surgical access device.

FIG. 13 illustrates an embodiment in which the fluid delivery member 16 is located near the distal end of a surgical access device 8h. This embodiment can be used to remove fluid through the fluid delivery member 16. For example, the inlet conduit 40 can be placed in fluid communication with the fluid delivery member 16 and a medical suction device 72 (see FIG. 4). Thus, the medical suction device 72 can suck fluid from the surgical site into the fluid delivery member 16, through the inlet conduit 40, and out of the patient's body. In one embodiment, a surgical access device removes fluid from the surgical site, but does not irrigate the surgical site.

In various embodiments, the fluid delivery member 16 is placed within 10 mm, 20 mm, 30 mm, or 50 mm of the distal end of the surgical access device 8h. The fluid delivery member 16 may be a foam or sponge. In one embodiment, the fluid delivery member 16 is connected to the first retention ring 30. In another embodiment, the fluid delivery member 16 is integrated into the first retention ring 30.

Figure 14:
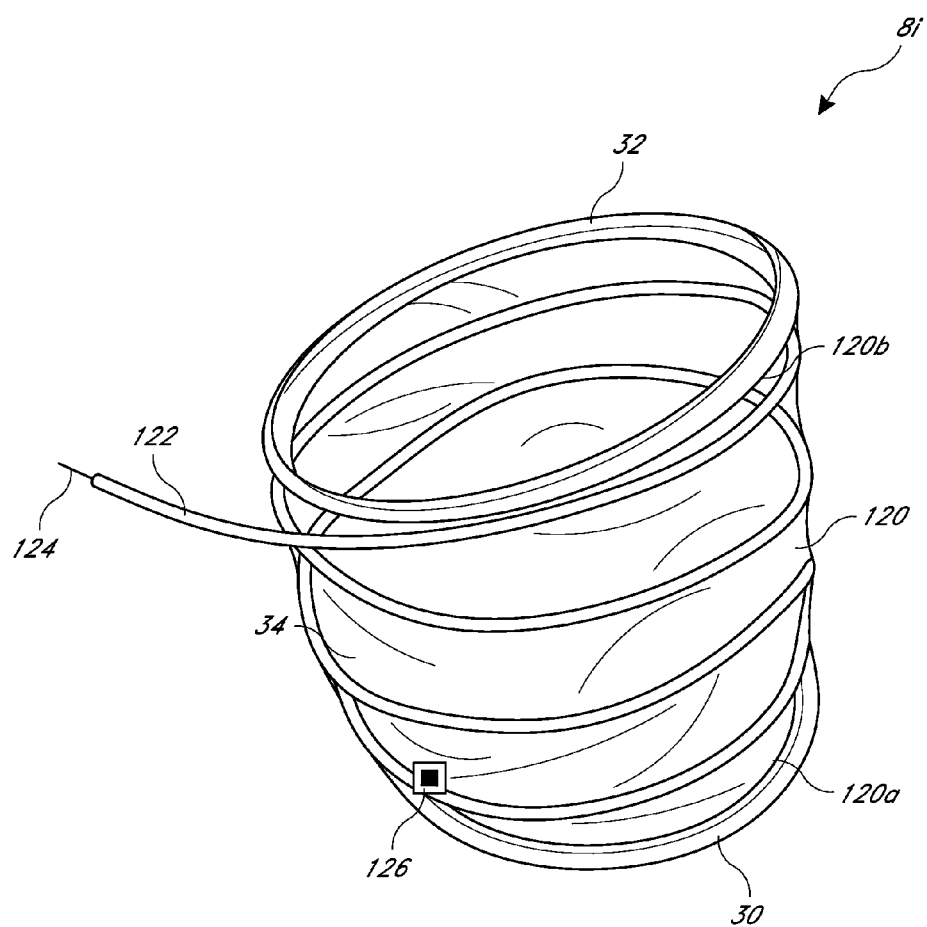
FIG. 14 is a perspective view of an embodiment in which a pliable membrane comprises a tubular membrane and a routing tube with at least one lumen.

FIG. 14 illustrates an embodiment in which the pliable membrane 34 comprises a tubular membrane 120 and a routing tube 122 with at least one lumen. The routing tube 122 is disposed in a spiral direction around the tubular membrane 120. The tubular membrane 120 comprises a first end 120a and a second end 120b. The first end 120a is coupled to the first retention ring 30. The second end 120b is coupled to the second retention ring 32. The routing tube 122 may be adhesively bonded to the tubular membrane 120. In one embodiment, the routing tube 122 is chemically bonded to the tubular membrane 120.

In another embodiment, the routing tube 122 is disposed in a helical direction around the tubular membrane 120. For the purposes of this application, spiral directions include helical directions.

The surgical access system 8i illustrated in FIG. 14 comprises a wire 124 disposed inside at least a portion of the routing tube. The surgical access device 8i may have an anchor 126 or point at which the wire 124 is anchored to the surgical access device 8i. The wire 124 is generally slideably disposed inside the routing tube 122 except for at one or more anchor points or attachment points. In one embodiment, the wire 124 is anchored near its distal end. Pulling on the proximal end of the wire 124 imparts a straightening force on the generally curved routing tube 122. Thus, pulling the wire causes the tissue to retract around the incision by increasing the rigidity of the tubular membrane 120. The pliable membrane 34 may be a polyurethane sheath that acts as a barrier to tissue in the surgical site.

Figure 15A:
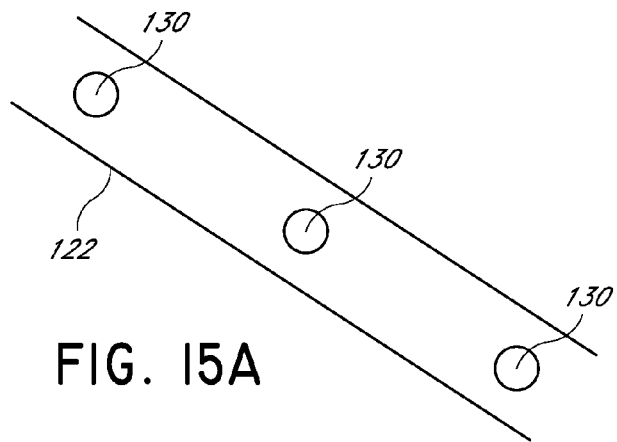
FIGS. 15a-15c illustrate embodiments of holes, slits, and spiral slots in various routing tubes.
Figure 15B:
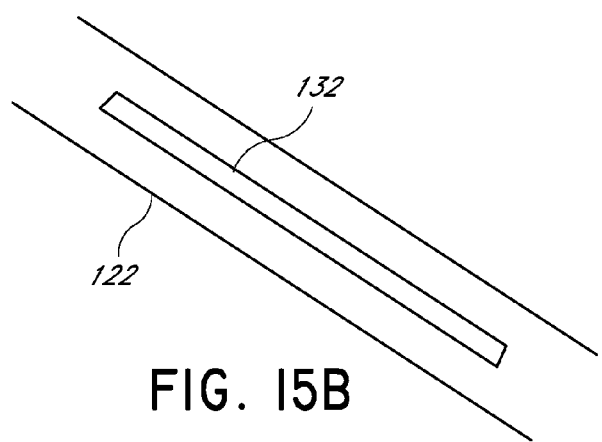
Figure 15C:
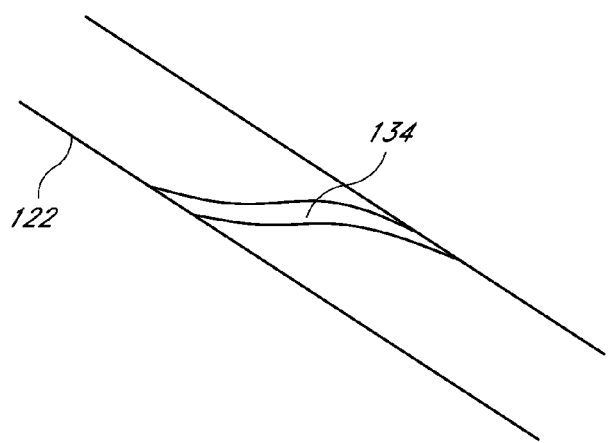

The routing tube 122 illustrated in FIG. 14 is permeable to enable the fluid 48 to exit the routing tube 122 and irrigate the wound. The routing tube 122 may be permeable because it comprises perforations, which may include many different shapes such as holes 130, slits 132, and spiral slots 134. FIGS. 15a-15c illustrate embodiments of holes 130, slits 132, and spiral slots 134. Thus, the routing tube 122 is a type of fluid-permeable tube. Other types of fluid-permeable tubes are not configured to enable a wire to be slideably disposed inside the tubes.

FIG. 16 illustrates the routing tube orientation angle 140, which helps define the spiral direction in which the wire 124 wraps around the tubular membrane 120 relative to the longitudinal axis of the surgical access device 8i. The routing tube orientation angle 140 can be any angle between 90 degrees and −90 degrees. In various embodiments, the routing tube orientation angle 140 is between 90 degrees and 60 degrees, between 70 degrees and 50 degrees, and between 35 degrees and 55 degrees. Other embodiments include the negative versions of the previously described ranges.

Figure 17:
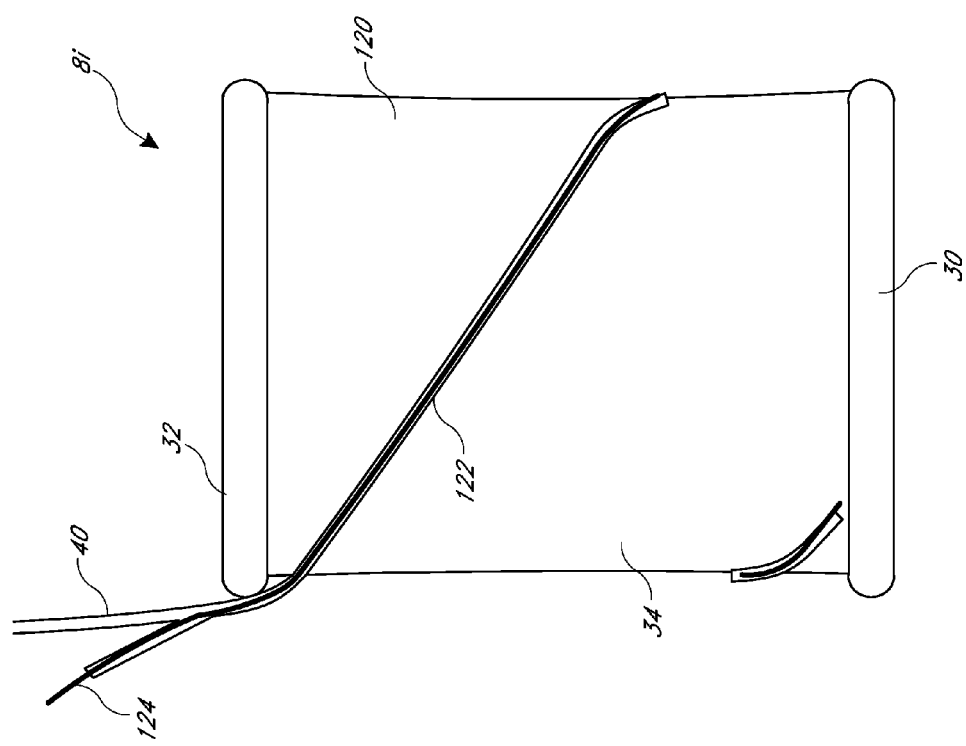
FIG. 17 is a side view that illustrates another example routing tube embodiment wherein a tubular membrane has a substantially cylindrical shape.

FIG. 17 illustrates another embodiment with a routing tube orientation angle 140. In this embodiment, the tubular membrane 120 has a substantially cylindrical shape.

Figure 18:
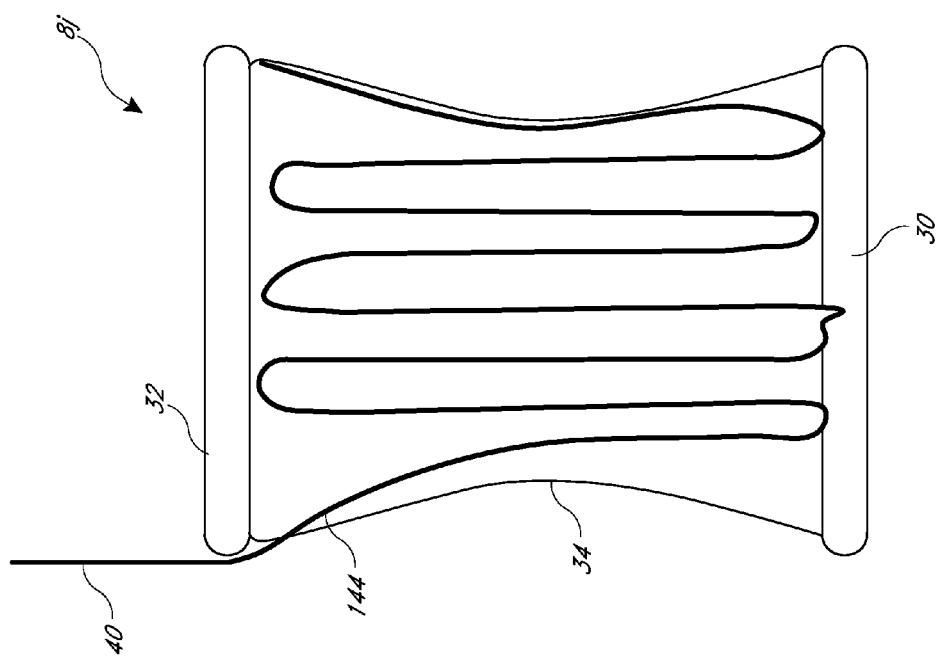
FIG. 18 is a side view of an embodiment wherein a pliable membrane includes irrigation tubing.

FIG. 18 illustrates an embodiment wherein the pliable membrane 34 includes irrigation tubing 144. The inlet conduit 40 is in fluid communication with the irrigation tubing 144 such that the fluid 48 flows though the inlet conduit 40, into the irrigation tubing 144, and out into the surgical site. In various embodiments, the irrigation tubes 144 are generally formed in an undulating pattern with portions that are generally vertical.

Figure 19:
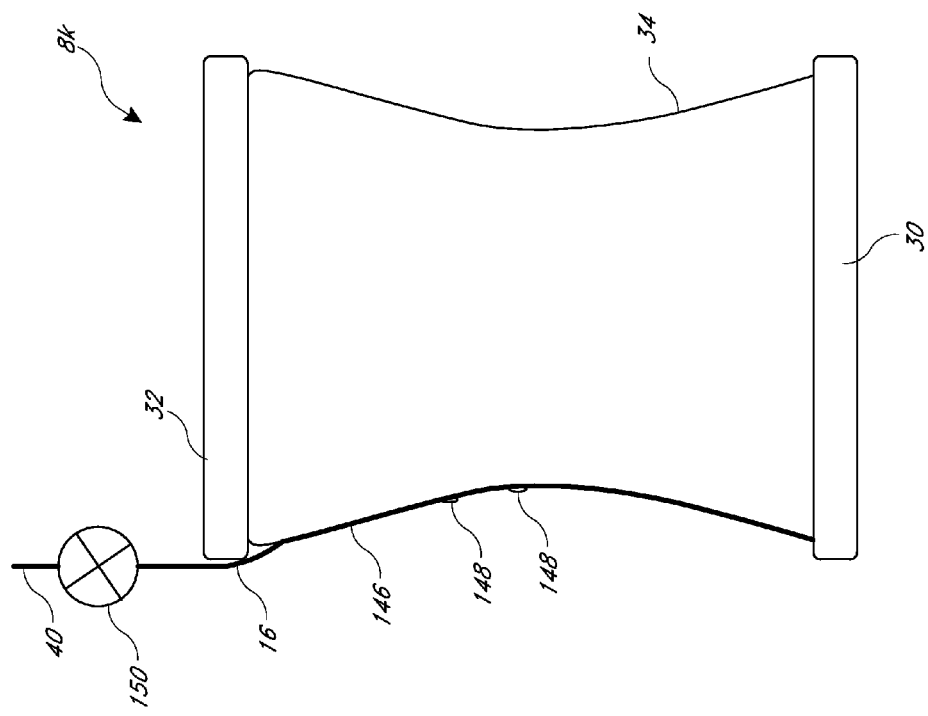
FIG. 19 is a side view of an embodiment that comprises a flow controlling means such as a flow regulator.

FIG. 19 illustrates an embodiment wherein the fluid delivery member 16 comprises a tubing having a lumen 146 with holes 148. The lumen holes 148 are configured to deliver fluid to the surgical site.

FIG. 19 also illustrates an embodiment that comprises a flow controlling means such as a flow regulator 150. A flow controlling means can optionally be placed within the inlet flow system to limit the flow rate into the surgical access device 8k. A flow controlling means can optionally be placed within the outlet flow system to limit the flow rate out of the surgical access device 8k. Additionally, the flow controlling means can be integrated with a fluid conduit connector or integrated into a portion of the surgical access device 8k.

The flow regulator 150 can contain a means of regulating pressure and/or flow rate into the device. Optionally, the regulation means can be a pressure-reducing element, such as a high flow resistance member. Optionally, the regulation means can establish a pressure threshold to substantially ensure sufficient pressure exists to establish the fluid flow. The regulation means can be comprised of a one-way valve with a defined cracking pressure, a flapper valve, or a duckbill valve. Additionally, the flow controlling means assembly can incorporate a feedback element indicating to the user when fluid is flowing through the device. For example, the flow controlling means can include a spinning turbine indicator.

Figure 20:
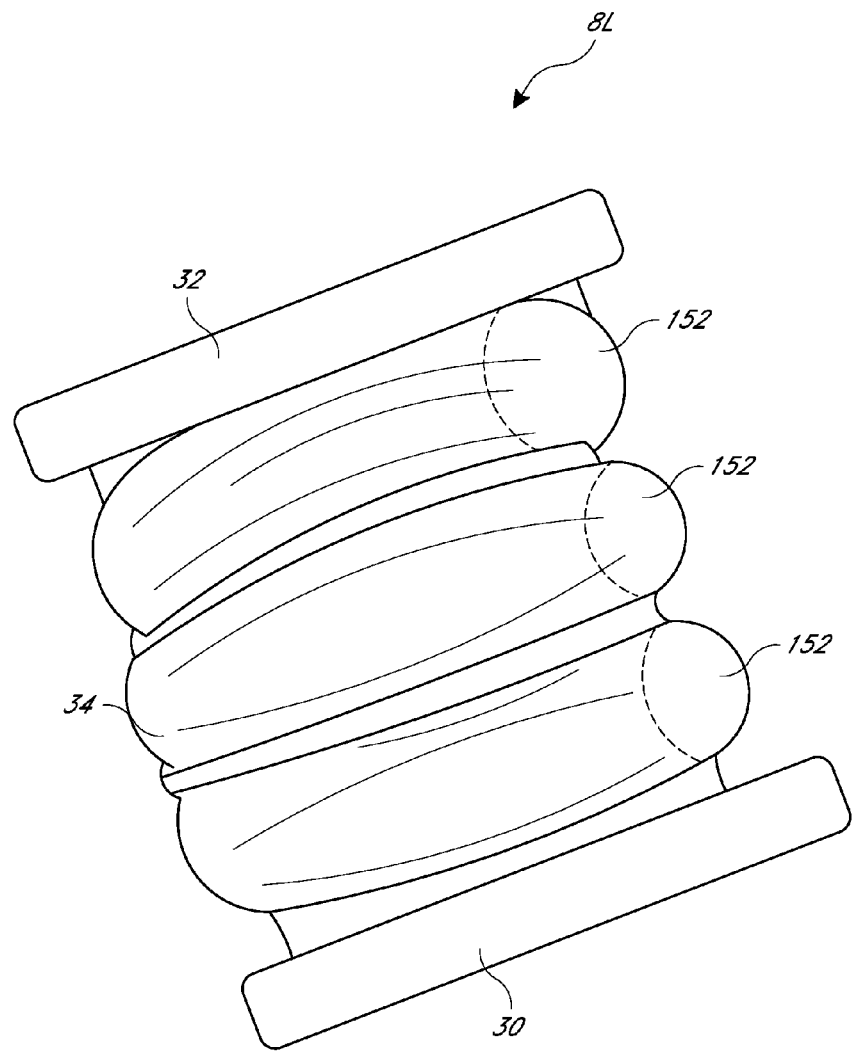
FIG. 20 is a side view of an embodiment configured to expand an incision by inflating chambers.
Figure 21:
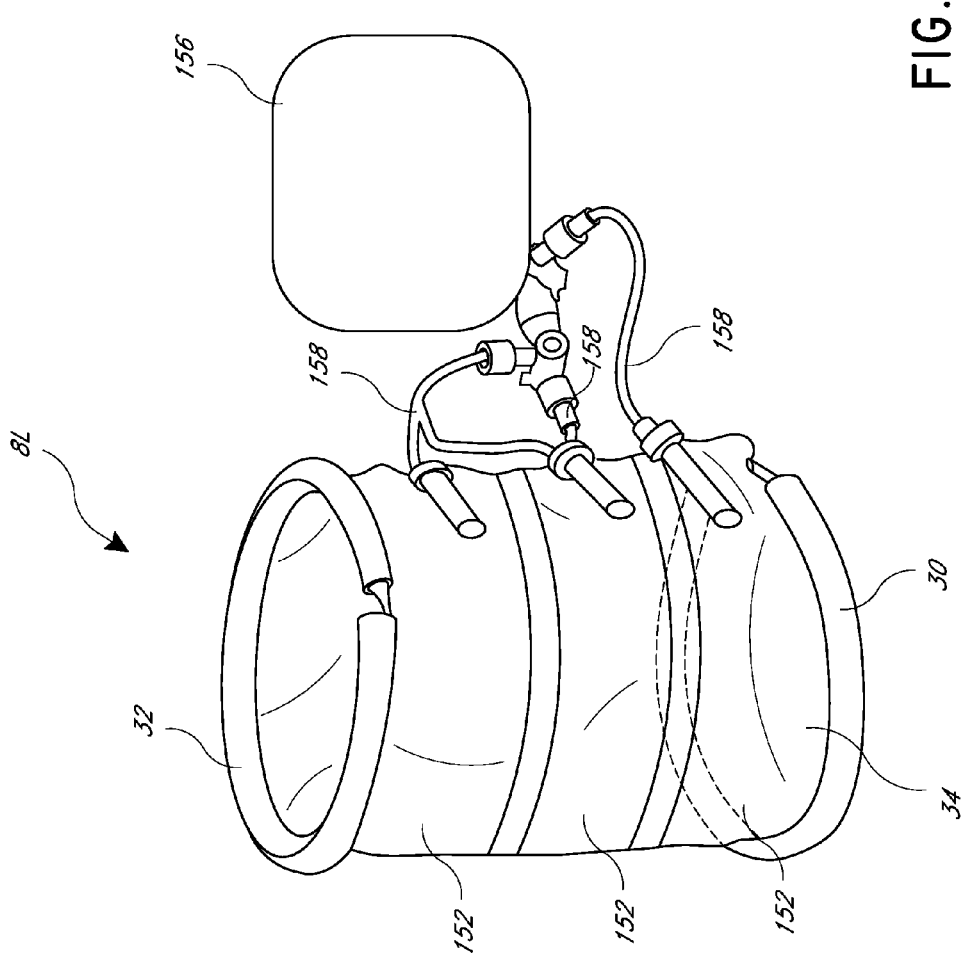
FIG. 21 is a perspective view of an embodiment configured to expand an incision by inflating chambers.

FIGS. 20 and 21 illustrate another means to expand the incision to facilitate access to a surgical site within a patient's body. The surgical access device 8L comprises a first retention ring 30, a second retention ring 32, and a pliable membrane 34 extending between the first retention ring 30 and the second retention ring 32. The pliable membrane 34 is configured to expand the incision by inflating with a liquid or a gas. The pliable membrane 34 comprises inflatable chambers 152, which are selectively placeable in fluid communication with a fluid source. Inflating the inflatable chambers 152 pushes the surgical site in an outward direction. Thus, the surgical access device 8L expands the incision.

A high-pressure fluid source 156 (as shown in FIG. 21) may be used to inflate the inflatable chambers 152. In one embodiment, the inflatable chambers 152 are inflated to 30 pounds per square inch. Inflation tubes 158 place the high-pressure fluid source 156 in fluid communication with the inflatable chambers 152. In one embodiment, at least some of the inflatable chambers 152 are approximately donut-shaped or hoop-shaped. In another embodiment, an inflatable chamber is helical or spherical. In one embodiment, the high-pressure fluid source is a pressurized $CO_2$ cartridge.

FIGS. 22-25 illustrate an expandable ring embodiment with at least ten linkages. In some embodiments, surgical access devices with an expandable ring enable wound irrigation, but do not expand the incision to enable surgical access. In other embodiments, surgical access devices with an expandable ring do not enable wound irrigation, but expand the incision to enable surgical access. In other embodiments, surgical access devices with an expandable ring enable wound irrigation and expand the incision to enable surgical access.

Figure 22:
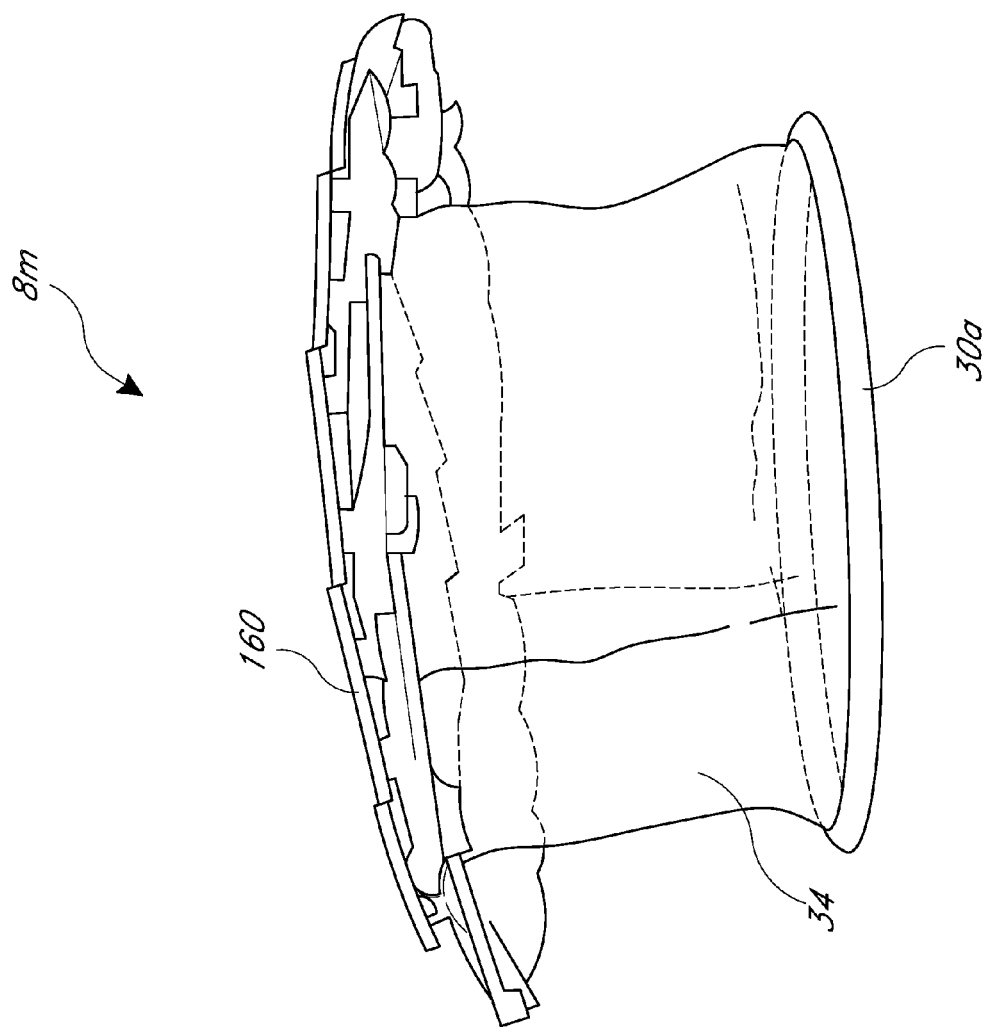
FIG. 22 is a side view of an embodiment wherein an expandable ring is configured to expand an incision.
Figure 23:
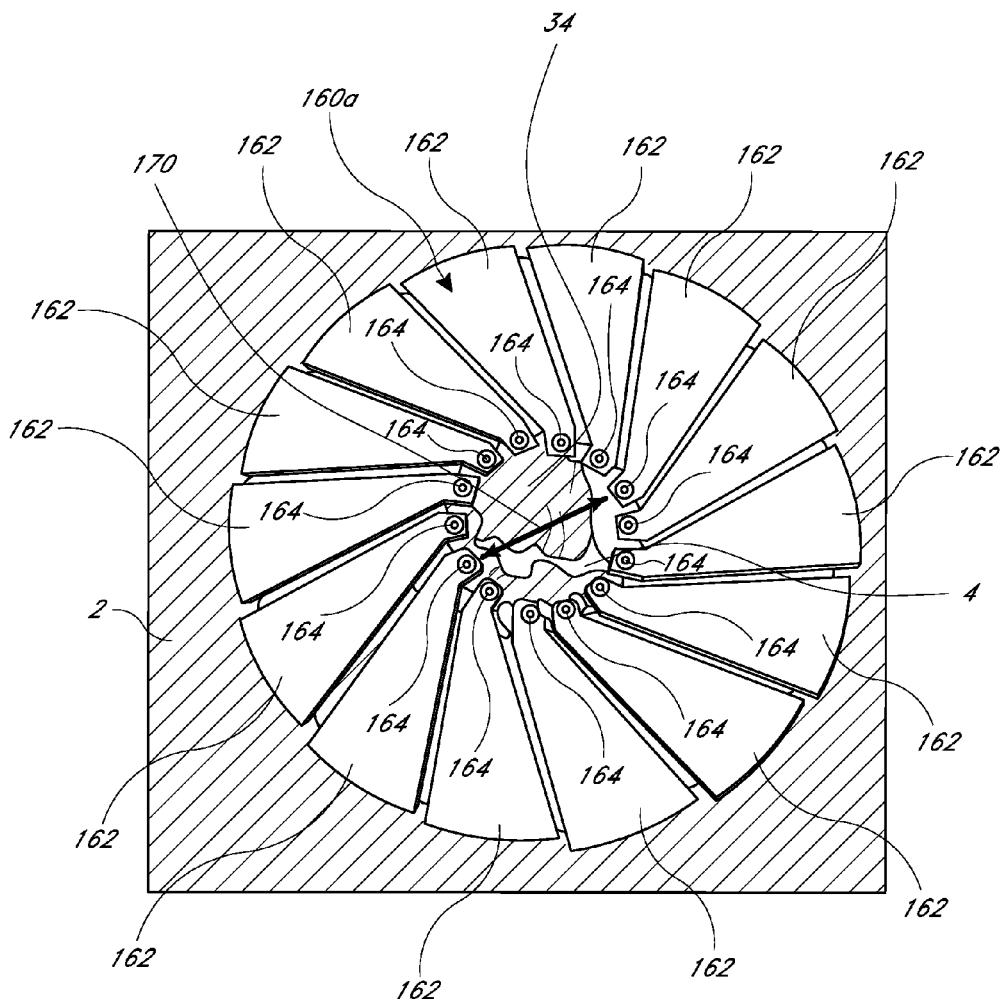
FIG. 23 is a top view of an embodiment with an expandable ring in a collapsed configuration.
Figure 24:
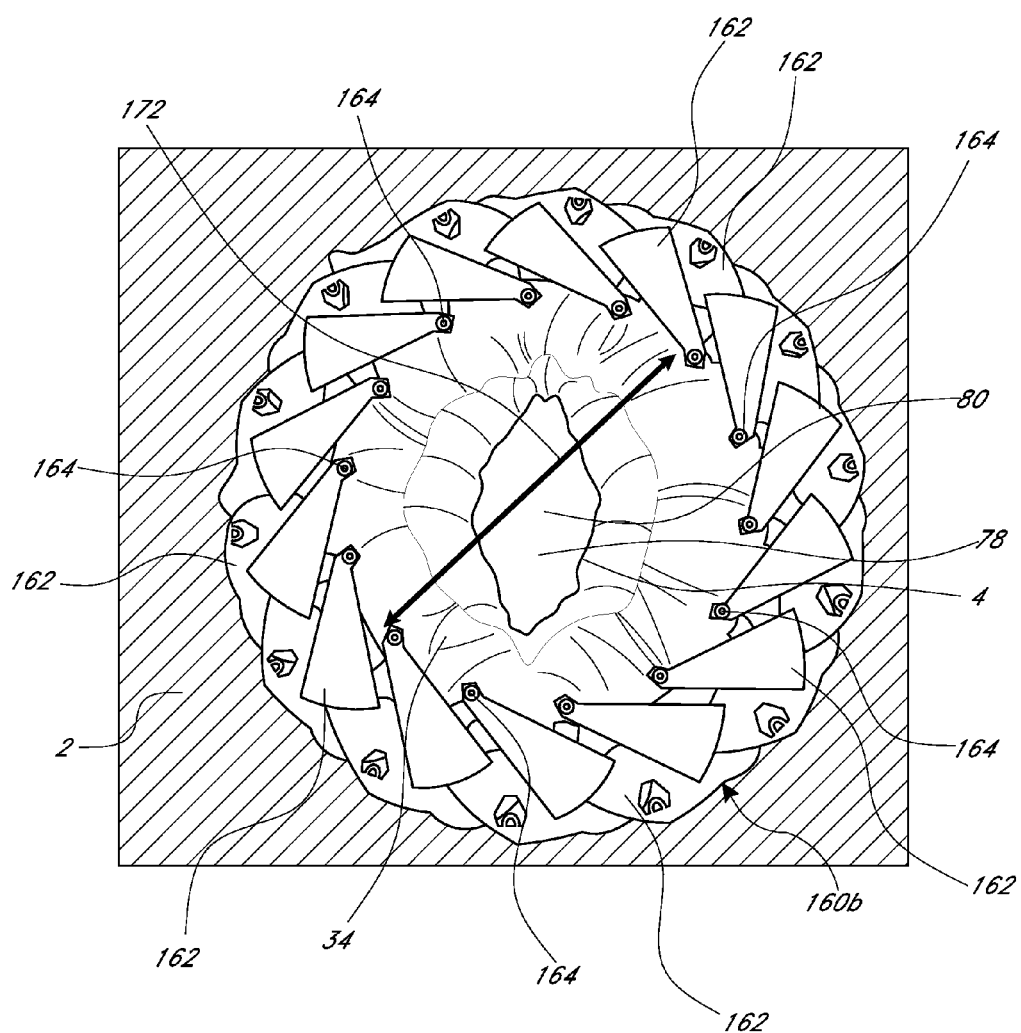
FIG. 24 is a top view of an embodiment with an expandable ring in an expanded configuration.

The embodiment illustrated in FIGS. 22-25 comprises a first retention ring 30, an expandable ring 160, and a pliable membrane 34 extending between the first retention ring 30 and the expandable retention ring 160. FIG. 23 shows the expandable ring 160 in a collapsed configuration 160a. FIG. 24 shows the expandable ring 160 in an expanded configuration 160b. Not all of the elements in FIG. 24 are labeled in order to make the illustration less cluttered and easier to see. For example, not all of the pivots 164, which are represented by circles, are labeled. Some of the pivots 164 are hidden by linkages 162. Not all of the linkages 162 are labeled. The patient's skin 2 in FIGS. 23 and 24 is indicated by cross hatching. A central channel 78 extends through the center of the pliable membrane 34 to provide access to the surgical site, which is target site 80 in FIG. 24.

Several embodiments of systems with expandable retention rings reduce the need to use different retractor sizes in a single surgical site because the expandable retention ring can grow in diameter as the incision size increases. These embodiments sometimes eliminate the need to replace a first retractor with a second, larger retractor if the incision becomes larger.

The collapsed configuration 160a is the configuration in which the expandable ring 160 has the smallest inner diameter 170. Configurations with an inner diameter 172 that is larger than the smallest inner diameter 170 are expanded configurations. In one embodiment, the inner diameter of the maximum expanded configuration is at least 50% larger than the inner diameter of the collapsed configuration 160a. In another embodiment, the inner diameter of the maximum expanded configuration is at least 100% larger than the inner diameter of the collapsed configuration 160a. In yet another embodiment, the inner diameter of the maximum expanded configuration is at least 200% larger than the inner diameter of the collapsed configuration 160a. In many embodiments, there are many expanded configurations with inner diameters that are smaller than the inner diameter of the maximum expanded configuration.

In the illustrated embodiment, the expandable ring 160 is configured to expand from a collapsed configuration 160a to an expanded configuration 160b. The expandable ring 160 is an example of an expandable retention member. The expandable retention ring 160 comprises at least four linkages 162 pivotably coupled to one another by pivots 162 such that expanding the expandable ring 160 causes the linkages 162 to pivot relative to each other. In other embodiments, an expandable retention member comprises at least three linkages that may form in a "C" shape.

Figure 25:
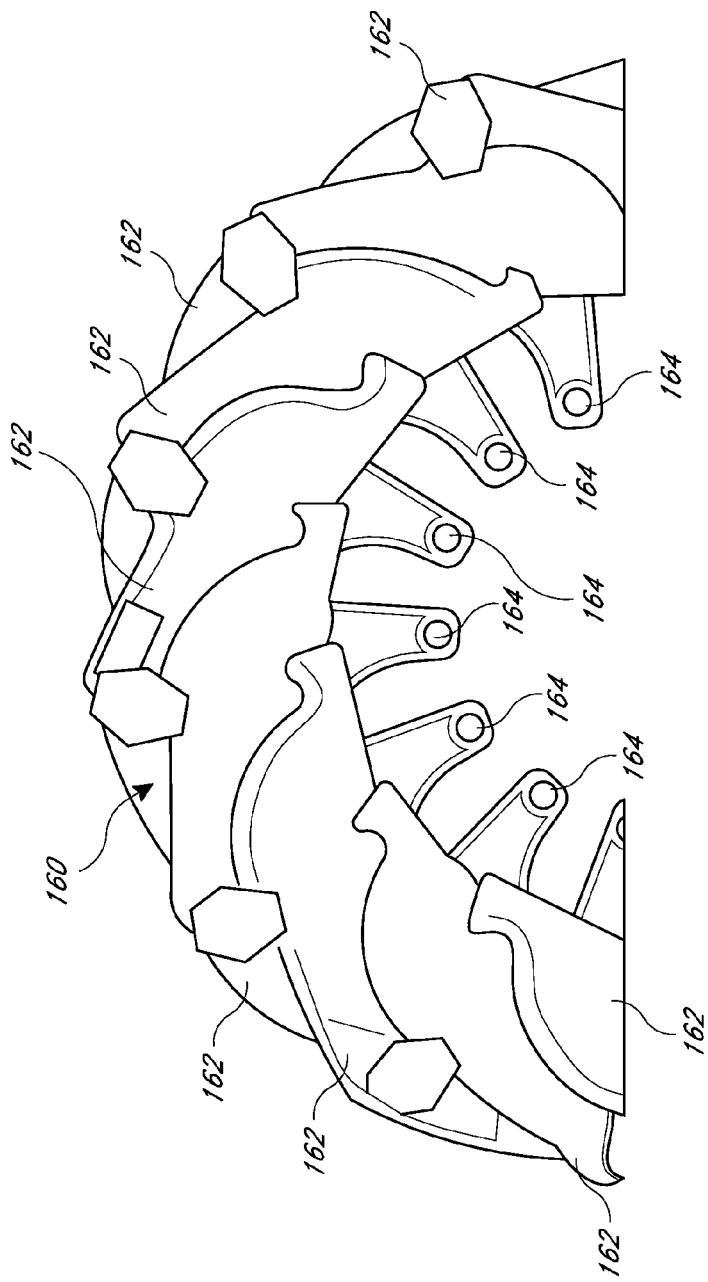
FIG. 25 is a bottom view of approximately half of an expandable ring embodiment.

FIG. 24 shows the upper side of the expandable ring 160. FIG. 25 shows approximately half of the lower side of the expandable ring 160. A pivot 164 may be formed by a pin on one link that is pivotably located inside a cylindrical hole of another link. Both FIG. 24 and FIG. 25 show pivot embodiments, although other expandable ring 160 embodiments comprise other pivot styles, pivot locations, and pivot geometries.

The first retention ring 30 and the second retention ring 32 may be made from rubber. In the embodiment illustrated in FIG. 22, a first retention ring 30a is made from 85 Shore A medical-grade rubber. This first retention ring 30a is deformable because a physician can squeeze the ring's otherwise circular shape into an elliptical shape or into another suitable shape to squeeze the ring into the incision in a collapsed configuration. Once the ring is in the desired location inside the patient's body, the physician can stop squeezing the ring to allow the ring to at least partially return to its initial shape. In this embodiment, the initial shape is circular. Thus, the ring would return to a generally circular shape or to a generally elliptical shape. A retention ring is deformable if a typical physician can substantially deform the retention ring to place the retention ring into an incision without breaking the retention ring. In several embodiments, the first retention ring 30 is not deformable.

In an embodiment, the second retention ring 32 is made from 50 Shore D medical-grade plastic. In this embodiment, the second retention ring 32 is less flexible than the first retention ring 30 because the second retention ring 32 does not have to collapse or deform to enter the patient's body. In other embodiments, the second retention ring 32 collapses and/or deforms.

In several embodiments, a pliable membrane is made from medical-grade silicone rubber. In some embodiments, the pliable membrane comprises a silicone tube with an inner diameter large enough to enable a physician's hand to pass through the inner diameter. In some embodiments, the pliable membrane may also include a plastic tube that spirals around the silicone tube.

In other embodiments, the pliable membrane comprises polyethylene, polyurethane, or nylon. In one embodiment, the tubular membrane is made from polyethylene.

In any method or process disclosed herein, the acts or operations of the method or process may be performed in any suitable sequence and are not necessarily limited to any particular disclosed sequence. Moreover, the methods described herein include many optional steps and many optional step elements and portions. Many of the methods depicted in the Figures include alternative steps. Thus, method embodiments often do not include performing each step depicted in the Figures, but rather often include only a subset of the depicted steps.

A method for retracting and providing fluid to tissue around an incision in a body during surgery may involve advancing a first retention ring into the body through the incision in a collapsed configuration and placing a second retention ring outside the body. The second retention ring may be coupled to the first retention ring by a pliable membrane. The pliable membrane may be configured to retract the tissue around the incision. The method may further involve retracting the tissue around the incision and introducing the fluid into a fluid delivery inlet coupled to the pliable membrane such that the fluid exits the pliable membrane through at least one opening in the pliable membrane.

The method may additionally involve vacuuming or suctioning the fluid into the pliable membrane and removing the fluid from the body. Alternatively or additionally, a fluid conduit member may be coupled to the first retention ring and the method may involve vacuuming or suctioning the fluid into the fluid conduit member and removing the fluid from the body. The fluid may comprise an antibiotic fluid, a saline solution, any suitable irrigation fluid, any medicating fluid, or any other therapeutic fluid.

The method may additionally involve expanding the second retention ring whereby expanding the second retention ring causes the pliable membrane to retract the tissue around the incision. In select embodiments, the second retention ring comprises at least four linkages pivotably coupled to one another and expanding the second retention ring comprises pivoting the at least four linkages relative to each other.

In another embodiment, a wire is spirally or helically wound around the pliable membrane and retracting the tissue around the incision comprises pulling the wire. Pulling the wire alters the hoop strength of the pliable membrane, which retracts the tissue. In various configurations, pushing the wire increases the hoop strength, which retracts the tissue. In such cases, a wire is spirally or helically wound around the pliable membrane and retracting the tissue around the incision comprises pushing the wire.

In another embodiment, retracting the tissue around the incision involves inflating at least a portion of the pliable membrane. In one embodiment, inflatable air chambers inflate such that they become donut-shaped or such that they form a tube through which a physician can insert her hand to reach the target site. Fluids such as water and saline solution may be used to inflate the chambers. Gases may also be used to inflate the chambers. The membrane may be permeable to permit the inflating material to exit the membrane and be delivered to the tissue.

Figure 26:
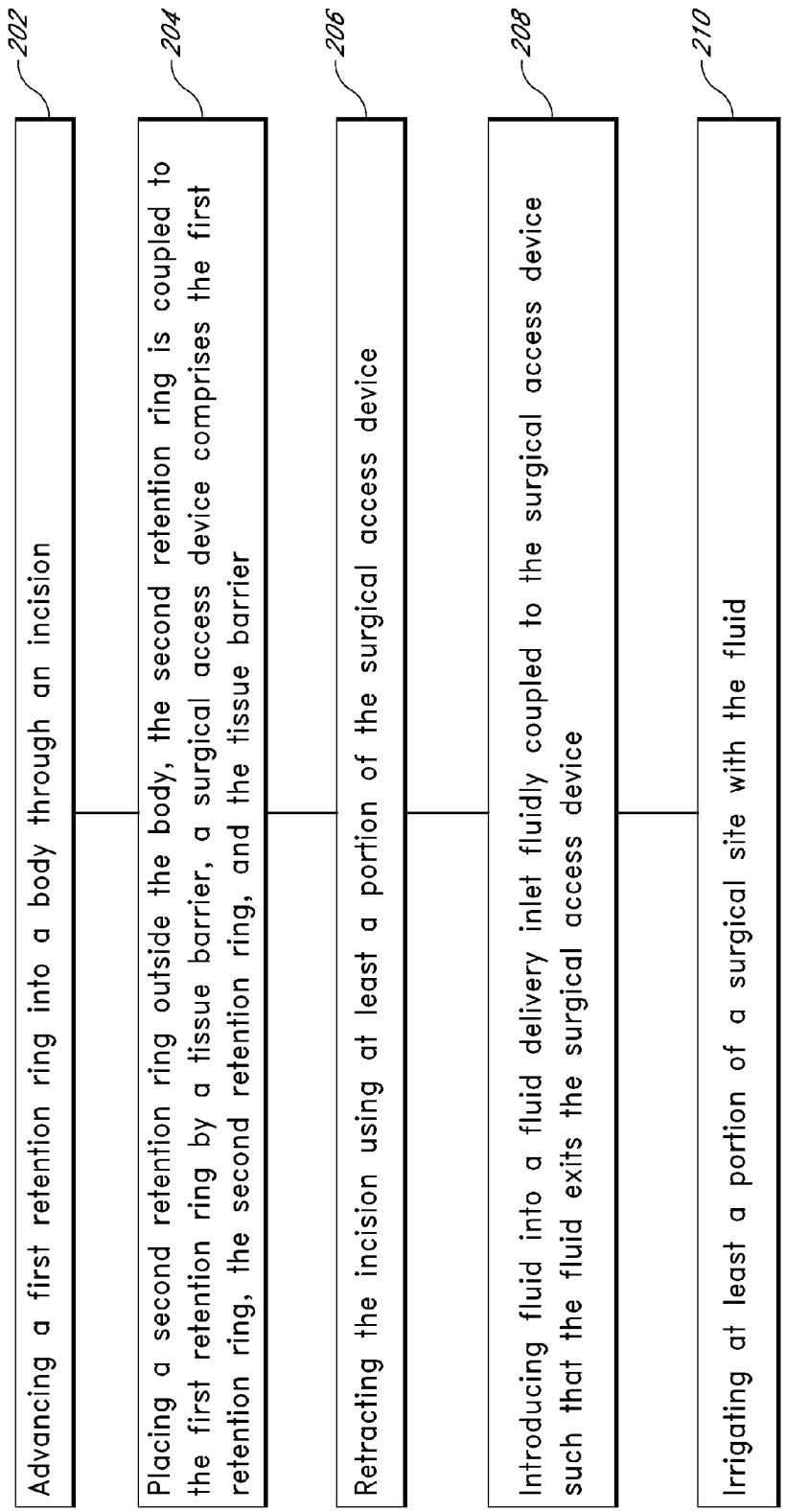
FIGS. 26-29 are flow charts illustrating exemplary method steps.

FIG. 26 illustrates an alternative method embodiment. Step 202 may include advancing a first retention ring into a body through an incision. Step 204 may involve placing a second retention ring outside the body. The second retention ring may be coupled to the first retention ring by a tissue barrier. The surgical access device may comprise the first retention ring, the second retention ring, and the tissue barrier. Step 206 may involve retracting the incision using at least a portion of the surgical access device. Step 208 may include introducing fluid into a fluid delivery inlet fluidly coupled to the surgical access device such that the fluid exits the surgical access device. Step 210 may include irrigating at least a portion of a surgical site with the fluid.

Figure 27:
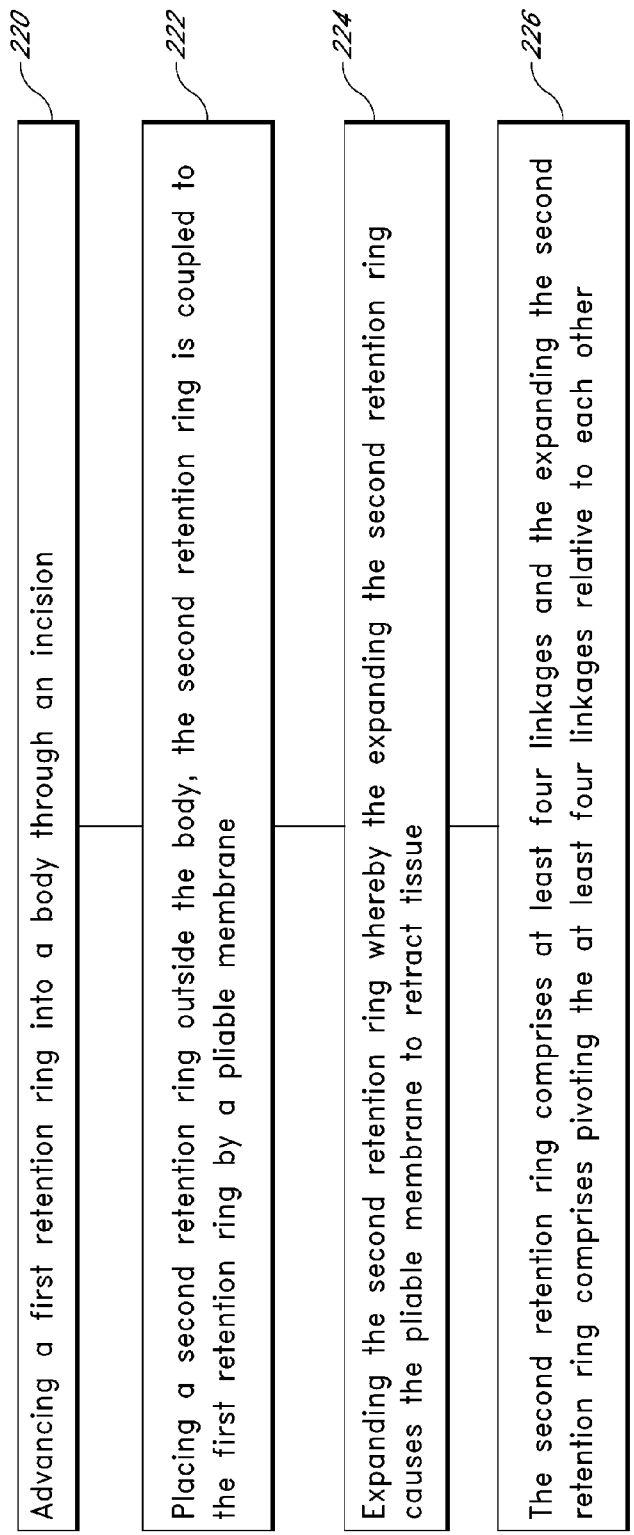

Several other embodiments do not include irrigation or fluid removal. For example, FIG. 27 illustrates an alternative method embodiment. As shown in Step 220, the method may include advancing a first retention ring into a body through an incision. As shown in Step 222, the method may also include placing a second retention ring outside the body. The second retention ring may be coupled to the first retention ring by a pliable membrane, a tubular member, a conical member, and/or by a tissue barrier. As shown in Step 224, the method may also include expanding the second retention ring, whereby expanding the second retention ring causes the pliable membrane to retract tissue around the incision. As shown in Step 226, the second retention ring may comprise at least four linkages. Expanding the second retention ring may comprise pivoting the at least four linkages relative to each other. In another embodiment, the second retention ring has at least three pivoting linkages. In yet another embodiment, the second retention ring has at least ten pivoting linkages. In yet another embodiment, the second retention ring has at least nineteen pivoting linkages.

Figure 28:
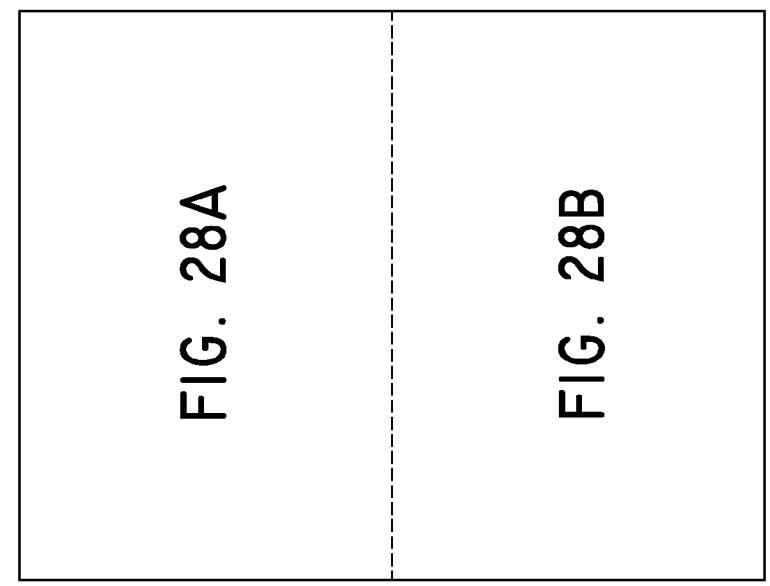
Figure 28A:
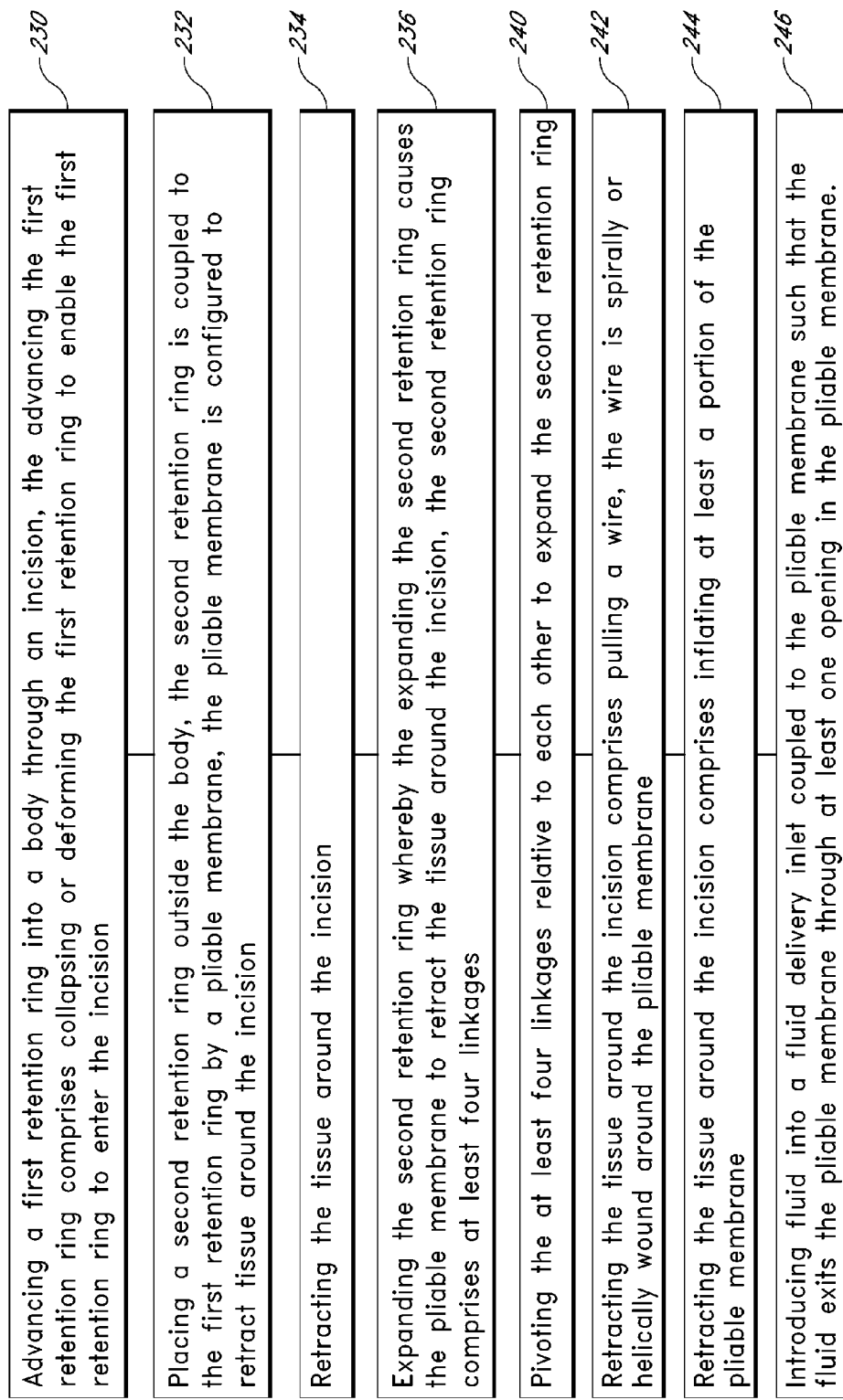
Figure 28B:
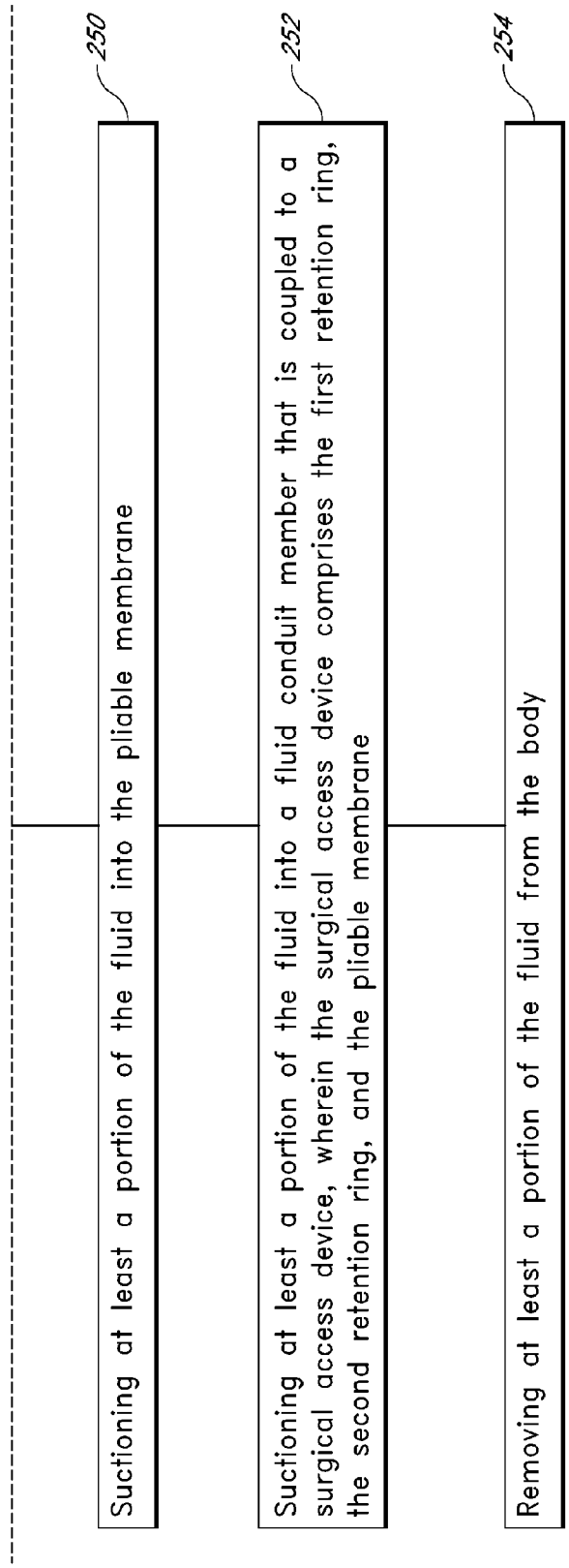

FIG. 28 illustrates many different method steps that may apply to various embodiments. Step 230 may include advancing a first retention ring into a body through an incision. Advancing the first retention ring through an incision may involve collapsing or deforming the first retention ring to enable the first retention ring to enter the incision. Step 232 may include placing a second retention ring outside the body. The second retention ring may be coupled to the first retention ring by a pliable membrane. The pliable membrane may be configured to retract tissue around the incision.

Step 234 may include retracting the tissue around the incision. Step 236 may include expanding the second retention ring, whereby expanding the second retention ring causes the pliable membrane to retract the tissue around the incision. The second retention ring may comprise at least four linkages, at least ten linkages, or at least nineteen linkages. Step 240 may include pivoting the linkages relative to each other to expand the second retention ring. Step 242 may include retracting the tissue around the incision by pulling a wire or by pushing a wire. The wire may be spirally or helically wound around the pliable membrane. Step 244 may include retracting the tissue around the incision by inflating at least a portion of the pliable membrane to expand the outer diameter of the pliable membrane to push the tissue out of the way and to create an access channel through which the physician can insert a hand.

Step 246 may include introducing fluid into a fluid delivery inlet coupled to the pliable membrane such that the fluid exits the pliable membrane through at least one opening in the pliable membrane. Other embodiments include at least six openings in the pliable membrane.

Step 250 may include vacuuming or suctioning at least a portion of the fluid into the pliable membrane or into another part of the surgical access device. Another embodiment includes vacuuming or suctioning at least a portion of the fluid into the first retention ring. Yet another embodiment includes vacuuming or suctioning at least a portion of the fluid into the second retention ring.

Step 252 may include vacuuming or suctioning at least a portion of the fluid into a fluid conduit member that is coupled to a surgical access device. The surgical access device may comprise the first retention ring, the second retention ring, and the pliable membrane.

Step 254 may include removing at least a portion of the fluid from the patient's body. For example, at least a portion of the irrigating solution and additional bodily fluid, such as blood, may be removed from the patient's body.

Figure 29:
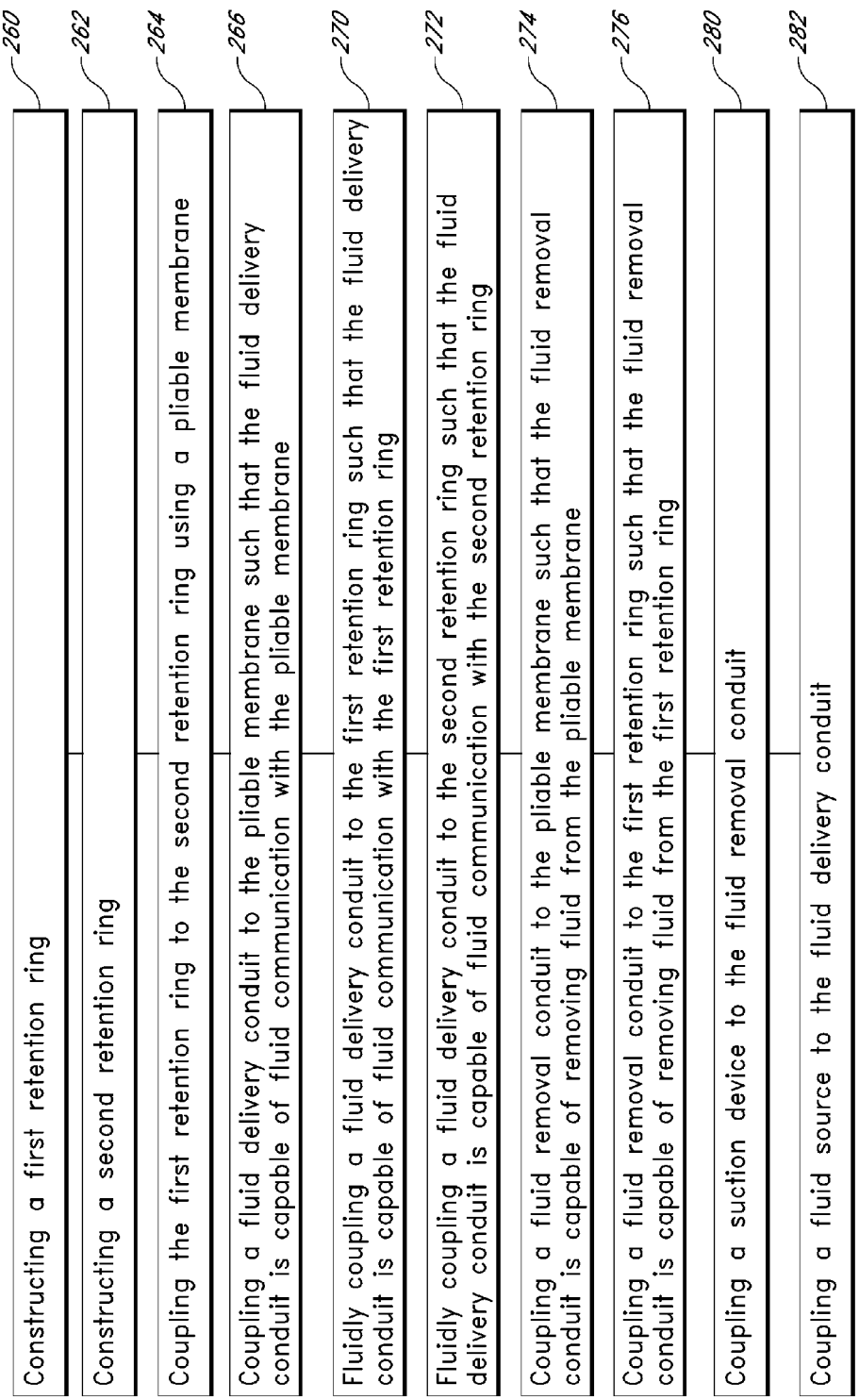

FIG. 29 illustrates various manufacturing and/or assembly steps that apply to various embodiments. Step 260 may include constructing a first retention ring. Step 262 may include constructing a second retention ring. Step 264 may include coupling the first retention ring to the second retention ring using a pliable membrane. In at least one embodiment, one end of a pliable membrane is coupled to a first retention ring and a second end of the pliable membrane is coupled to a second retention ring. In other embodiments, a retention ring is coupled to a portion of the pliable membrane that is between the first end and the second end.

Step 266 may include coupling a fluid delivery conduit to the pliable membrane such that the fluid delivery conduit is capable of fluid communication with the pliable membrane. Step 270 may include fluidly coupling a fluid delivery conduit to the first retention ring such that the fluid delivery conduit is capable of fluid communication with the first retention ring. Step 272 may include fluidly coupling a fluid delivery conduit to the second retention ring such that the fluid delivery conduit is capable of fluid communication with the second retention ring.

Step 274 may include coupling a fluid removal conduit to the pliable membrane such that the fluid removal conduit is capable of removing fluid from the pliable membrane. Step 276 may include coupling a fluid removal conduit to the first retention ring such that the fluid removal conduit is capable of removing fluid from the first retention ring. Step 280 may include coupling a vacuum or suction device to the fluid removal conduit. Step 282 may include coupling a fluid source to the fluid delivery conduit.

FIGS. 24 and 25 illustrate an expandable ring embodiment that comprises pivots 164, which pivotably couple linkages 162. Other expandable ring 160 embodiments comprise other pivot styles, pivot locations, and pivot geometries. In several embodiments, expandable rings do not use pivots, but instead use living hinges. Living hinges may pivotably couple linkages.

In one embodiment, a second retention ring is configured to expand from a collapsed configuration to an expanded configuration. The second retention ring comprises at least four linkages pivotably coupled to one another by living hinges such that expanding the second retention ring causes the linkages to pivot relative to each other. In several embodiments, a first retention ring is configured to expand from a collapsed configuration to an expanded configuration. The first retention ring comprises at least four linkages pivotably coupled to one another by living hinges such that expanding the second retention ring causes the linkages to pivot relative to each other.

In at least one embodiment, two sets of linkage chains having living hinges connecting each link are connected to each other by a pinned pivot joint. In one embodiment, a living hinge is made by a section of material that is thinner and more flexible than the adjoining sections of material that the living hinge connects.

Figure 30A:
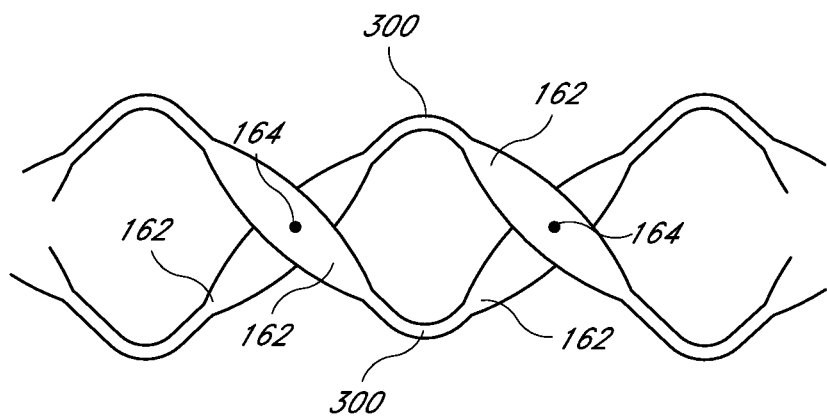
FIG. 30a is a top view of a portion of an expandable ring with non-living pivots and living hinges, according to one embodiment.

FIG. 30*a* illustrates a section of an expandable ring embodiment with living hinges 300 and pivots 164. In this embodiment, both the living hinges 300 and the pivots 164 help to pivotably couple the linkages 162. The linkages 162 are coupled by living hinges 300 instead of being coupled solely by hinges comprising of one or more parts rotating about a bearing surface. One example of a bearing-surface, pivot design is a part rotating about a pin. The bearing surfaces may be the inner diameter of a cylindrical hole and the outer diameter of a pin. Bearing-surface pivots may be referred to as bearing surface hinges, pinned hinges, or pin joints. Potential advantages of living hinges may include reduced part count, less assembly complexity, and improved durability.

In the embodiment illustrated in FIG. 30*a*, each linkage subassembly is formed in a generally "zig-zag" shape. In other words, in several embodiments, the shape substantially shortens its overall length when its linkages 162 are brought together by bending the living hinges 300 that join the linkages 162 of the subassembly. The bending of the living hinges 300 enables the linkages 162 to pivot relative to each other. This pivoting action is permitted by a region of substantially thinner material in the bending area. In one embodiment, the material used to create the linkages 162 has high fatigue resistance. Several embodiments use polypropylene, polyethylene, or another suitable polyolefin. Other polymers may be used, and in some embodiments, metals may be used.

The two linkage subassemblies can be pivotably joined by a pinned hinge joint or other suitable non-living hinge joint to enable the expanding ring design described previously. In FIG. 30a, the subassemblies are pivotably joined by pivots 164.

Various embodiments utilize injection molding, die cutting, water-jet cutting, wire electrical discharge machining, laser cutting, and etching to manufacture the linkages. In one embodiment, an expandable ring is manufactured by overmolding in a single-shot mold, with pin-hinge elements molded in place.

Figure 30B:
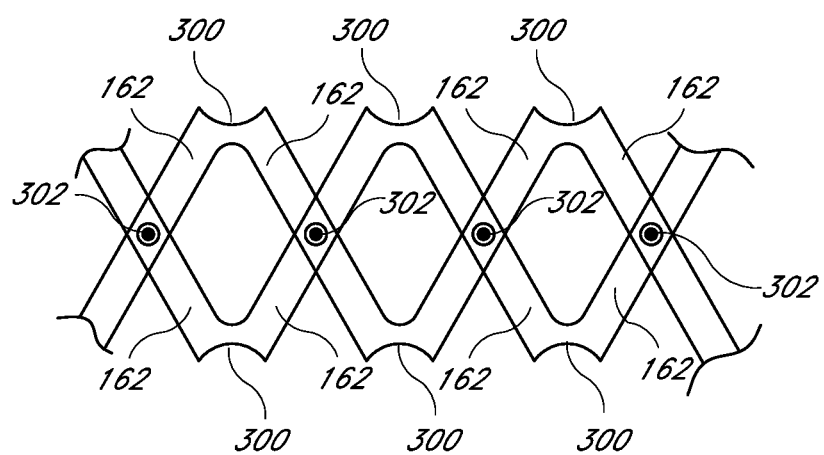
FIG. 30b is a top view of a portion of an expandable ring with living pivots and living hinges, according to one embodiment.

FIG. 30b illustrates a section of an expandable ring embodiment wherein all of the pivoting sections are living hinges 300 rather than traditional pin pivots. In this embodiment, living hinges 300 pivotably couple the linkages 162. Cylindrical hinges 302 couple intersecting linkages 162. Cylindrical hinges 302 are another type of living hinge that are essentially cylindrical columns of the material used to mold the linkages 162. The cylindrical hinges 302 twist to enable the linkages 162 to pivot relative to each other. In this embodiment, the entire expandable ring may be molded as a single piece.

In various embodiments, the linkages of an expandable ring have different lengths and are oriented relative to each other at different angles. This approach enables noncircular and/or nonsymmetrical collapsed and expanded shapes. Noncircular shapes can be advantageous to better match the geometry of an expanded incision than is possible with a circular shape.

Expandable rings may have many different types of shapes including the shapes illustrated in FIGS. 9a-9d. For example, an expandable ring may have an elliptical shape as shown in FIG. 9d. The curvature of an elliptical expandable ring is greater near an end of the major axis than near the near an end of the minor axis. Curvature can be controlled by adjusting the link angle of individual linkages, where the link angle is defined as the angle between a line connecting a first pivot disposed at a first end of the linkage and a second pivot disposed at a substantially central portion of the linkage and a line connecting a third pivot disposed at a second end of the linkage and the second pivot. Greater curvature can be achieved by decreasing the link angle of the pivotably coupled links. Lesser curvature can be achieved by increasing the link angle of the pivotably coupled links. In other words, the link angles near an end of the major axis are smaller than link angles near an end of the minor axis. In one embodiment, the link angle of the pivotably coupled links at an end of the major axis are 150 degrees, while the link angle of the pivotably coupled links at an end of the minor axis are 165 degrees.

Figure 31A:
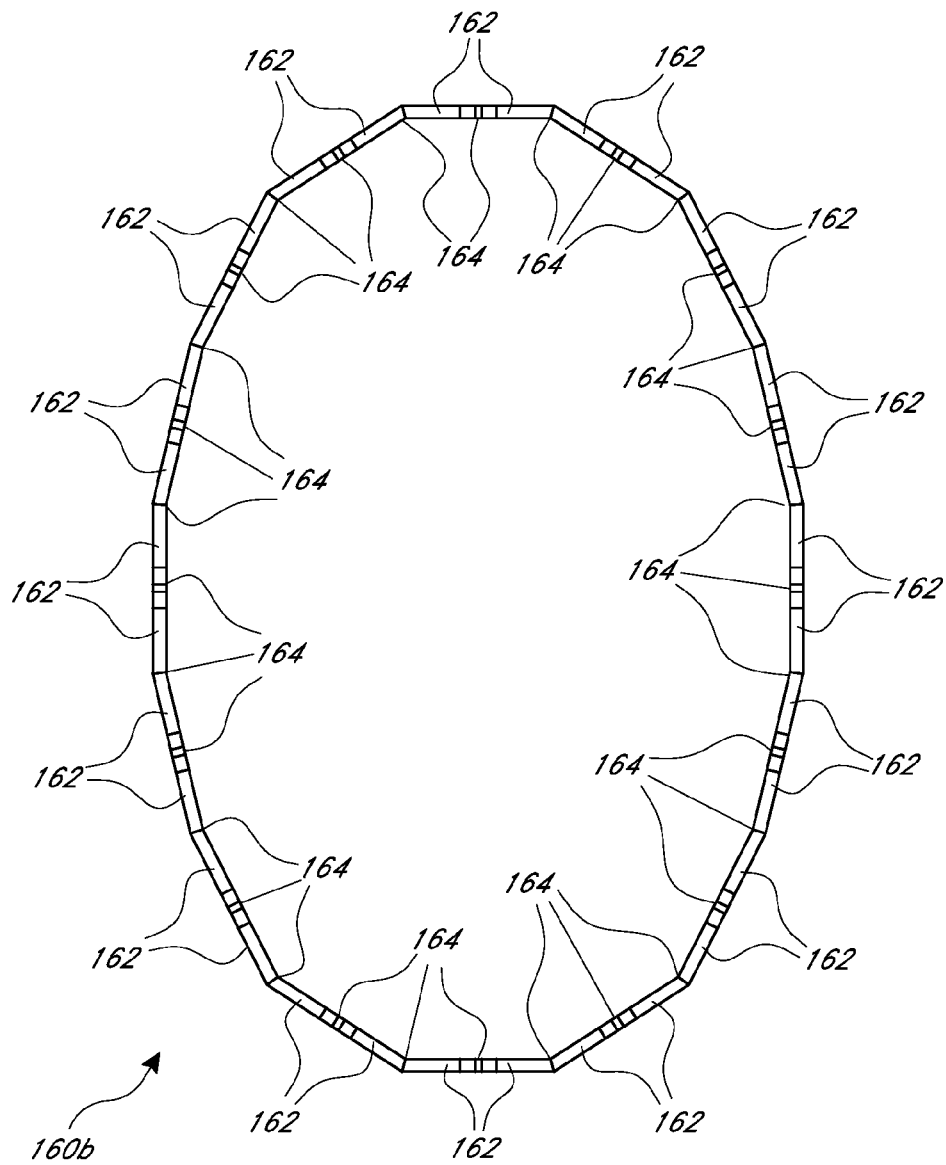
FIG. 31a is a top view of a completely expanded ring that is elliptical, according to one embodiment.

FIG. 31a illustrates an expandable ring 160 in a completely expanded configuration. FIG. 31b illustrates the expandable ring 160 from FIG. 31a in a completely collapsed configuration. Not all of the elements in FIG. 31b are labeled in order to make the illustration less cluttered and easier to see. For example, not all of the pivots 164, which are represented by small circles, are labeled. The expandable ring 160 illustrated in FIGS. 31a and 31b is elliptical. The angle between adjacent linkages 162 is called the link angle. The lengths of the linkages 162 and the link angles play an important role in determining the shape of the expandable ring 160. Using different lengths and link angles enable many diverse expandable ring shapes including shapes that are generally circular, elliptical, rectangular, and triangular.

Differing regions of curvature can be achieved by incorporating different link angles. As illustrated in FIG. 31b, link angles 166 and 168 are generally smaller in regions of greater curvature (e.g., near the major axis of an elliptical shape) than in regions of lesser curvature (e.g., near the minor axis of an elliptical shape).

Maintaining an expanded configuration is often desirable to facilitate surgery as well as to deliver a therapeutic fluid. In general, a kinematic property of several of the expandable ring embodiments disclosed previously is that constraining the relative position of any 2 links or pivots is sufficient to constrain the shape of the expandable ring structure. This property arises from the linkages being coupled together in an expandable, interrelated manner.

The retention ring may comprise ratchet teeth configured to selectively maintain an expanded configuration. The retention ring may also comprise at least one ratchet pawl configured to selectively maintain the expanded configuration by engaging at least a portion of the ratchet teeth. The surgical access device may also comprise a release member configured to disengage the ratchet pawl from the ratchet teeth to enable the retention ring to return to the collapsed configuration. In select embodiments, the surgical access device comprises a user interface button coupled to at least one of the ratchet teeth and/or to the ratchet pawl. The user interface button is configured to disengage the ratchet pawl from the ratchet teeth to enable the retention ring to return to the collapsed configuration. In at least one embodiment, the surgical access device comprises a locking mechanism. The locking mechanism is configured to selectively lock the second retention ring in an expanded configuration. The locking mechanism can comprise a protrusion and an indentation. The protrusion is configured to engage the indentation to selectively lock the retention ring in the expanded configuration.

Figure 32:
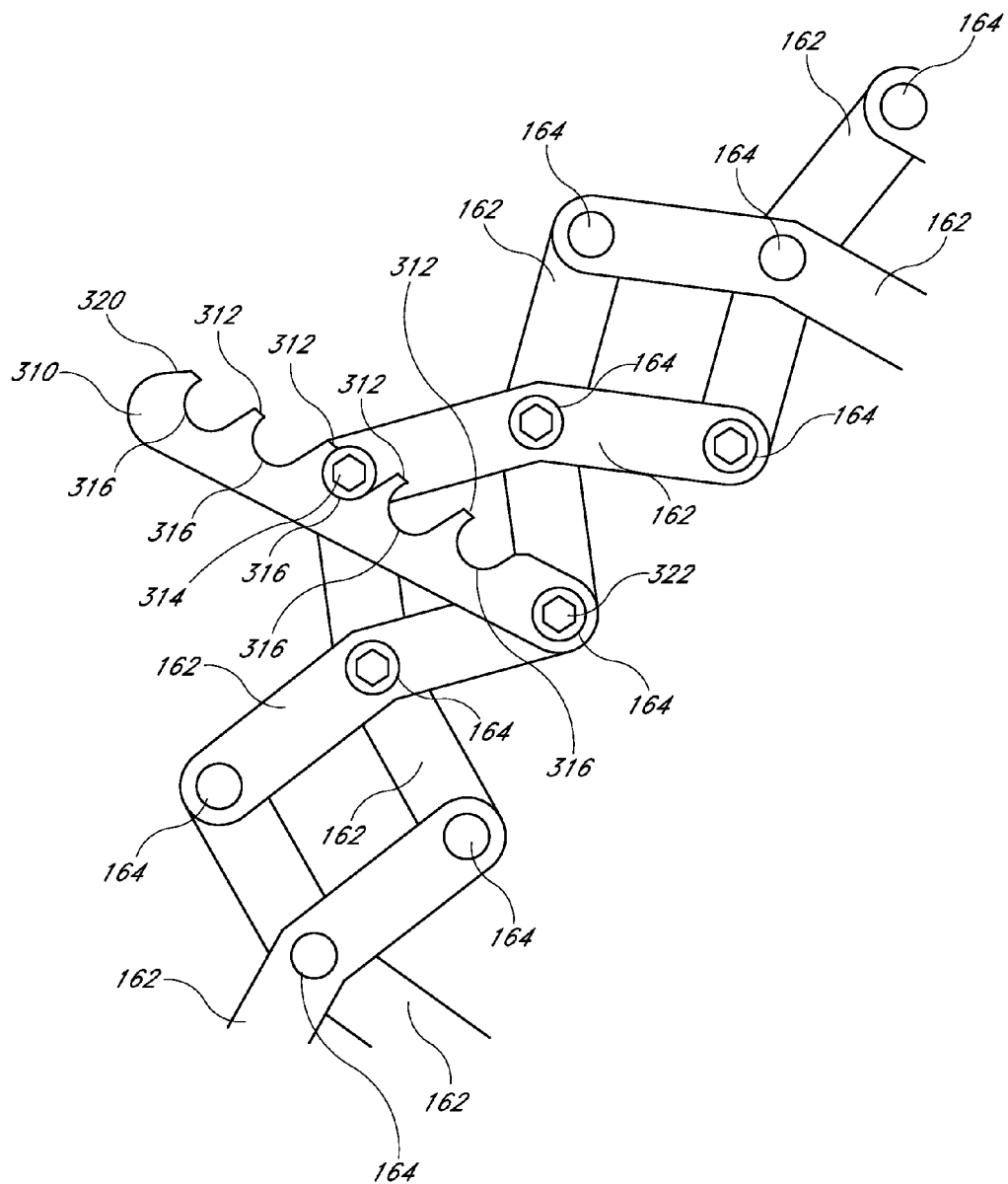
FIG. 32 is a top view of a portion of an expandable ring with a locking mechanism, according to one embodiment.

FIG. 32 illustrates an expandable ring 160 embodiment with a locking mechanism 310. The illustrated locking mechanism 310 is constrained between two pivots. The locking mechanism is rotatably attached to one pivot. The locking mechanism 310 has teeth, which may be ratchet teeth 312. One or more ratchet teeth 312 couple to a protrusion 314 (such as a pin or a protuberance) on a second pivot or on a linkage. In at least one embodiment, the protrusion 314 is a ratchet pawl configured to selectively maintain an expanded configuration by engaging at least a portion of the ratchet teeth 312. The valleys between the teeth 312 are indentations 316. The protrusion 314 is configured to engage at least one indentation 316 to selectively lock the expandable ring 160 in an expanded configuration. Note that placing the protrusion 314 in a different indentation 316 enables different expandable configurations, which have different diameters. Thus, the illustrated embodiment is configured to selectively maintain various expanded configurations.

A release mechanism 320 is configured to disengage the protrusion 314 from the ratchet teeth 312 to enable the expandable ring 160 to return to a collapsed configuration. Pressing on the release mechanism 320 in a direction that is transverse to the longitudinal axis of the locking mechanism 310 pushes the protrusion 314 out of the indentation 316 and away from the ratchet teeth 312. As a result, the locking mechanism 310 no longer constrains the distance between the two pivots and the expandable ring 160 is free to change in diameter.

Other embodiments involve other means of constraining the relative movement of two linkages. In at least one embodiment, an expandable ring's diameter is locked by constraining relative movement between a joint and a linkage. In yet other embodiments, multiple locking mechanisms are used on one expandable ring to reduce the system's dependence on the interrelatedness of the linkages. This approach enables less rigid components to provide sufficient overall rigidity. In one embodiment, the linkages are molded from medical-grade polyetheretherketone (PEEK). In some embodiments, the linkages are machined from a metal such as stainless steel to provide sufficient rigidity and to enable repeated autoclave sterilization.

Figure 33:
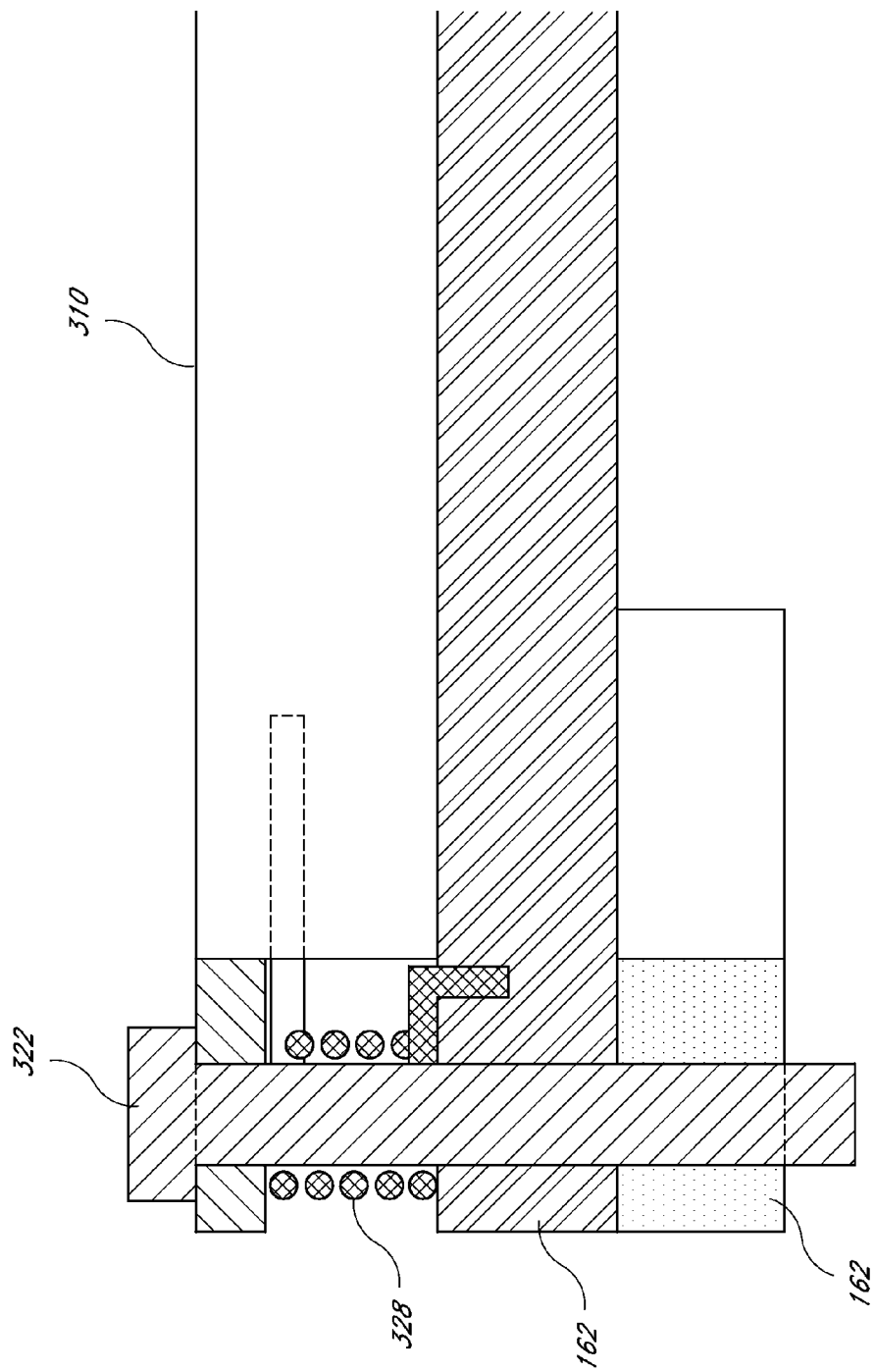
FIG. 33 is a cross-sectional view of a torsion spring and torsion spring pin, according to one embodiment.

Referring now to FIGS. 32 and 33, locking mechanism 310 may be coupled to one pivot with a torsion spring pin 322 to push the teeth 312 towards the protrusion 314. Thus, the torsion spring 328 biases the locking mechanism 310 towards the protrusion 314, which may be on a pivot. The teeth 312 illustrated in FIG. 32 are slanted such that the protrusion 314 readily slips out of the indentations 316 when the expandable ring 160 is expanding, yet the teeth 312 prevent the protrusion 314 from slipping out of the indentations 316 when external forces attempt to collapse the expandable ring 160. Thus, the expandable ring 160 resists compressive forces but allows expansive forces to expand the expandable ring 160. FIG. 33 illustrates a cross-sectional view of the torsion spring 328 and the torsion spring pin 322.

Another embodiment includes a first magnet disposed at the non-pinned end of the locking mechanism 310 and a second magnet disposed near the protrusion 314. The magnets provide the biasing force described above. Although the embodiments illustrated in various figures show the locking mechanism 310 rotatably pinned near the inner diameter of the expandable ring 160, the locking mechanism 310 in other embodiments is rotatably pinned near the outer diameter of the expandable ring 160.

In another embodiment, the locking mechanism is a piston-cylinder apparatus. A check valve prevents fluid from entering the cylinder, which resists tensile forces. This system can be configured to not resist expansion forces to enable easy expansion of the ring structure to cause incision expansion. Alternatively, a valve can be added to selectively resist further expansion. To release the constraint, the valve can be opened, permitting free expansion and collapse. In another embodiment, a rotating latch attached to one pivot, releasably engages another pin by virtue of teeth formed to latch with the pivot. In yet another embodiment, a caulk-gun-style mechanism is employed as the releasable locking mechanism. In this embodiment, the mechanism has higher friction in one direction than in the other direction. The caulk-gun-style mechanism is released by actuating the spring-biased tab or "garage" engaged against the sliding element.

In yet another embodiment, the releasable locking mechanism is a cable, wire, or string that substantially resists tension maintained by a clamp mechanism disposed between one or more pivot points. The tension resisting capability is released by pressing a button on the clamp mechanism, thereby removing the clamping force.

Although several embodiments utilize a bar-like latch, other embodiments utilize dramatically different locking mechanisms. For example, the embodiment illustrated in FIG. 34 has a pivot lock 324, which limits the rotation of a first link 162a and a second link 162b about their connecting pivot. This single pivot lock 324 can lock the diameter of the entire expandable ring. Other embodiments include multiple pivot locks 324. The pivot lock 324 includes a user interface button 326. In one embodiment, the pivot lock 324 enables expansion of the expandable ring 160 but prevents collapse of the expandable ring 160. Pressing the user interface button 326 releases the pivot lock 324 to enable the expandable ring 160 to return to the collapsed configuration 160a. In one embodiment, a pivot lock is constructed through the use of a deformable plug, which increases the rotational friction between links, and thus, constrains the structure's shape. In another embodiment, a rotational ratcheting mechanism is disposed upon the pivot. The rotational ratcheting mechanism has locking teeth engaged in a position to maintain the expandable ring's shape. Pressing a button releases the locking teeth to enable collapsing the ring.

Figure 34:
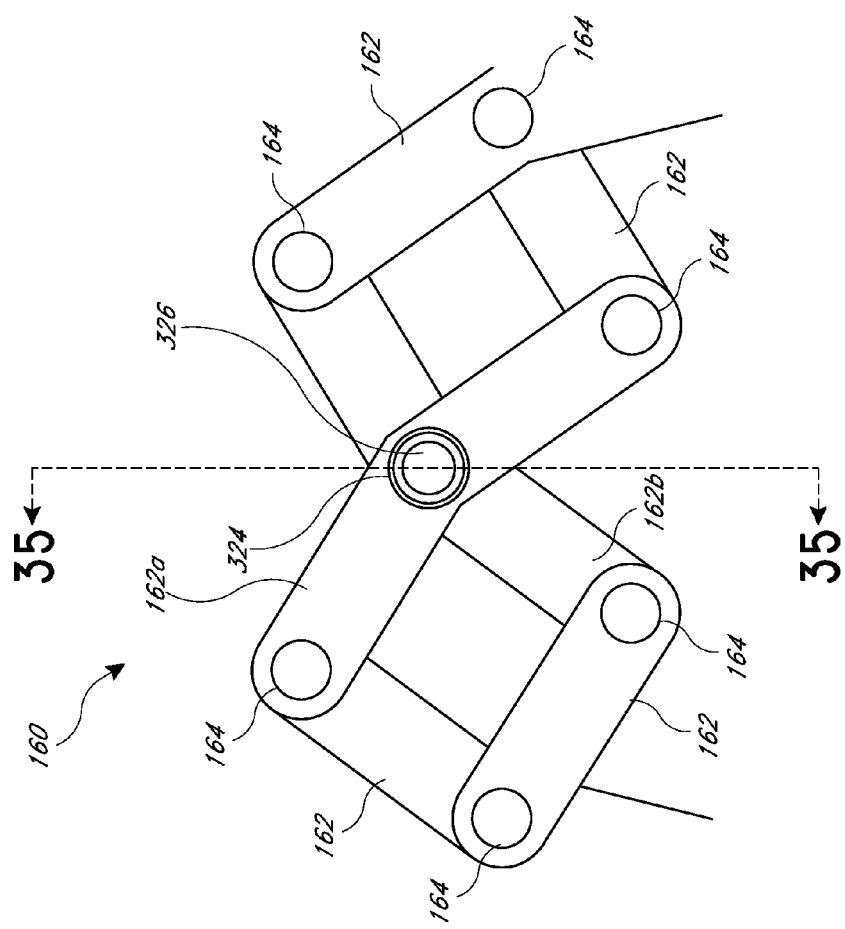
FIG. 34 is a top view of a portion of an expandable ring with a pivot lock, according to one embodiment.
Figure 35:
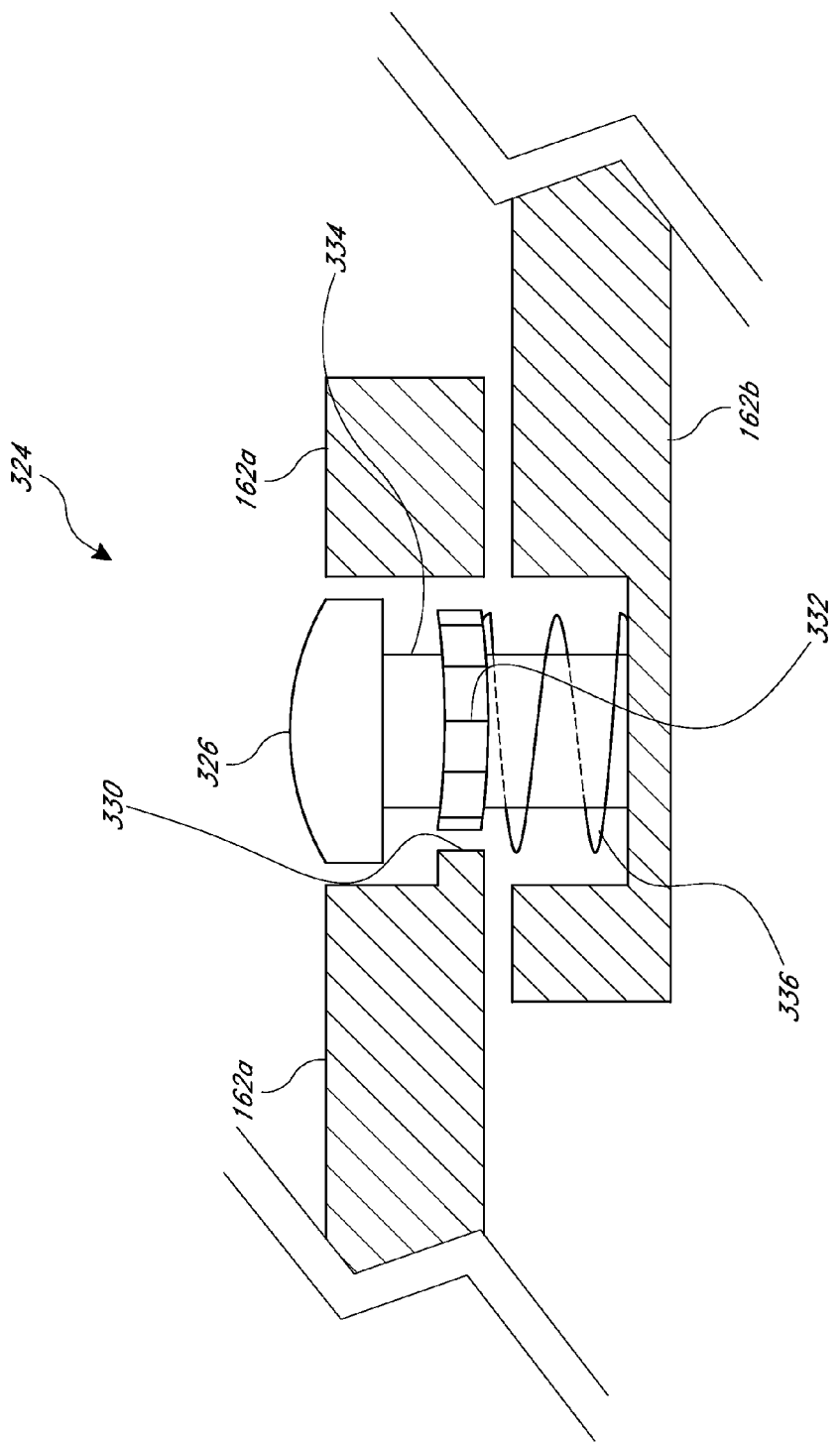
FIG. 35 is a partial cross-sectional view of a pivot lock embodiment.

FIG. 35 illustrates cross section 35 from FIG. 34. In FIG. 35, the first linkage 162a, the second linkage 162b, and the rotational ratchet pawl 330 are shown as cross sections to make the other portions of FIG. 35 visible. (The other portions of FIG. 35 are not shown as cross sections.) The first linkage 162a comprises a rotational ratchet pawl 330. The user interface button 326 comprises rotational ratchet teeth 332 and a reduced diameter zone 334. A spring 336 pushes the user interface button 326 upward to the maximum height of the user interface button 326. When the user interface button 326 is at its maximum height, the rotational ratchet teeth 332 engage the rotational ratchet pawl 330. When the user interface button 326 is pressed downward, the rotational ratchet teeth 332 disengage the rotational ratchet pawl 330 and the rotational ratchet pawl 330 enters the reduced diameter zone 334, which allows the first linkage 162a to rotate freely relative to the second linkage 162b. In one embodiment, the user interface button 326 is coupled to the second linkage 162b such that they cannot rotate relative to each other. In another embodiment, the user interface button 326 is coupled to the second linkage 162b such that such that they cannot rotate relative to each other in one direction, but can rotate relative to each other in the opposite direction.

Figure 36:
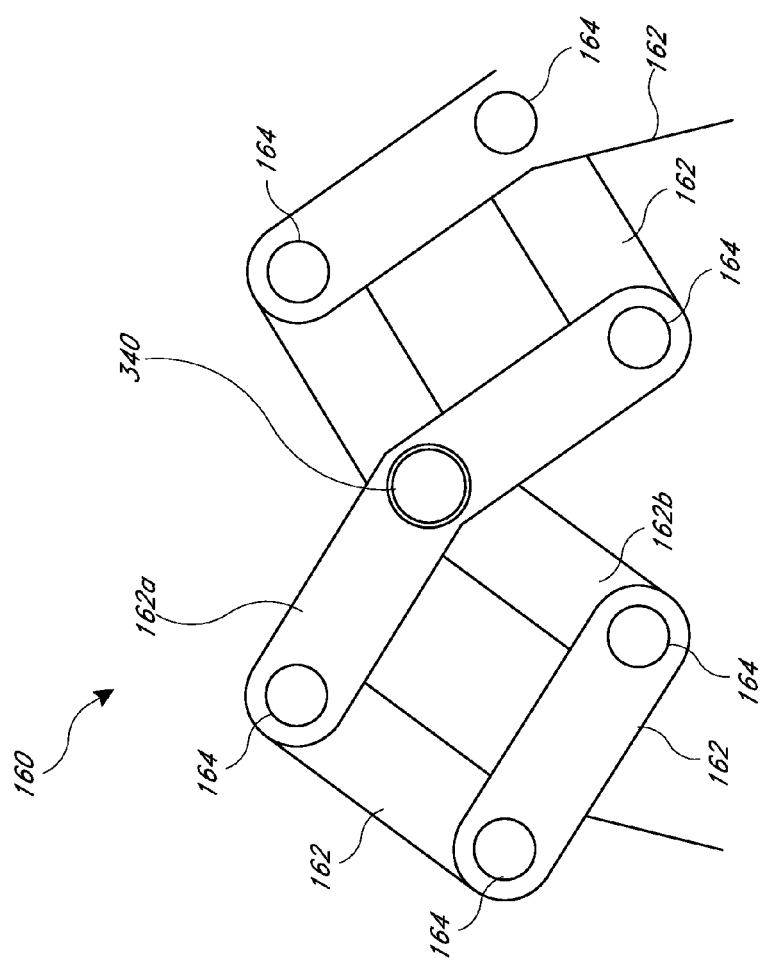
FIG. 36 is a top view of a portion of an expandable ring with a torsion spring assembly that creates a torsional force that expands the expandable ring, according to one embodiment.

FIG. 36 illustrates yet another embodiment. The tissue surrounding the surgical access device places a compressive force on the expandable ring that pushes the expandable ring towards a collapsed position. The torsion spring assembly 340 resists the tissue's compressive force. The rotational force of the torsion spring assembly 340 tends to expand the expandable ring. In practice, the expandable ring naturally goes to its most expanded diameter unless another force resists the torsion spring assembly 340. The physician compresses the expandable ring to facilitate placing the surgical access device into the incision. Once the physician releases the compressive force that she is applying with her hands, the torsional spring assembly 340 causes the expandable ring to expand towards its most expanded diameter while the tissue of the surgical site applies a compressive force. The expansion force of the torsional spring assembly 340 and the compressive force of the tissue reach equilibrium, which typically enables a large enough opening through the surgical access device for the physician to access target tissue.

Some embodiments include multiple torsion spring assemblies 340. One embodiment has torsion spring assemblies 340 at each pivot of the expandable ring 160.

In another embodiment, the expandable ring 160 has two or more discrete stable configurations. In one embodiment, one stable configuration is a substantially collapsed configuration and another stable configuration is an expanded configuration. Such behavior can be implemented using a bistable or over-center mechanism, in which the lowest energy configuration corresponds to these two (or more) desired configurations.

Figure 37:
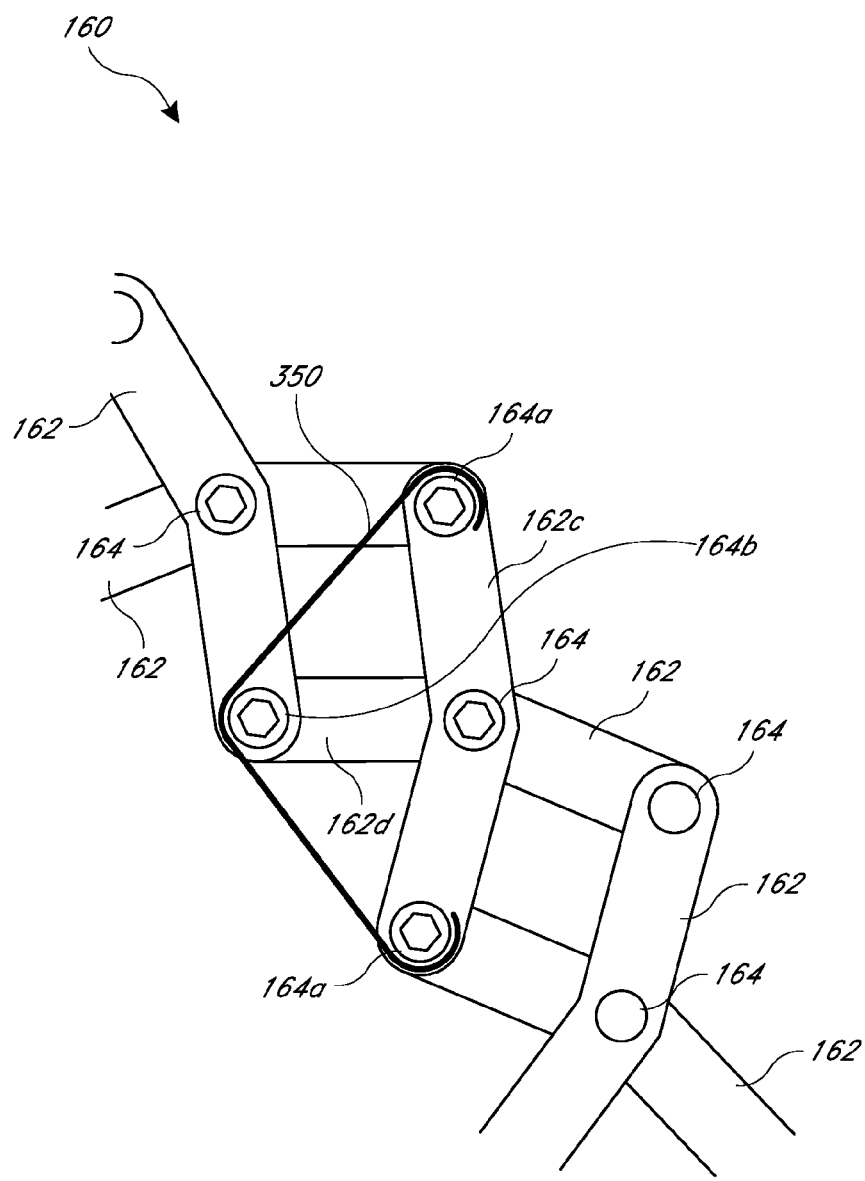
FIGS. 37-38 are top views of a portion of an expandable ring with an elastic member, according to one embodiment.
Figure 38:
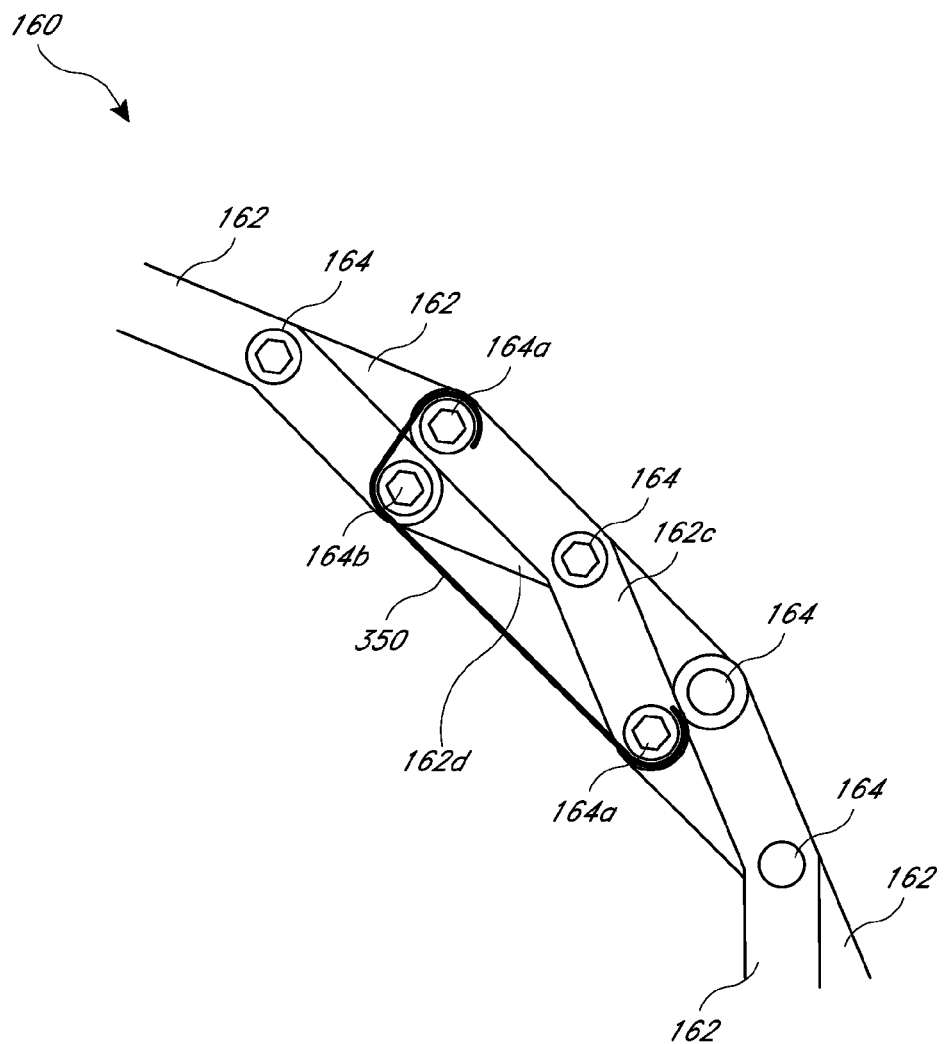

FIGS. 37 and 38 illustrate a portion of an expandable ring 160. In an embodiment with multiple, stable configurations, an elastic member 350 (rubber band, spring, etc.) is disposed about three pivots 164, where two anchor pivots 164a are connected to a primary linkage 162a and a third pivot 164b is connected to a secondary linkage 162d. In one embodiment, each end of the elastic member 350 is anchored to a point such as an anchor pivot 164a and the elastic member 350 stretches about a pivot 164b located along the length of the elastic member 350 between the ends of the elastic member 350 that are anchored as illustrated in FIGS. 37 and 38.

FIG. 37 illustrates a partially expanded configuration. FIG. 38 illustrates a fully expanded configuration. Note how the overall length (and therefore the stored energy) of the elastic member 350 passes through a maximum as the device is extended, leaving two low-energy geometric configurations that correspond to the desired configurations of the expandable ring 160.

Figure 39:
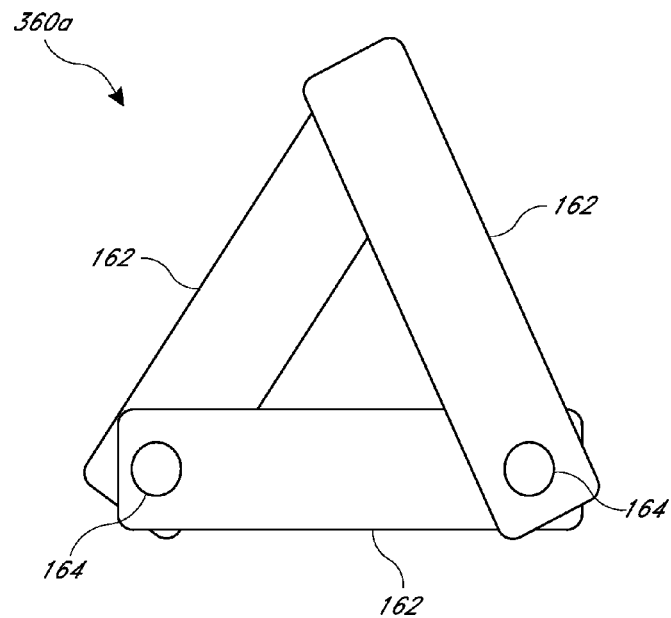
FIGS. 39-40 are top views of a retention member, according to one embodiment.
Figure 40:
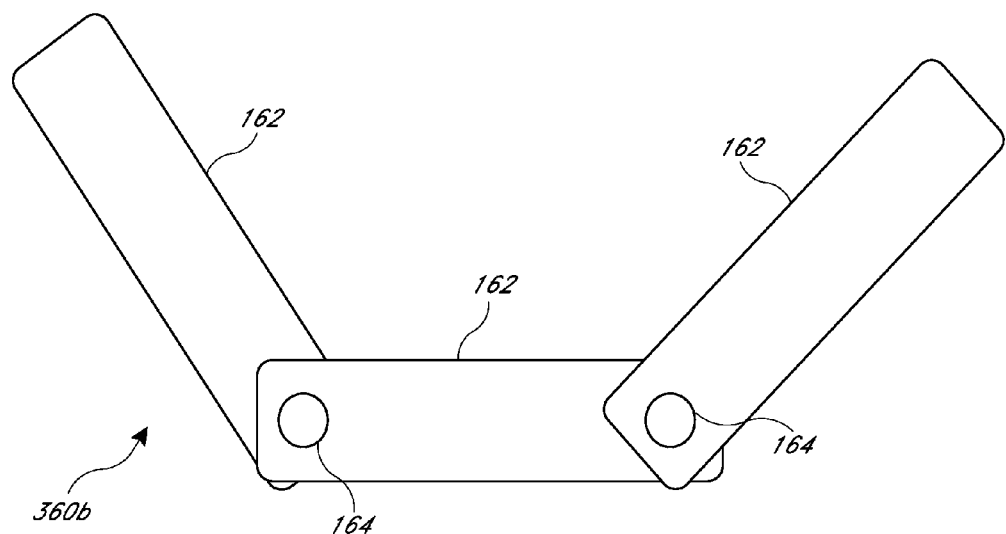

FIGS. 39-40 illustrate an embodiment of a second retention member 360a,b configured to expand from a collapsed configuration 360a to an expanded configuration 360b. The second retention member 360a,b comprises at least three linkages 162 pivotably coupled to one another by pivots 164 such that expanding the second retention member 360a,b causes the linkages 162 to pivot relative to each other. The embodiment illustrated in FIGS. 39-40 is an open shape and is an example of a "C" shape. Some "C" shaped embodiments include curved linkages that may form a shape that is closed in a collapsed configuration and open in an expanded configuration. Other embodiments of retention members include retention rings of diverse shapes including the closed shapes illustrated in FIGS. 9a-9d. Yet other retention member embodiments include retention frames. The second retention member 360a,b illustrated in FIGS. 39-40 is an example of a retention frame, although other second retention member embodiments are not retention frames.

Figure 41:
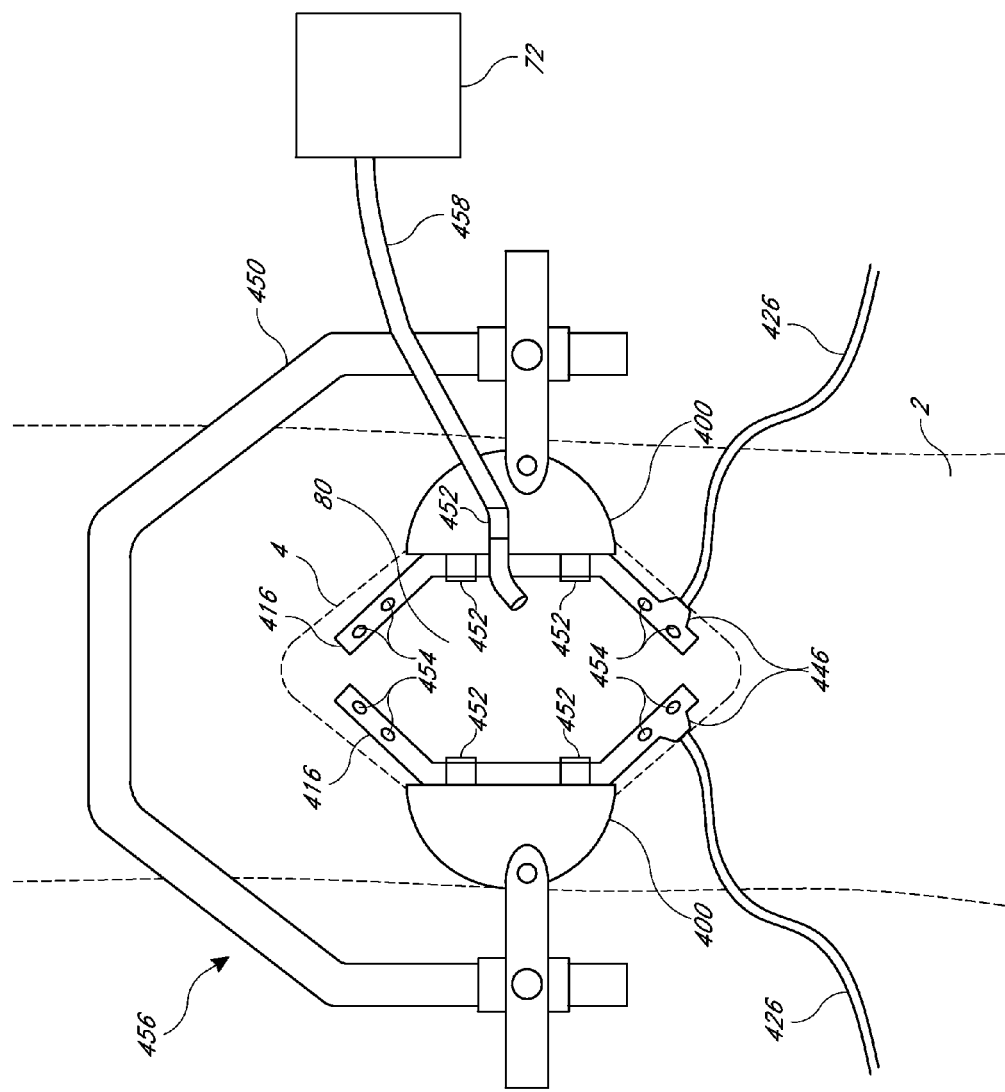
FIG. 41 is a top view of an embodiment with two retention members coupled by a connector.

FIG. 41 illustrates an embodiment wherein two retention members 400 expand an incision 4 to facilitate access to a target site 80. The retention members 400 are coupled by a connector 450. The illustrated connector 450 and retention members 400 are stainless steel to provide rigidity and reusability. A fluid delivery member 416 is coupled to each retention member 400. Each fluid delivery member 416 has openings 454 to allow fluid (not shown) to exit the surgical access system 456 to irrigate the surgical site. The illustrated fluid delivery members 416 are made from silicone, are disposable, and clip to the retention members 400. The "C" shaped clips 452 are welded to the retention members 400 and are sized to receive the fluid delivery members 416. Each fluid delivery member 416 is coupled to a fluid delivery tube 426 or to another means of delivering fluid via a fluid delivery inlet 446. Fluid can flow though the fluid delivery tubes 426, through the fluid delivery inlets 446, through the fluid delivery members 416, out of the openings 454, and into the target site 80. Other embodiments include more than two retention members 400 and components that are shaped differently than illustrated in FIG. 41.

The surgical access system 456 embodiment illustrated in FIG. 41 can also include a fluid removal member 458 that is in fluid communication with a medical suction device 72. The fluid removal member 458 can be a silicone tube that is coupled to the surgical access system 456 by a "C" shaped clip 452. The fluid removal member 458 is configured to remove fluid from the surgical site.

In one embodiment, the surgical access system 456 does not have means to irrigate the surgical site but does have means to remove fluid from the surgical site. An example embodiment does not include fluid delivery members 416 but does include at least one fluid removal member 458. In several embodiments, connecting a surgical access device to a rigid frame or to a structure rigidly connected to another rigid structure, such as a surgical bed, may be advantageous. Connecting a surgical access device to a rigid structure can assist the surgeon in moving the surgical field access to a different location to provide easier access to different body tissues that need to be manipulated during surgery. As described above, the surgical device can be locked into a rigid structure that may be free to move to different locations or may be fixed in one location by attaching the rigid structure to a rigid adaptor configured to connect the locked device to a frame. In some embodiments, the frame is part of the surgical bed such that the surgical access device can be immobilized relative to the surgical bed.

Figure 42:
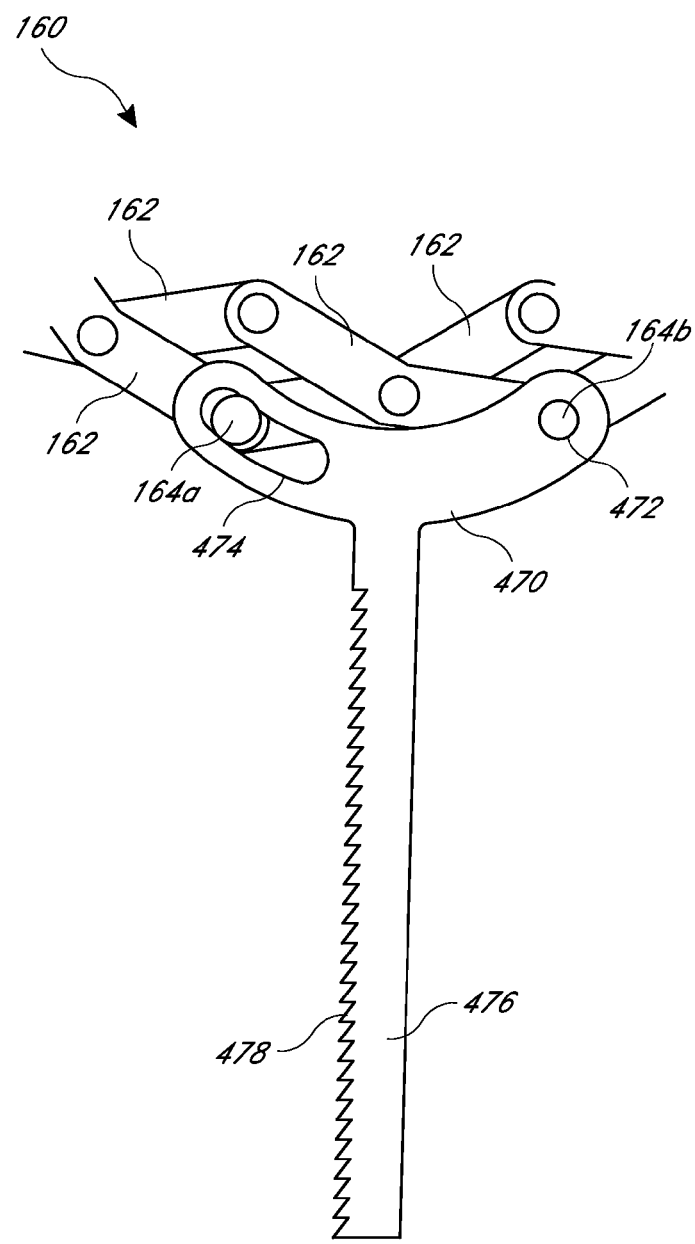
FIG. 42 is a top view of an adapter member that connects to pivots, according to one embodiment.

As shown in FIG. 42, an exemplary embodiment of this approach is an adaptor member 470 that connects to two of the pivots 164a,b of the surgical access device 8m (shown in FIG. 22). The two engagement features on the adaptor member 470 are a hole 472 and a slot 474. The hole 472 engages a first pivot 164b and the slot 474 engages a second pivot 164a. In this embodiment, the surgical access device 8m can lock in a plurality of expanded configurations. Thus, the distance between the first pivot 164b and second pivot 164a can change. Therefore, the slot 474 allows the adaptor member 470 to engage the second pivot 164a regardless of varying expanded configurations. In one embodiment, the hole 472 for the first pivot 164b is used to constrain the device in translation, and slot 474 configured for the second pivot 164a is used to constrain the surgical access device 8m in rotation about said first pivot 164b.

Figure 43:
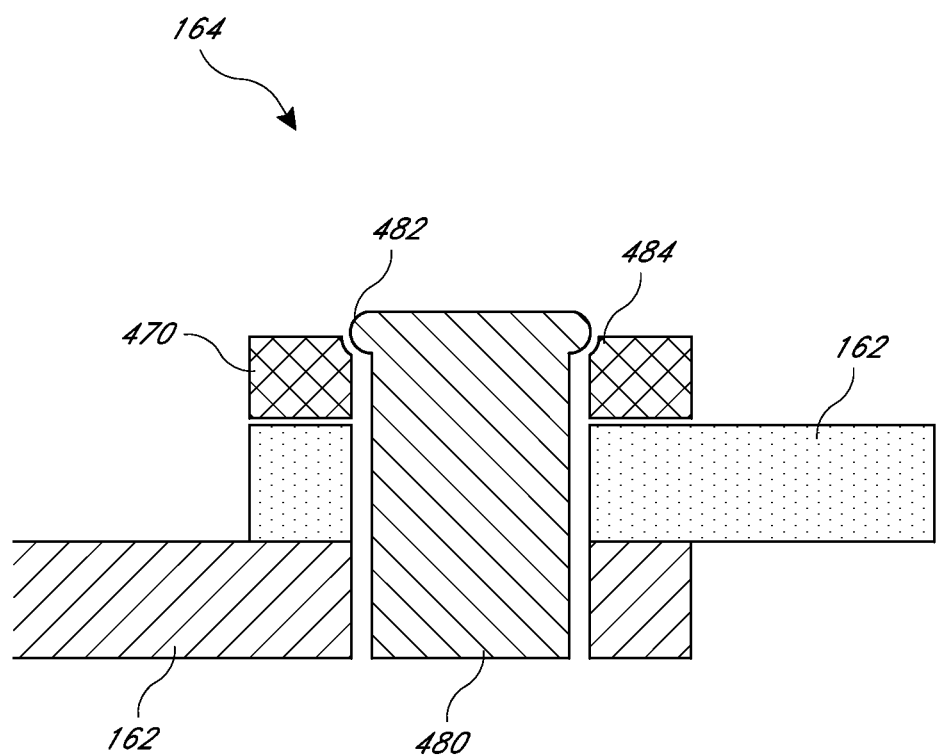
FIG. 43 is a cross-sectional view of an interface between an adapter member and a pivot, according to one embodiment.

As shown in FIG. 43, the interface between adaptor member 470 and pivots 164 can include a radial protrusion 482 on pivot post 480 and an indentation 484 on the adaptor member 470 to constrain the adapter member 470 to the pivots 164 as well as facilitate simple assembly and disassembly when needed during a surgical procedure. In some embodiments, this engagement means is additionally beneficial because the surgical access device 8m may need to be selectively anchored in different locations with different pivots 164 throughout a case.

The entire contents of U.S. Pat. No. 4,254,763, entitled SURGICAL RETRACTOR ASSEMBLY, and filed Jun. 7, 1979 are incorporated herein by reference. A rigid frame, such as shown in U.S. Pat. No. 4,254,763, can be a surgical device that is rigidly attached to a surgical bed to provide a plurality of attachment surfaces and locations for various surgical retractors used within a surgery. The retractor allows a surgeon to easily attach and remove retraction members using a ratchet pawl member that connects the retractor to the frame.

Referring now to FIGS. 6-7 of U.S. Pat. No. 4,254,763, one embodiment of a ratchet pawl member is shown as element 72. The ratchet pawl member 72 can have an opening 78 for accepting a member with ratchet teeth and a spring-loaded ratchet pawl 79 for engaging said ratchet teeth to selectively maintain the relative location of the two members.

Referring now to FIG. 42 in this document, the end opposite the pivot engagement hole 472 and slot 474 can include a post 476 and ratchet teeth 478 configured for acceptance into ratchet pawl member 72 (shown in U.S. Pat. No. 4,254,763).

In surgical use, adapter member 470 can be attached to the surgical access device 8m as described above and then positioned as desired relative to the surgical incision. A ratchet pawl member can then be attached to a rigidly fixed retractor such as a Bookwalter retractor. Post 476 on adapter member 470 can then be placed within the opening of a ratchet pawl member to engage the ratchet pawl and ratchet teeth. The post 476 can be moved relative to the ratchet pawl member until the surgical access device, and therefore, the surgical field access, is in the desired location.

Figure 44:
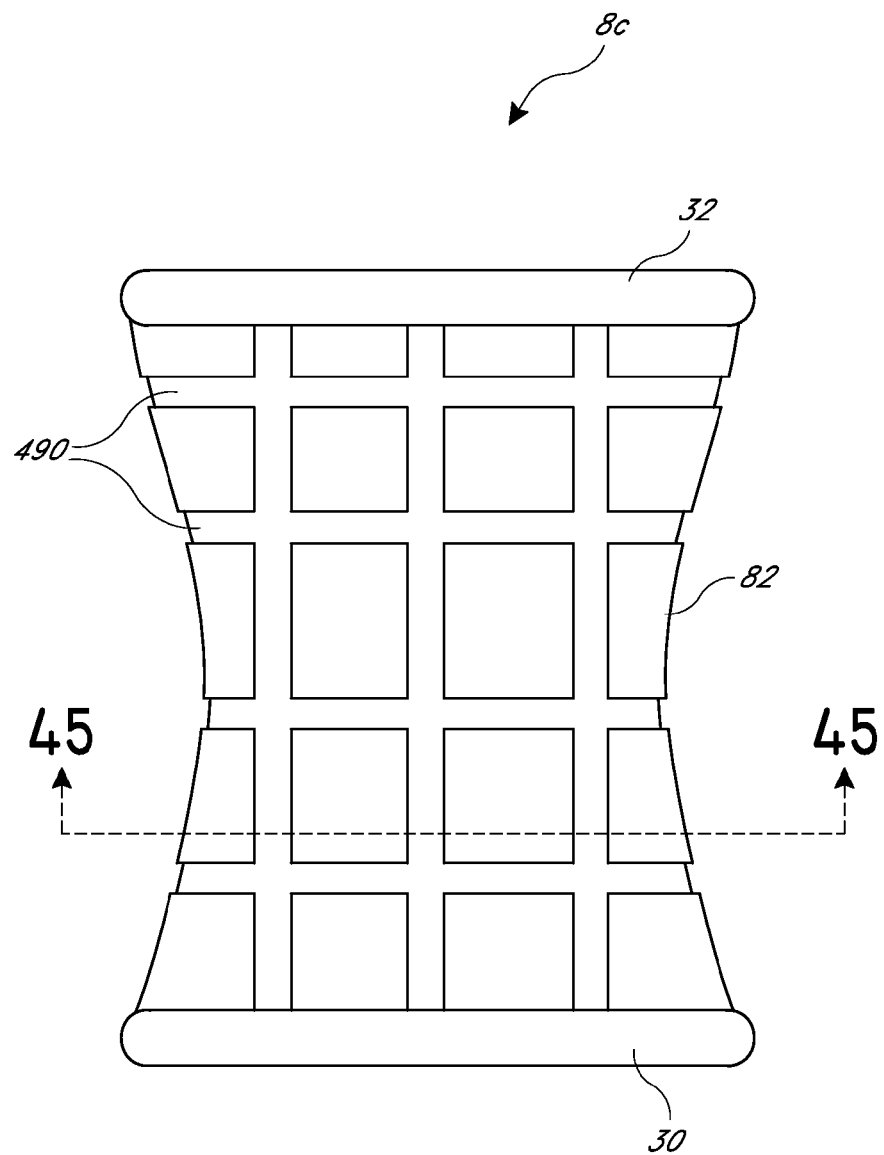
FIG. 44 is a side view of a surgical access device with channels, according to one embodiment.
Figure 45:
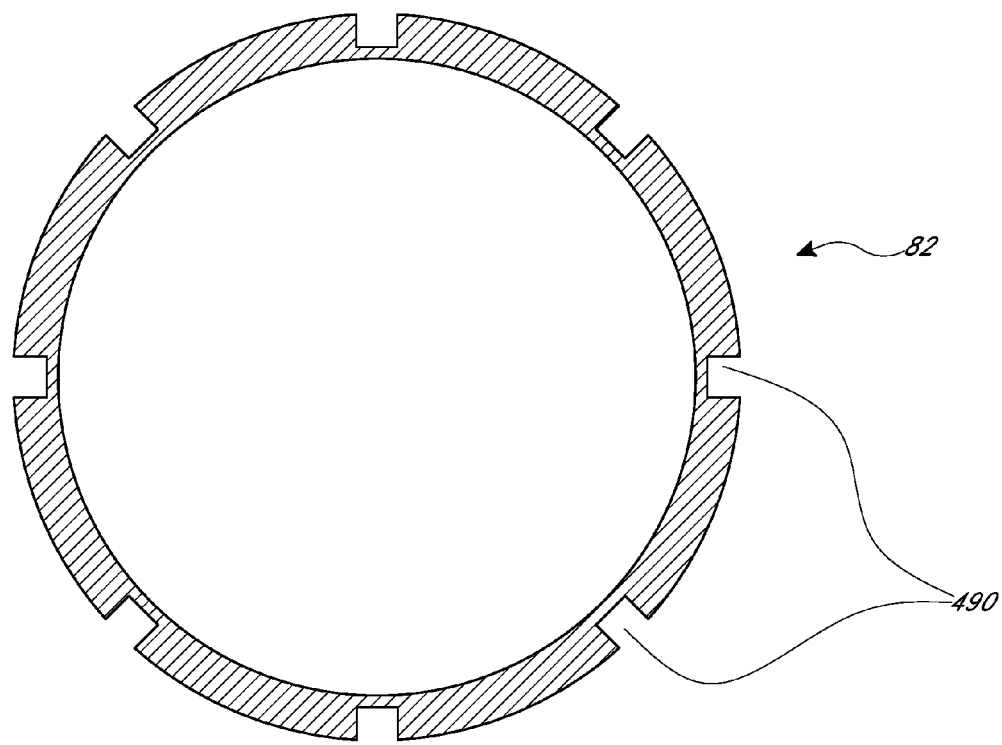
FIG. 45 is a cross-sectional view of the embodiment shown in FIG. 44.

Referring now to FIGS. 44-45, in some embodiments, the surgical access device 8c can contain a sheath 82 that comprises channels 490 to deliver fluid to a surgical site. The channels 490 illustrated in FIGS. 44-45 are external channels, although some embodiments include internal channels. Sheath 82 can be a unitary structure, such as a film or sheet, with one or more external-facing channels 490. In some embodiments, the sheath 82 is a non-unitary structure. Channels 490 can deliver fluid along their length and expose the abutting surgical site tissue to fluid. This embodiment can expose a significant surface area of the surgical site to a fluid. The channels 490 can be disposed at any angle. Other embodiments include hundreds of channels. Several embodiments include channels that intersect with each other to further enhance fluid delivery. The depth of a channel 490 can be configured so as to maintain a patent channel even with retraction forces applied to the sheath 82. Various embodiments include channels that are 0 to 0.1 inches deep, 0.1 to 0.35 inches deep, and 0.2 to 0.5 inches deep. Several embodiments include channels having different depths or channels of varying depths. Channels 490 can be embossed onto sheath 82 using manufacturing processes such as hot embossing or thermoforming. Not all channels 490 are labeled in FIGS. 44-45 to make the Figures easier to see. The channels 490 illustrated in FIGS. 44-45 have similar shapes, although other embodiments comprise channels with different shapes.

Figure 46:
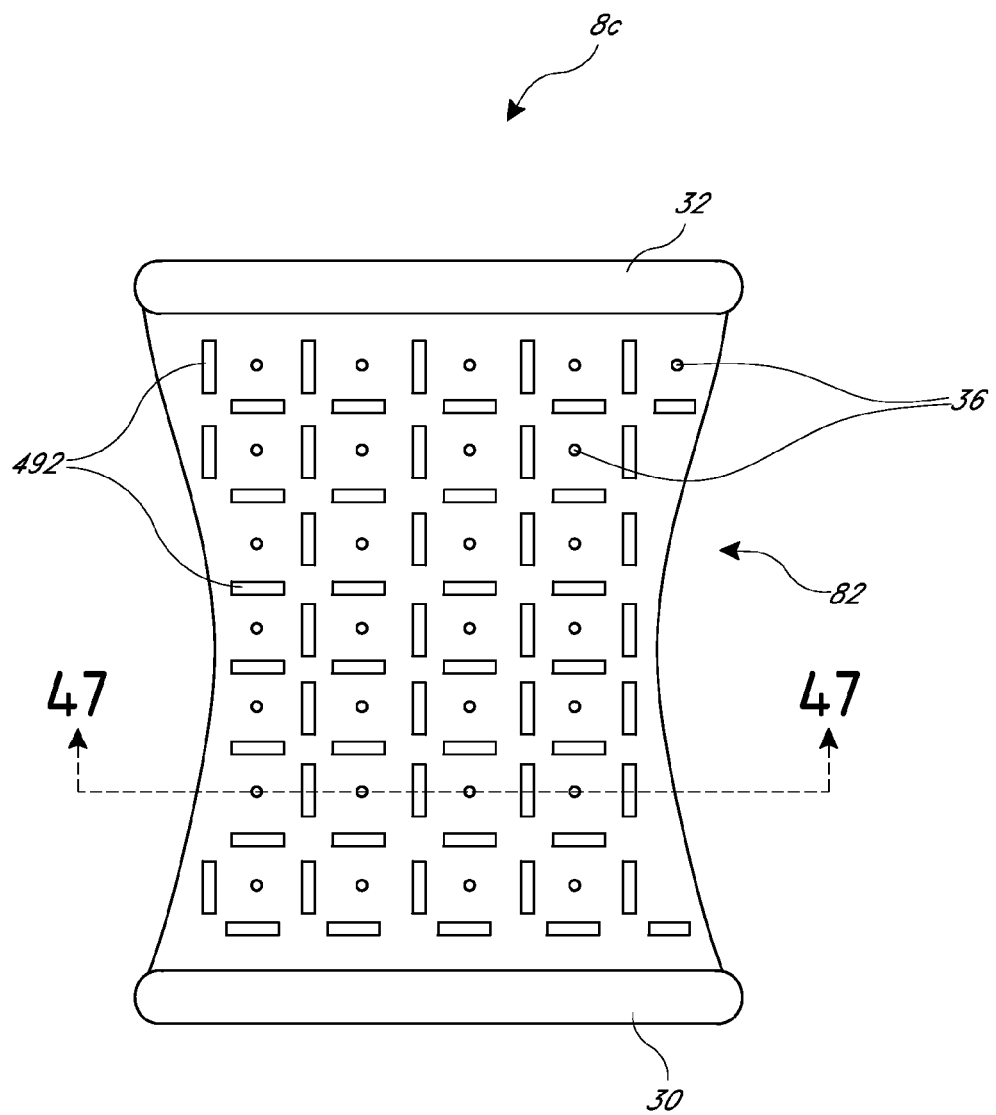
FIG. 46 is a side view of a surgical access device with joined layers, according to one embodiment.
Figure 47:
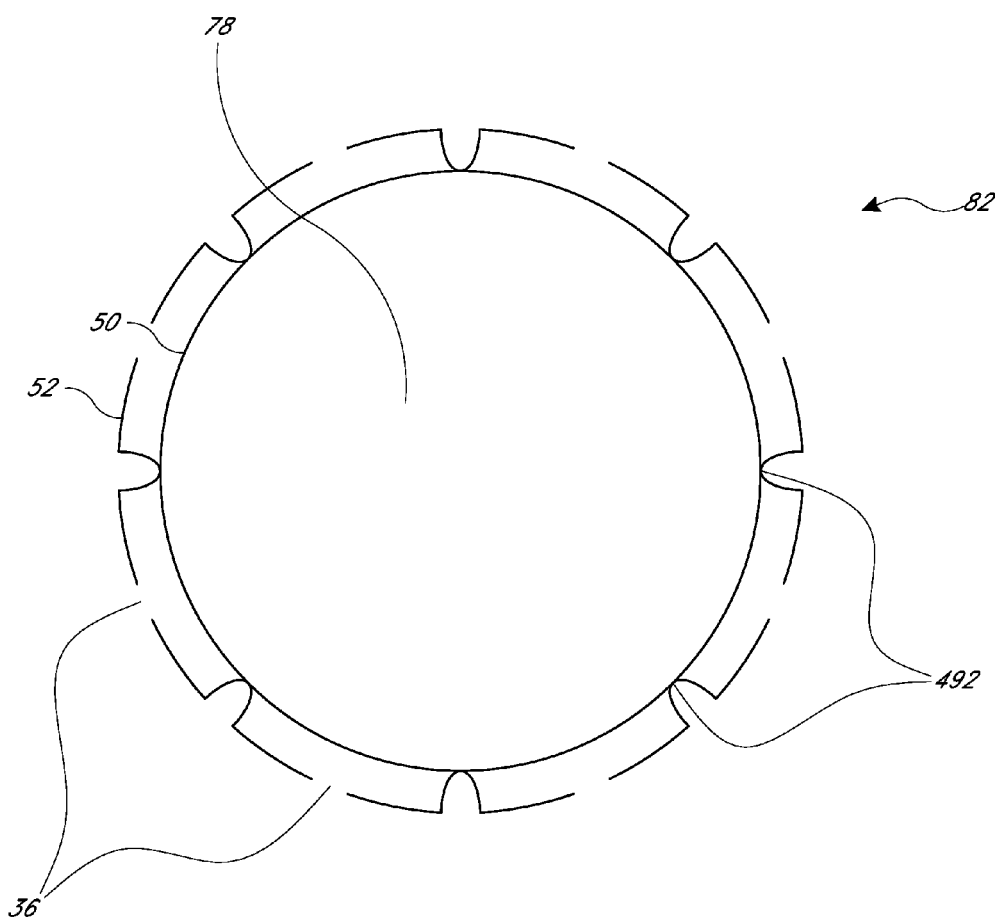
FIG. 47 is a cross-sectional view of the embodiment shown in FIG. 46.

Referring now to FIGS. 46-47, a sheath 82 can comprise an inner layer 50 and an outer layer 52. The outer layer 52 can comprise a plurality of perforations 36. Several embodiments include 25 to 2,000 perforations. The inner layer 50 and the outer layer 52 can be joined to each other in distinct locations 492 to prevent the layers from separating from each other in the joined areas. This separation can cause the inner layer 50 to deflect into central channel 78 of the device and reduce the cross sectional area of channel 78. The joined locations 492 can be created by heat sealing, radio frequency welding, ultrasonic welding, or by using an adhesive to join the inner layer 50 and the outer layer 52. Joined locations 492 can be linear, curved, or of any advantageous profile to reduce the ability of the sheath to separate. Joined locations 492 can be comprised of a repeated pattern of one or more joined area shapes. Joined locations 492 can be different lengths and widths. Joined locations 492 can be seals.

The inner layer 50 and the outer layer 52 illustrated in FIG. 46 are quilted together. Quilted together means that the inner layer 50 and the outer layer 52 are joined at over three locations disposed between the distal and proximal ends of the sheath 82. In several embodiments, the inner layer 50 and the outer layer 52 are joined at 3 to 10 locations, 10 to 20 locations, 20 to 200 locations, and over 200 locations. The joined locations 492 can be spaced at regular or irregular intervals. Not all joined locations 492 and perforations 36 are labeled in FIGS. 46-47 to make the Figures easier to see. The joined locations 492 are illustrated as rectangles, although other joined location 492 shapes are used in other embodiments. Perforations 36 are depicted as circles, although other perforation 36 shapes are used in other embodiments.

Figure 48:
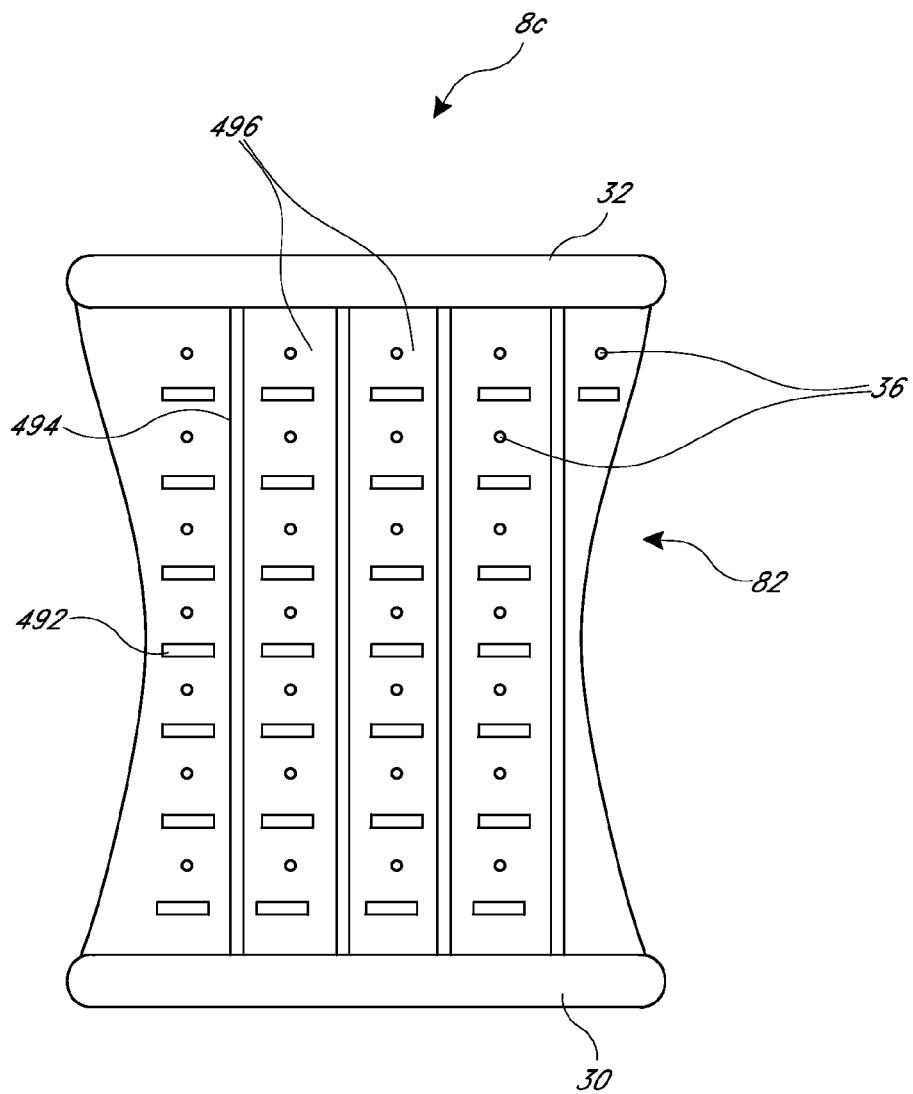
FIG. 48 is a side view of a surgical access device wherein a joined length generally isolates one perforation from another perforation, according to one embodiment.
Figure 49:
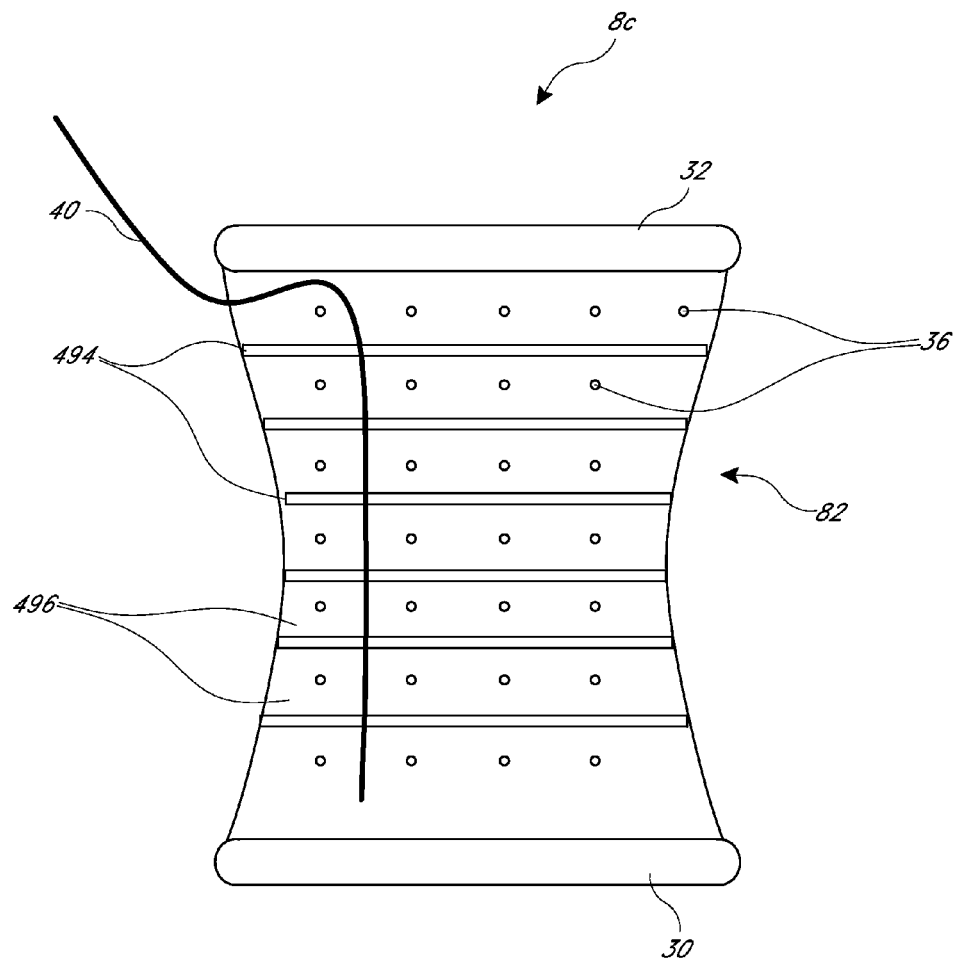
FIG. 49 is a side view of another embodiment wherein joined lengths generally isolate one perforation from another perforation.

Referring now to FIGS. 48-49, joined lengths 494 can be used to isolate one or more perforations from one or more other perforations. The joined lengths 494 can define chambers 496 in which fluid can pass within but cannot pass beyond. In other words, several embodiments include chambers 496 that are sealed from one another such that fluid cannot pass from one sealed chamber to another sealed chamber without exiting the perforations 36. Additional joined locations 492 can be included to prevent separation of the inner layer 50 and outer layer 52 within the chambers 496. Chambers 496 can be oriented in a direction substantially perpendicular to or parallel to or oblique to the axis of the central channel 78 of the surgical access device 8c. In one embodiment, inlet conduit 40 is a tube with holes 130 (see FIG. 15) along the tube's entire distal end or along a portion of the distal end. Inlet conduit 40 can be configured such that it passes through each chamber 496 to supply fluid to each chamber such that the inlet conduit 40 is in fluid communication with each chamber 496. In several embodiments, one or more holes 130 of the inlet conduit 40 are in fluid communication with each chamber 496 such that fluid can generally reach each perforation 36.

Figure 50:
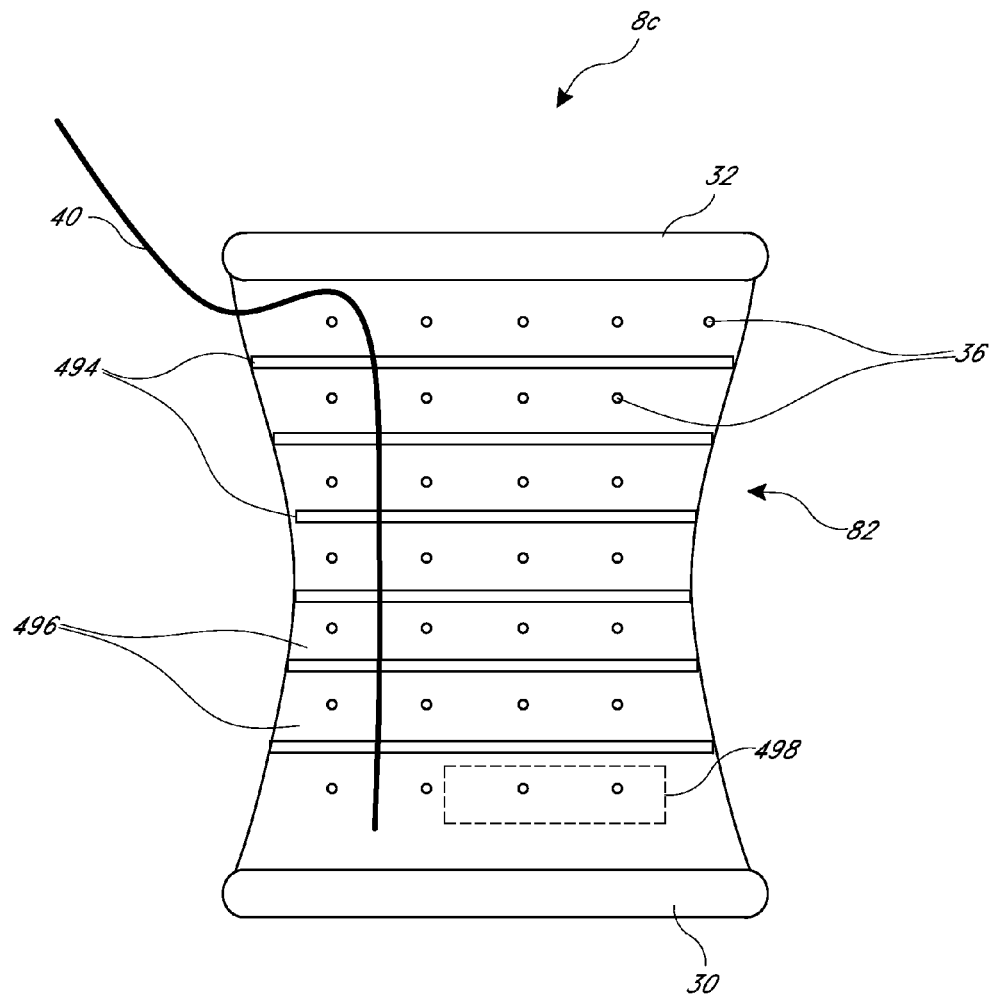
FIG. 50 is a side view of a surgical access device wherein a member is disposed inside a chamber to maintain the chamber's patency, according to one embodiment.

As shown in FIG. 50, a compressible member 498, such as a piece of foam or other porous material or non-porous material, can be disposed within chambers 496 to maintain patency under a compressive force such as those present during surgical retraction. The compressible member 498 can help hold a chamber 496 open to facilitate fluid flow, which may have the purpose of irrigation or fluid removal. Other embodiments include at least one compressible member 498 in each chamber 496. In several embodiments, member 498 is an incompressible member configured to prop open a chamber 496. The member 498 is illustrated with dashed lines because it is located inside the sheath 82. In other embodiments, the member 498 is located outside of the sheath 82.

Figure 51:
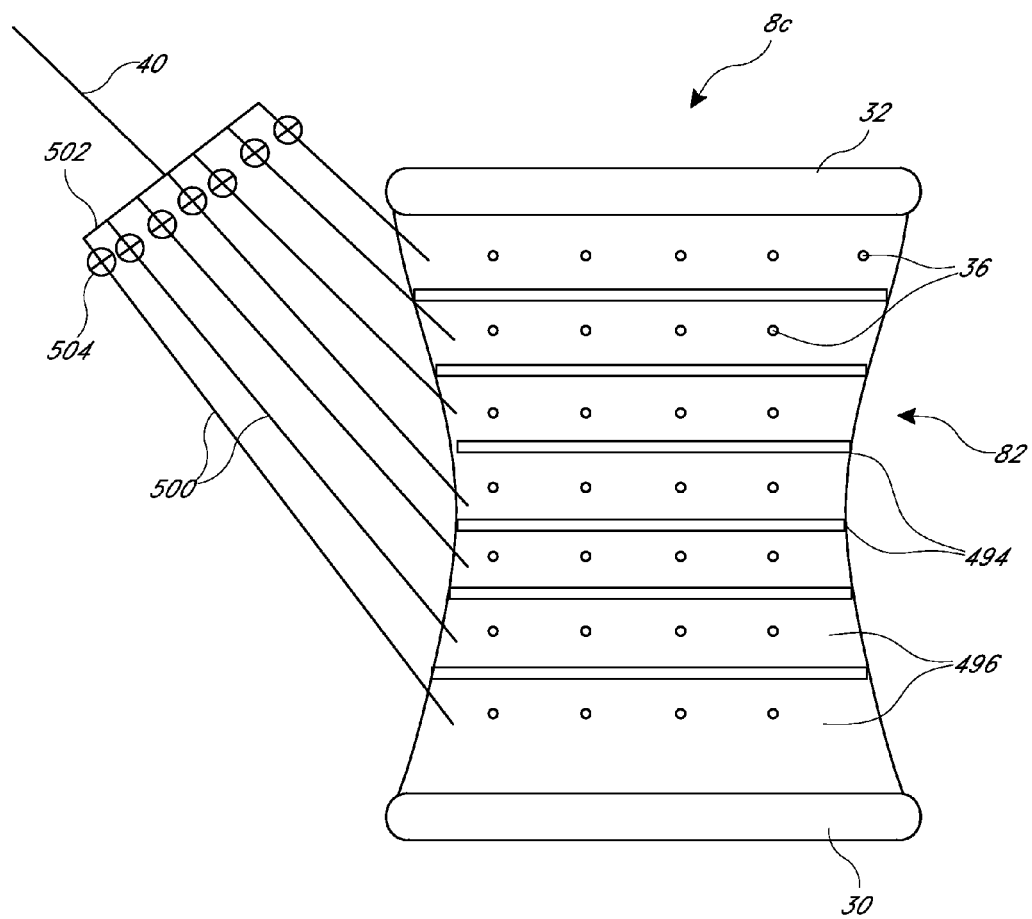
FIG. 51 is a side view of a surgical access device with selective fluid delivery, according to one embodiment.

As illustrated in FIG. 51, flow to each chamber 496 defined by joined lengths 494 can be controlled to selectively deliver fluid to one or more perforations 36 in the sheath 82. In several embodiments, this configuration is advantageous to selectively deliver fluid to perforations 36 that substantially contact the surgical site. In one embodiment, fluid delivery member 40 can comprise a plurality of tubes 500 whose distal ends are in fluid communication with different chambers 496. The chambers 496 can be oriented in a direction substantially perpendicular to or parallel to or oblique to the axis of the central channel 78 of the surgical access device 8c. The tubes 500 can be connected to a manifold 502 with a series of valves 504, such as needle valves or gate valves, that control flow to one or more tubes 500. In some embodiments, a surgeon can, at the time of operation, open one or more valves 504 to deliver fluid to one or more tubes 500 and, therefore, to one or more chambers 496 and perforations 36. Thus, the surgeon can deliver fluid to some perforations 36 while not delivering fluid to other perforations 36.

Figure 52:
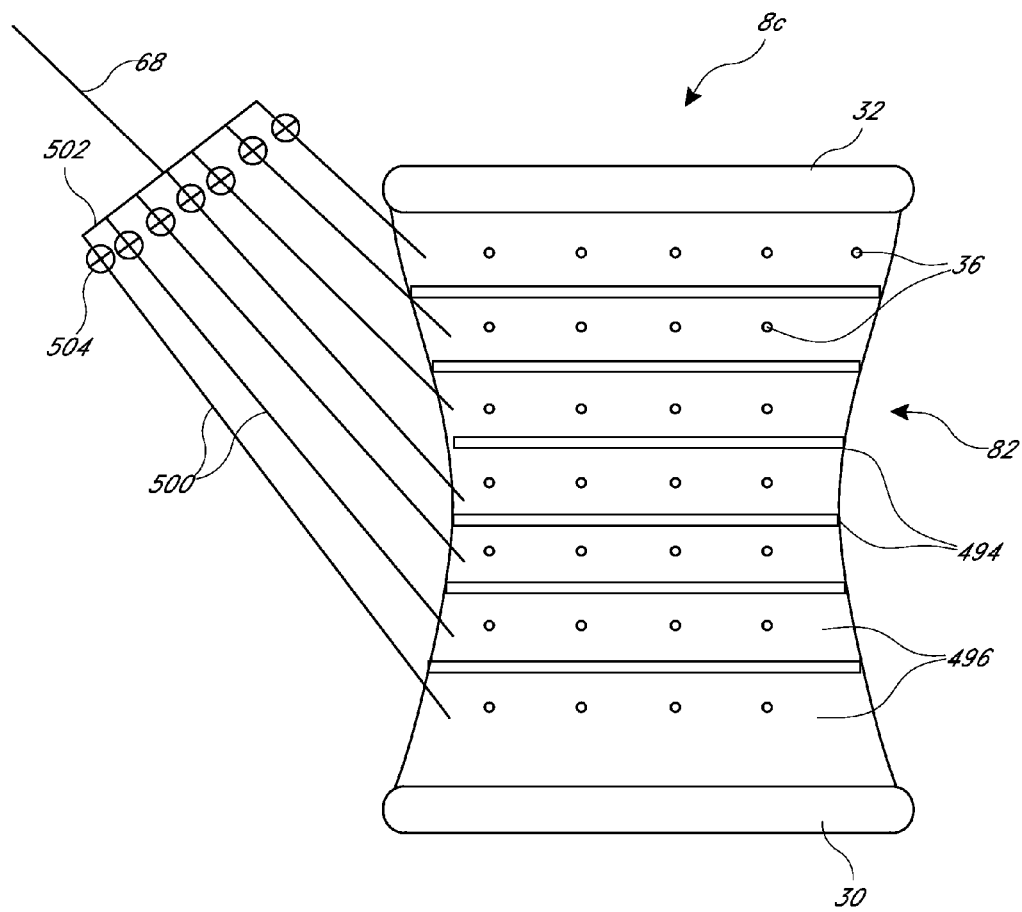
FIG. 52 is a side view of a surgical access device with selective fluid removal, according to one embodiment.

As illustrated in FIG. 52, chambers 496 defined by joined lengths 494 can additionally be used to apply suction to the surgical access device 8c and to remove fluid from the surgical site through perforations 36. An outlet conduit 68 can be connected to a medical suction device 72 (see FIG. 4) on a proximal end (not shown) and a manifold 502 on a distal end. The manifold 502 can comprise one or more valves 504 connected to tubes 500 to selectively apply suction to one or more chambers 496. The surgeon can, at the time of operation, open one or more valves 504 to remove fluid from one or more tubes 500, and therefore, to remove fluid from one or more chambers 496 via perforations 36.

Figure 53:
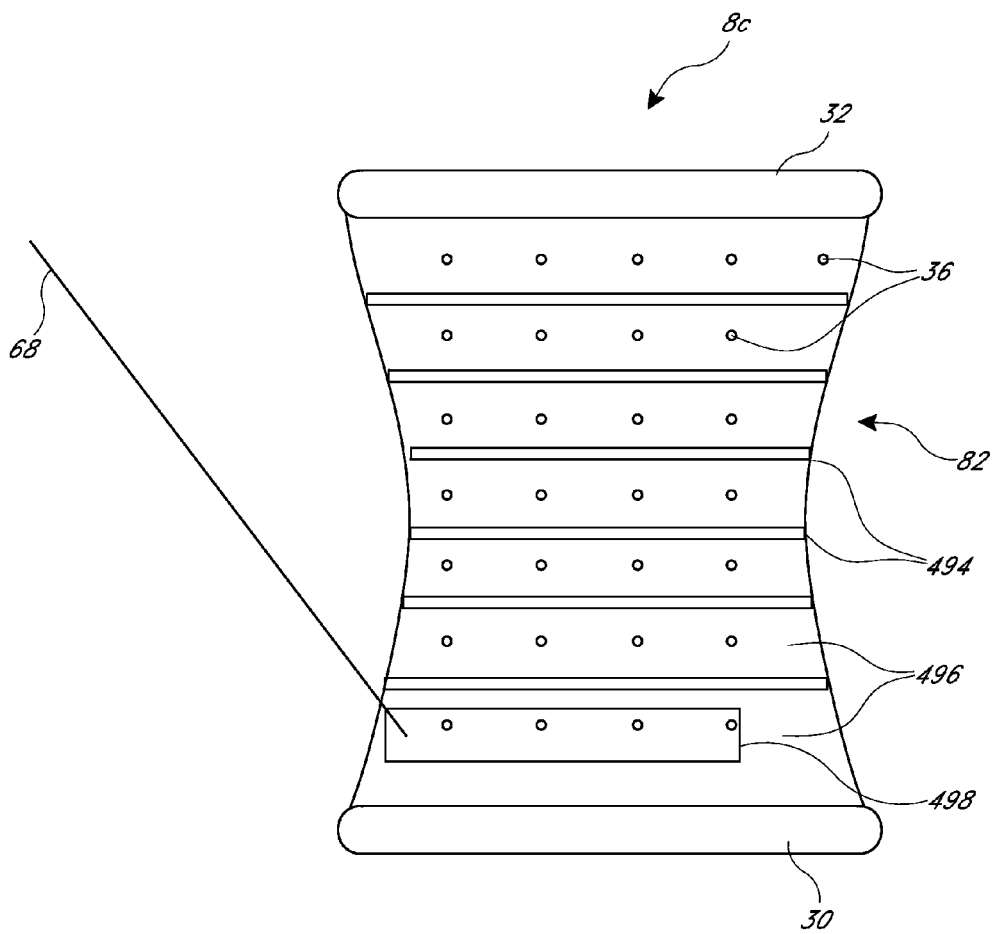
FIG. 53 is a side view of a surgical access device wherein a member is disposed inside fluid removal chamber to maintain the chamber's patency, according to one embodiment.

As illustrated in FIG. 53, a compressible member 498, such as a piece of foam or other porous material or non-porous material, can be disposed between inner layer 50 and outer layer 52 and within a chamber 496 to maintain patency under a compressive force such as negative gauge pressure (e.g., suction) and additionally retraction forces present during surgery. Additionally, the outlet conduit 68 may be connected to one or more chambers 496 in the surgical access device 8c.

Not all perforations 36, joined locations 492, joined lengths 494, chambers 496, tubes 500, and valves 504 are labeled in FIGS. 48-53 to make the Figures easier to see.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

The term "up to about" as used herein has its ordinary meaning as known to those skilled in the art and may include 0 wt. %, minimum or trace wt. %, the given wt. %, and all wt. % in between.

Elements or components shown with any embodiment herein are exemplary for the specific embodiment and may be used on or in combination with other embodiments disclosed herein.

While the invention is susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives thereof.

What is claimed is:

1. A method for retracting tissue in a surgical site in a body, the method comprising:
    inserting at least a portion of a surgical access device into an incision, wherein the surgical access device comprises a first retention member, a second retention member, a pliable membrane comprising an inner layer and an outer layer with a space therebetween, the pliable membrane coupled to the first retention member and the second retention member, and a fluid delivery inlet configured to be placed in fluid communication with the pliable membrane;
    advancing the first retention member into the body through the incision;
    placing the second retention member outside the body;
    retracting the tissue using the pliable membrane;
    introducing fluid into the fluid delivery inlet such that the fluid flows through the space and exits an opening in a lateral surface of a first portion of the pliable membrane and the introduced fluid contacts a wall of the surgical site; and
    suctioning at least a portion of the fluid after the fluid contacts the wall of the surgical site through a second portion of the pliable membrane not in direct fluid communication with the first portion, wherein the suctioned fluid enters the pliable membrane at a location disposed between the first and the second retention members.

2. The method of claim 1, wherein a fluid conduit member is coupled to the first retention member and the method further comprises suctioning the fluid into the fluid conduit member and removing the fluid from the body.

3. The method of claim 1, wherein the fluid comprises an antibiotic fluid.

4. The method of claim 1, wherein the fluid comprises a saline solution.

5. The method of claim 1, wherein the fluid comprises a diagnostic or therapeutic agent.

6. The method of claim 1, wherein the fluid exits the pliable membrane at a location disposed between the first and second retention members.

7. The method of claim 1, wherein the surgical access device comprises a plurality of fluid delivery regions and a plurality of fluid removal regions, and wherein the plurality of fluid delivery regions and the plurality of fluid removal regions are disposed between the first and the second retention members.

8. The method of claim 1, wherein the inner layer and the outer layer are joined together at a plurality of locations thereby forming a quilted pattern which prevents billowing of the pliable membrane.

9. The method of claim 1, wherein a porous material is disposed in the space.

10. The method of claim 1, wherein the pliable membrane comprises a plurality of perforations disposed between the first and second retention members, the plurality of perforations disposed away from the first and second retention members, and wherein the fluid exits at least some of the plurality of perforations and contacts the wall of the surgical site.

11. A method for retracting tissue in a surgical site in a body, the method comprising:
    inserting at least a portion of a surgical access device into an incision, wherein the surgical access device comprises a first retention member, a second retention member, a pliable membrane coupled to the first retention member and the second retention member, and a fluid removal conduit coupled to the first retention member;
    advancing the first retention member into the body through the incision;
    placing the second retention member outside the body;
    retracting the tissue using the pliable membrane;
    introducing a fluid into the surgical access device such that the fluid exits a first section of the pliable membrane and wherein the introduced fluid flows out of the surgical access device into the body before being suctioned back into the surgical access device,
    suctioning the fluid from the body into the surgical access device, wherein the fluid flows from the body through a second section of the pliable membrane not in direct fluid communication with the first section, and wherein the fluid enters the pliable membrane at a location disposed between the first and the second retention members; and
    removing the fluid from the body.

12. The method of claim 11, further comprising coupling a suction device to the fluid removal conduit.

13. The method of claim 11, wherein the surgical access device comprises a plurality of fluid delivery regions and a plurality of fluid removal regions, and wherein the plurality of fluid delivery regions and the plurality of fluid removal regions are disposed between the first and the second retention members.

14. The method of claim 11, wherein the pliable membrane comprises an inner layer and an outer layer joined together at a plurality of locations thereby forming a quilted pattern which prevents billowing of the pliable membrane.

15. The method of claim 14, wherein a porous material is disposed in a space between the inner layer and the outer layer.

16. A method for retracting tissue in a surgical site in a body, the method comprising:
    inserting a retraction device into an incision;
    retracting tissue;

introducing fluid into the retraction device; and forcing the fluid out of the retraction device into the surgical site, wherein the retraction device comprises a pliable membrane comprising an inner layer and an outer layer with a space therebetween, and wherein the fluid exits an opening in a lateral surface of a first section of the pliable membrane, and wherein the fluid flows through the space, wherein the introduced fluid contacts a wall of the surgical site; and suctioning at least a portion of the fluid after said fluid contacts the wall of the surgical site in through a lateral surface of a second section of the pliable membrane not in direct fluid communication with the first section of the pliable membrane.

17. The method of claim 16, wherein forcing the fluid out of the retraction device comprises forcing the fluid through a channel system that substantially circumscribes the retraction device.

18. The method of claim 16, wherein forcing the fluid out of the retraction device comprises forcing the fluid through a porous material.

19. The method of claim 16, wherein the retraction device comprises an upper portion and a lower portion that are not in direct fluid communication, wherein forcing the fluid out of the retraction device comprises forcing the fluid out of the upper portion and suctioning the fluid from the surgical site comprises suctioning the fluid into the lower portion.

20. The method of claim 16, wherein the inner layer and the outer layer are joined together at a plurality of locations thereby forming a quilted pattern which prevents billowing of the pliable membrane.

21. The method of claim 16, wherein a porous material is disposed in the space.

22. The method of claim 16, wherein the retraction device comprises first and second retention members, and the pliable membrane comprises a plurality of perforations disposed between the first and second retention members, the plurality of perforations disposed away from the first and second retention members, and wherein the fluid exits at least some of the plurality of perforations and contacts the wall of the surgical site.

* * * * *